United States Patent
Kennedy et al.

(10) Patent No.: US 12,234,518 B2
(45) Date of Patent: Feb. 25, 2025

(54) COMPOSITIONS AND METHODS FOR ANALYZING DNA USING PARTITIONING AND BASE CONVERSION

(71) Applicant: GUARDANT HEALTH, INC., Redwood City, CA (US)

(72) Inventors: Andrew Kennedy, San Diego, CA (US); William J. Greenleaf, Menlo Park, CA (US)

(73) Assignee: Guardant Health, Inc., Palo Alto, CA (US)

(*) Notice: Subject to any disclaimer, the term of this patent is extended or adjusted under 35 U.S.C. 154(b) by 174 days.

(21) Appl. No.: 17/507,697

(22) Filed: Oct. 21, 2021

(65) Prior Publication Data

US 2022/0154286 A1 May 19, 2022

Related U.S. Application Data

(60) Provisional application No. 63/105,184, filed on Oct. 23, 2020.

(51) Int. Cl.
| | | |
|---|---|---|
| *C12Q 1/6886* | (2018.01) | |
| *C12N 9/22* | (2006.01) | |
| *C12N 15/10* | (2006.01) | |

(52) U.S. Cl.
CPC ............ *C12Q 1/6886* (2013.01); *C12N 9/22* (2013.01); *C12N 15/1065* (2013.01); *C12N 2800/80* (2013.01); *C12Q 2600/112* (2013.01); *C12Q 2600/154* (2013.01); *C12Q 2600/156* (2013.01)

(58) Field of Classification Search
None
See application file for complete search history.

(56) References Cited

U.S. PATENT DOCUMENTS

| | | |
|---|---|---|
| 5,912,148 A | 6/1999 | Eggerding |
| 6,130,073 A | 10/2000 | Eggerding |
| 6,210,891 B1 | 4/2001 | Nyren et al. |
| 6,258,568 B1 | 7/2001 | Nyren |
| 6,582,908 B2 | 6/2003 | Fodor et al. |
| 6,833,246 B2 | 12/2004 | Balasubramanian |
| 6,969,488 B2 | 11/2005 | Bridgham et al. |
| 7,115,400 B1 | 10/2006 | Adessi et al. |
| 7,169,560 B2 | 1/2007 | Lapidus et al. |
| 7,170,050 B2 | 1/2007 | Turner et al. |
| 7,282,337 B1 | 10/2007 | Harris |
| 7,302,146 B2 | 11/2007 | Turner et al. |
| 7,313,308 B2 | 12/2007 | Turner et al. |
| 7,329,492 B2 | 2/2008 | Hardin et al. |
| 7,476,503 B2 | 1/2009 | Turner et al. |
| 7,482,120 B2 | 1/2009 | Buzby |
| 7,501,245 B2 | 3/2009 | Quake et al. |
| 7,537,898 B2 | 5/2009 | Bost et al. |
| 8,486,630 B2 | 7/2013 | Pan et al. |
| 9,074,013 B2 | 7/2015 | Rehli |
| 9,598,731 B2 | 3/2017 | Talasaz |
| 9,611,510 B2 | 4/2017 | He et al. |
| 9,738,894 B2 | 8/2017 | Elmen et al. |
| 9,850,523 B1 | 12/2017 | Chudova et al. |
| 9,902,992 B2 | 2/2018 | Talasaz et al. |
| 10,612,088 B2 | 4/2020 | Shishkin et al. |
| 2001/0053519 A1 | 12/2001 | Fodor et al. |
| 2003/0152490 A1 | 8/2003 | Trulson et al. |
| 2009/0208941 A1 | 8/2009 | Berlin et al. |
| 2010/0105049 A1 | 4/2010 | Ehrich et al. |
| 2011/0160078 A1 | 6/2011 | Fodor et al. |
| 2011/0237444 A1 | 9/2011 | Clancy et al. |
| 2012/0208193 A1 | 8/2012 | Okino et al. |
| 2013/0143211 A1 | 6/2013 | Ehrich et al. |
| 2013/0157266 A1 | 6/2013 | Hanna et al. |
| 2013/0244885 A1 | 9/2013 | Wang et al. |
| 2014/0322707 A1 | 10/2014 | He et al. |

(Continued)

FOREIGN PATENT DOCUMENTS

| | | |
|---|---|---|
| EP | 1693468 A1 | 8/2006 |
| EP | 2805769 A1 | 11/2014 |

(Continued)

OTHER PUBLICATIONS

Nair, S. et al. "Enzymatic cleavage of uracil-containing single-stranded DNA linkers for the efficient release of affinity-selected circulating tumor cells" Chem Commun (2015) 51(15):3266-3269.
Nair, S.S. et al. "Comparison of methyl-DNA immunoprecipitation (MeDIP) and methyl-CpG binding domain (MBD) protein capture for genome-wide DNA methylation analysis reveal CpG sequence coverage bias" Epigenetics (2011) 6 (1):34-44.
Newman, et al. An ultrasensitive method for quantitating circulating tumor DNA with broad patient coverage. Nat Med. May 2014;20(5):548-54. doi: 10.1038/nm.3519. Epub Apr. 6, 2014.
Niazi, U. et al. "DISMISS: detection of stranded methylation in MeDIP-Seq data" BMC Bioinformatics (2016) 17:295 12 pages.
Ning, Z. et al. "SSAHA: A Fast Search Method for Large DNA Databases" Genome Res (2001) 11:1725-1729.
Ooki, A. et al. "A Panel of Novel Detection and Prognostic Methylated DNA Markers in Primary Non-Small Cell Lung Cancer and Serum DNA" (2017) Clin. Cancer Res. 23:7141-7152.

(Continued)

*Primary Examiner* — Nancy J Leith
*Assistant Examiner* — Jessica D Parisi
(74) *Attorney, Agent, or Firm* — Indhu Kanakaraj

(57) ABSTRACT

The present disclosure provides compositions and methods related to analyzing DNA, such as cell-free DNA. In some embodiments, the cell-free DNA is from a subject having or suspected of having cancer and/or the cell-free DNA includes DNA from cancer cells. In some embodiments, the DNA is partitioned into a first subsample and a second subsample, wherein the first subsample comprises DNA with a nucleotide modification (e.g., a cytosine modification) in a greater proportion than the second subsample, and the second subsample is subjected to a procedure that affects a first nucleobase in the DNA differently from a second nucleobase in the DNA of the first subsample, and the DNA is sequenced in a manner that distinguishes the first nucleobase from the second nucleobase in the DNA of the second subsample.

24 Claims, 7 Drawing Sheets

(56) References Cited

U.S. PATENT DOCUMENTS

| | | |
|---|---|---|
| 2014/0363815 A1 | 12/2014 | Dahl et al. |
| 2015/0044687 A1 | 2/2015 | Schmitt et al. |
| 2015/0299812 A1 | 10/2015 | Talasaz |
| 2015/0368708 A1 | 12/2015 | Talasaz |
| 2016/0040229 A1 | 2/2016 | Talasaz et al. |
| 2016/0046986 A1 | 2/2016 | Eltoukhy et al. |
| 2016/0047001 A1 | 2/2016 | Larisch et al. |
| 2016/0108476 A1 | 4/2016 | Schweiger et al. |
| 2016/0201142 A1 | 7/2016 | Lo et al. |
| 2017/0211143 A1 | 7/2017 | Shendure et al. |
| 2018/0120304 A1 | 5/2018 | Rao et al. |
| 2018/0251848 A1 | 9/2018 | Diehn et al. |
| 2018/0305738 A1 | 10/2018 | Kennedy et al. |
| 2019/0144848 A1 | 5/2019 | Carvalho et al. |
| 2019/0390253 A1 | 12/2019 | Kennedy et al. |
| 2020/0248272 A1 | 8/2020 | Kennedy et al. |
| 2021/0115502 A1 | 4/2021 | Mortimer et al. |
| 2022/0162670 A1 | 5/2022 | Kennedy et al. |

FOREIGN PATENT DOCUMENTS

| | | | |
|---|---|---|---|
| WO | 2015061359 A1 | 4/2015 | |
| WO | 2015159292 A2 | 10/2015 | |
| WO | 2016015058 A2 | 1/2016 | |
| WO | 2016115530 A1 | 7/2016 | |
| WO | 2017181146 A1 | 10/2017 | |
| WO | 2017181161 A1 | 10/2017 | |
| WO | 2017184707 A1 | 10/2017 | |
| WO | 2017190215 A1 | 11/2017 | |
| WO | 2018005811 A1 | 1/2018 | |
| WO | 2018009723 A1 | 1/2018 | |
| WO | 2018119452 A2 | 6/2018 | |
| WO | 2019010564 A1 | 1/2019 | |
| WO | WO 2019/136413 A4 * | 7/2019 | ........... C12N 9/0071 |
| WO | 2020006369 A1 | 1/2020 | |
| WO | 2020160414 A1 | 8/2020 | |

OTHER PUBLICATIONS

Palmisano, W. et al. "Aberrant Promoter Methylation of the Transcription Factor Genes PAX5 alpha and beta in Human Cancers" Cancer Res (2003) 63:4620-4625.

Paweletz, C.P. et al. "Bias-corrected targeted next-generation sequencing for rapid, multiplexed detection of actionable alterations in cell-free DNA from advanced lung cancer patients" Clin Canc Res (2016) 22(4):915-922.

Pearson, W.R. et al. "Improved tools for biological sequence comparison" PNAS (1988) 85:2444-2448.

Phallen, J. et al. "Direct detection of early-stage cancers using circulating tumor DNA" Sci Trans Med (2017) vol. 9, Issue 403, eaan2415DOI: 10.1126/scitranslmed.aan2415.

Reuter, J.A. et al. "Simul-seq: combined DNA and RNA sequencing for whole-genome and transcriptome profiling", Nature Methods (Oct. 10, 2016) 13(11):953-958.

Rhee, H.S. et al. "Comprehensive genome-wide protein-DNA interactions detected at single-nucleotide resolution" Cell (2011) 147:1408-1419.

Riebler, A. et al. "BayMeth: improved DNA methylation quantification for affinity capture sequencing data using a flexible Bayesian approach" Genome Biology (2014) 15:R35 19 pages.

Robinson, M.D. et al. "Evaluation of affinity-based genome-wide DNA methylation data: Effects of CpG density, amplification bias, and copy number variation" Genome Research (2010) 20(12):1719-1729.

Rohland, N. et al. "Cost-effective, high-throughput DNA sequencing libraries for multiplexed target capture" Genome Res (2012) 22(5):939-946.

Schneider, K.U. et al. "Correlation of SHOX2 Gene Amplification and DNA Methylation in Lung Cancer Tumors" BMC Cancer (2011) 11:102.

Schutsky, E.K. et al., "Nondestructive, base-resolution sequencing of 5-hydroxymethylcytosine using a DNA deaminase" Nature Biotech (2018); 36:1083-1090.

Severin, P.M.D. et al. "Cytosine methylation alters DNA mechanical properties" Nucl Acids Res (2011) 39:8740-8751.

Shen, S.Y. et al. "Sensitive tumour detection and classification using plasma cell-free DNA methylomes" Nature (2018) 563(7732):579-583.

Shi, Y-X et al. "Genome-wide DNA methylation profiling reveals novel epigenetic signatures in squamous cell lung cancer" BMC Genomics (2017) 18:901.

Skvortsova, T.E. et al. "Cell-free and cell-bound circulating DNA in breast tumours: DNA quantification and analysis of tumour-related gene methylation" Br J Cancer (2006) 94(10):1492-1495.

Smallwood, S.A. et al. "Single-cell genome-wide bisulfite sequencing for assessing epigenetic heterogeneity" Nature Methods (2014) 11(8):817-820.

Snyder, M.W. et al. "Cell-free DNA Comprises an In Vivo Nucleosome Footprint that Informs Its Tissues-Of-Origin" Cell (2016) 164:57-68 & Supplemental Information.

Song, C-X. et al. "Selective chemical labeling reveals the genome-wide distribution of 5-hydroxymethylcytosine" Nature Biotech (2011) 29:68-72.

Stirzaker, C. et al. "Methylome sequencing in triple-negative breast cancer reveals distinct methylation clusters with prognostic value" Nature Comm (2015) 6(5899) (15 pages).

Sun, Q et al. "N6-methyladenine functions as a potential epigenetic mark in eukaryotes" Bioessays (2015) 37:1155-1162.

Suzuki, H. et al. "Genome-wide Profiling of Chromatin Signatures Reveals Epigenetic Regulation of MicroRNA Genes In Colorectal Cancer" Cancer Research (2011) 71(17):5646-5658.

Thakur, B.K. et al. "Double-stranded DNA in exosomes: a novel biomarker in cancer detection" Cell Research—Xibao Yanjiu (Apr. 8, 2014) 24(6):766-769.

Toyooka, K.O. et al. "Loss of Expression and Aberrant Methylation of the CDH13 (H-Cadherin) Gene in Breast and Lung Carcinomas" Cancer Res. (2001) 61:4556-4560.

Vaisvila, R. et al. "EM-seq: Detection of DNA Methylation at Single Base Resolution from Picograms of DNA" bioRxiv (2019) DOI:10.1101/2019.12.20.884692.

Voelkerding, K.V. et al. "Next-generation sequencing: from basic research to diagnostics" Clin Chem (2009) 55:641-658.

Warton, K. et al. "Methylation of cell-free circulating DNA in the diagnosis of cancer" Frontiers in Mol Biosciences (2015) 2(13), 10 pages.

Warton, K. et al. "Methylation-capture and Next-Generation Sequencing of free circulating DNA from human plasma" BMC Genomics (2014) 15:476 13 pages.

Wielscher, M. et al. "Methyl-binding domain protein-based DNA isolation from human blood serum combines DNA analyses and serum-autoantibody testing" BMC Clin Path (2011) 11:11 (9 pages).

Yamashita, R. et al. "DBTSS: DataBase of Human Transcription Start Sites, progress report 2006" Nucleic Acids Res. (2006) 34(Database issue): D86-D89.

Yigit, E. et al. "Genome and metagenome sequencing: Using the human methyl-binding domain to partition genomic DNA derived from plant tissues" Appl Plant Sci (2014) 2(11):1400064.

Yu, M. et al. "Base-Resolution Analysis of 5-Hydroxymethylcytosine in the Mammalian Genome" Cell (2012) 149 (6):1368-1380.

Zhao, Y. et al. "Methylcap-Seq Reveals Novel DNA Methylation Markers for the Diagnosis and Recurrence Prediction of Bladder Cancer in a Chinese Population" PLoS One 7(4):e35175 (12 pages), 2012.

International search report & written opinion for International Application No. PCT/US2021/056106 dated Mar. 2, 2022.

Astier, Y. et al. "Toward Single Molecule DNA Sequencing: Direct Identification of Ribonucleoside and Deoxyribonucleoside 5'-Monophosphates by Using an Engineered Protein Nanopore Equipped with a Molecular Adapter" J Am Chem Soc (2006) 128(5):1705-1710.

Belinsky, S.A. "Unmasking the lung cancer epigenome" Annu. Rev. Physiol. (2015) 77:453-474.

(56) References Cited

OTHER PUBLICATIONS

Bock, C. et al. "Quantitative comparison of genome-wide DNA methylation mapping technologies" Nature Biotech (2010) 28:1106-1114.
Booth, M.J. et al. "Quantitative sequencing of 5-methylcytosine and 5-hydroxymethylcytosine at single-base resolution" Science (2012) 336(6083):934-937.
Burnham, P. et al. "Single-stranded DNA library preparation uncovers the origin and diversity of ultrashort cell-free DNA in plasma" Sci Reports (Jun. 14, 2016) 6(1), XP055472868, DOI: 10.1038/srep27859.
Clark, T.A. et al. "Analytical Validation of a Hybrid Capture Based Next-Generation Sequencing Clinical Assay for Genomic Profiling of Cell-Free Circulating Tumor DNA," J. Mol. Diagnostics (2018) 20(5):686-702.
Cock, PJA, et al. "The Sanger FASTQ file format for sequences with quality scores, and the Solexa/Illumina FASTQ variants" NAR (2009) 38(6):1767-1771.
Cuddapah, S. et al. "Global analysis of the insulator binding protein CTCF in chromatin barrier regions reveals demarcation of active and repressive domains" Genome Res (2009) 19:24-32.
Danecek, P. et al. "The variant call format and VCFtools" Bioinformatics (2011) 27(15):2156-2158.
Dey, S.S. et al. "Integrated genome and transcriptome sequencing of the same cell" Nature Biotech (Jan. 19, 2015) 33 (3):285-589.
Ehrlich, M. "DNA hypomethylation in cancer cells" Epigenomics 1:239-259, 2019.
Fisher et al., "Characterization of cytosine methylated regions and 5-cytosine DNA methyltransferase (Ehmeth) in the protozoan parasite Entamoeba histolytica," Nucleic Acids Research, 2004, vol. 32, No. 1, pp. 287-297.
Freier, S.M. et al. "The ups and downs of nucleic acid duplex stability: structure-stability studies on chemically-modified DNA:RNA duplexes" Nucl Acids Res (1997) 25:4429-4443.
Furonaka, O. et al. "Aberrant methylation and loss of expression of O6-methylguanine-DNA methyltransferase in pulmonary squamous cell carcinoma and adenocarcinoma" Pathol Int (2005) 55:303-309.
Gale, D. et al. "Development of a highly sensitive liquid biopsy platform to detect clinically-relevant cancer mutations at low allele fractions in cell-free DNA" PLoS One (2018) 13:e0194630.
Gansauge, M-T. et al. "Single-stranded DNA library preparation for the sequencing of ancient or damaged DNA" Nature Protocols (2013) 3:737-748.
Gomes, A. et al. "Promoter hypermethylation of DNA repair genes MLH1 and MSH2 in adenocarcinomas and squamous cell carcinomas of the lung" Rev. Port. Pneumol. (2014) 20:20-30.
Greer, E.L. et al. "DNA Methylation on N6-Adenine in C. elegans" Cell (2015) 161(4):868-878.
Guo, M. et al. "Hypermethylation of the GATA genes in lung cancer" Clin Cancer Res (2004) 10(23):7917-7924.
Guo, Y.A. et al. "Mutation hotspots at CTCF binding sites coupled to chromosomal instability in gastrointestinal cancers" Nature Commun (2018) 9:1520.
Han, D. et al. "A highly sensitive and robust method for genome-wide 5hmC profiling of rare cell populations" Mol Cell. (2016) 63(4):711-719.
Heller, G. et al. "Expression and methylation pattern of TSLC1 cascade genes in lung carcinomas" Oncogene (2006) 25:959-968.
Hon, G.C. et al. "Global DNA hypomethylation coupled to repressive chromatin domain formation and gene silencing in breast cancer" Genome Res (2012) 22:246-258.
Hopkins-Donaldson, S. et al. "Silencing of death receptor and caspase-8 expression in small cell lung carcinoma cell lines and tumors by DNA methylation" Cell Death Differ. (2003) 10:356-64.
Hulbert, A. et al. "Early Detection of Lung Cancer Using DNA Promoter Hypermethylation in Plasma and Sputum" Clin. Cancer Res. (2017) 23:1998-2005.
International search report and written opinion dated Dec. 15, 2020 for PCT/US2020/053610.
Iurlaro, M. et al. "A screen for hydroxymethylcytosine and formylcytosine binding proteins suggests functions in transcription and chromatin regulation" Genome Biology (2013) 14:R119.
Jeong, H.M. et al. "Efficiency of methylated DNA immunoprecipitation bisulphite sequencing for whole-genome DNA methylation analysis" Epigenomics (2016) 8(8):1061-1077.
Jin, H. et al. "Circulating Methylated DNA as Biomarkers for Cancer Detection" Methylation: From DNA, RNA and Histones to Diseases and Treatment (2012) InTech. XP055479454, DOI:10.5772./51419.
Kang, S. et al. "CancerLocator: non-invasive cancer diagnosis and tissue-of origin prediction using methylation profiles of cell-free DNA" Genome Biology (2017) 18(1):53 XP055682390.
Katainen, R. et al. "CTCF/cohesin-binding sites are frequently mutated in cancer" Nature Genetics (2015) 47:818-821.
Kikuchi, S. et al. "Promoter Methylation of DAL-1/4.1B Predicts Poor Prognosis in Non Small Cell Lung Cancer" Clin Canc Res (2005) 11:2954-2961.
Kim et al., "Whole genome MBD-seq and RRBS analyses reveal that hypermethylation of gastrointestinal hormone receptors is associated with gastric carcinogenesis," Experimental & Molecular Medicine (2018) 50:156 (14 pages).
Kim, D-H. et al. "p16INK4a and Histology-specific Methylation of CpG Islands by Exposure to Tobacco Smoke in Non-Small Cell Lung Cancer" Canc Res (2001) 61:3419-3424.
Kim, D-H. et al. "Promoter methylation of DAP-kinase: association with advanced stage in non-small cell lung cancer" Oncogene. (2001) 20:1765-1770.
Kinde, et al. Detection and quantification of rare mutations with massively parallel sequencing. Proc Natl Acad Sci U S A. Jun. 7, 2011;108(23):9530-5. doi: 10.1073/pnas.1105422108. Epub May 17, 2011.
Kinde, et al. Supplemental Information, Detection and quantification of rare mutations with massively parallel sequencing. Proc Natl Acad Sci U S A. Jun. 7, 2011;108(23):1-10.
Kou, R. et al. "Benefits and Challenges with Applying Unique Molecular Identifiers in Next Generation Sequencing to Detect Low Frequency Mutations" PLoS One (2016) 11: e0146638, https://doi.org/10.1371/journal.pone.0146638.
Kumar, S. et al. "Epigenetics of Modified DNA Bases: 5-Methylcytosine and Beyond" Frontiers Genet (2018) 9:640.
Lam, K. et al. "DNA methylation based biomarkers in colorectal cancer: A systematic review" Biochim Biophys Acta (2016 ) 1866(1):106-20.
Levy, S.E. et al. "Advancements in Next-Generation Sequencing" Ann Rev Genomics & Hum Genetics (2016) 17:95-115.
Li et al., "Combining MeDIP-seq and MRE-seq to investigate genome-wide CpG methylation," Methods. Jan. 15, 2015; 72: 29-40 (28 pages).
Li, et al., The Sequence Alignment/Map format and SAMtools, Bioinformatics, 2009, 25(16):2078-9.
Licchesi, J. et al. "Epigenetic alteration of Wnt pathway antagonists in progressive glandular neoplasia of the lung" Carcinogenesis (2008) 29:895-904.
Lissa, D. et al. "Methylation analyses in liquid biopsy" Transl Lung Cancer Res (2016) 5(5):492-504.
Liu, L. et al. "Comparison of Next-Generation Sequencing Systems" J Biomed & Biotech (2012) Article ID251364:1-11.
Liu, Y. et al. "Bisulfite-free direct detection of 5-methylcytosine and 5-hydroxymethylcytosine at base resolution" Nature Biotech (2019) 37(4):424-429.
MacLean, D. et al. "Application of 'next-generation' sequencing technologies to microbial genetics" Nature Rev Microbiol (2009) 7:287-296.
Martin, D. et al. "Genome-wide CTCF distribution in vertebrates defines equivalent sites that aid the identification of disease-associated genes" Nature Structural Mol Bio (2011) 18:708-714.
Moss, J. et al. "Comprehensive human cell-type methylation atlas reveals origins of circulating cell-free DNA in health and disease" Nat Comm (2018) 9:5068.

\* cited by examiner

COMPOSITIONS AND METHODS FOR ANALYZING DNA USING PARTITIONING AND BASE CONVERSION

CROSS-REFERENCE TO RELATED APPLICATIONS

This application claims the benefit of priority of U.S. Provisional Patent Application No. 63/105,184, filed Oct. 23, 2020, which is incorporated by reference herein in its entirety for all purposes.

FIELD OF THE INVENTION

The present disclosure provides compositions and methods related to analyzing DNA, such as cell-free DNA. In some embodiments, the cell-free DNA is from a subject having or suspected of having cancer and/or the cell-free DNA includes DNA from cancer cells. In some embodiments, the DNA is partitioned into a first subsample and a second subsample, wherein the first subsample comprises DNA with a nucleotide modification (e.g., a cytosine modification) in a greater proportion than the second subsample, and the second subsample is subjected to a procedure that affects a first nucleobase in the DNA differently from a second nucleobase in the DNA of the first subsample, and the DNA is sequenced in a manner that distinguishes the first nucleobase from the second nucleobase in the DNA of the second subsample.

INTRODUCTION AND SUMMARY

Cancer is responsible for millions of deaths per year worldwide. Early detection of cancer may result in improved outcomes because early-stage cancer tends to be more susceptible to treatment.

Improperly controlled cell growth is a hallmark of cancer that generally results from an accumulation of genetic and epigenetic changes, such as copy number variations (CNVs), single nucleotide variations (SNVs), gene fusions, insertions and/or deletions (indels), epigenetic variations including modification of cytosine (e.g., 5-methylcytosine, 5-hydroxymethylcytosine, and other more oxidized forms) and association of DNA with chromatin proteins and transcription factors.

Biopsies represent a traditional approach for detecting or diagnosing cancer in which cells or tissue are extracted from a possible site of cancer and analyzed for relevant phenotypic and/or genotypic features. Biopsies have the drawback of being invasive.

Detection of cancer based on analysis of body fluids ("liquid biopsies"), such as blood, is an intriguing alternative based on the observation that DNA from cancer cells is released into body fluids. A liquid biopsy is noninvasive (sometimes requiring only a blood draw). Current methods of cancer diagnostic assays of cell-free nucleic acids (e.g., cell-free DNA or cell-free RNA) may focus on the detection of tumor-related somatic variants, including single nucleotide variants (SNVs), copy number variations (CNVs), fusions, and indels (i.e., insertions or deletions), which are all mainstream targets for liquid biopsy. There is growing evidence that non-sequence modifications like methylation status and fragmentomic signal in cell-free DNA can provide information on the source of cell-free DNA and disease level. The non-sequence modifications of the cell-free DNA, when combined with somatic mutation calling, can yield a more comprehensive assessment of tumor status than that available from either approach alone. However, it has been challenging to develop accurate and sensitive methods for analyzing liquid biopsy material that provides detailed information regarding nucleobase modifications given the low concentration and heterogeneity of cell-free DNA.

Isolating and processing the fractions of cell-free DNA useful for further analysis in liquid biopsy procedures is an important part of these methods. Accordingly, there is a need for improved methods and compositions for analyzing cell-free DNA, e.g., in liquid biopsies.

The present disclosure aims to meet the need for improved analysis of cell-free DNA and/or provide other benefits. Accordingly, the following exemplary embodiments are provided.

Embodiment 1 is a method of analyzing DNA in a sample, the method comprising:
a) partitioning the sample into a plurality of subsamples, including a first subsample and a second subsample, wherein the first subsample comprises DNA with a cytosine modification in a greater proportion than the second subsample;
b) subjecting the second subsample to a procedure that affects a first nucleobase in the DNA differently from a second nucleobase in the DNA of the second subsample, wherein the first nucleobase is a modified or unmodified nucleobase, the second nucleobase is a modified or unmodified nucleobase different from the first nucleobase, and the first nucleobase and the second nucleobase have the same base pairing specificity, thereby producing a treated subsample;
c) capturing a target region set comprising epigenetic target regions from the treated subsample; and
d) sequencing DNA in the target region set and DNA from the first subsample, wherein DNA from the second subsample is sequenced in a manner that distinguishes the first nucleobase from the second nucleobase in the DNA of the target region set.

Embodiment 2 is a method of analyzing DNA in a sample, the method comprising:
a) capturing a target region set comprising epigenetic target regions from the sample;
b) partitioning the target region set into a plurality of subsamples, including a first subsample and a second subsample, wherein the first subsample comprises DNA with a cytosine modification in a greater proportion than the second subsample;
c) subjecting the second subsample to a procedure that affects a first nucleobase in the DNA differently from a second nucleobase in the DNA of the second subsample, wherein the first nucleobase is a modified or unmodified nucleobase, the second nucleobase is a modified or unmodified nucleobase different from the first nucleobase, and the first nucleobase and the second nucleobase have the same base pairing specificity, thereby producing a treated subsample; and
d) sequencing DNA from the first subsample and DNA from the second subsample, wherein DNA from the second subsample is sequenced in a manner that distinguishes the first nucleobase from the second nucleobase in the DNA of the target region set.

Embodiment 3 is the method of any one of the preceding embodiments, wherein the target region set comprises a hypomethylation variable target region set.

Embodiment 4 is the method of the immediately preceding embodiment, wherein the hypomethylation variable target region set comprises regions having a lower degree of methylation in at least one type of tissue than the degree of methylation in cell-free DNA from a healthy subject.

Embodiment 5 is the method of embodiment 3 or 4, wherein the target region set comprises a methylation control target region set.

Embodiment 6 is the method of any one of the preceding embodiments, wherein the target region set comprises a fragmentation variable target region set.

Embodiment 7 is the method of the immediately preceding embodiment, wherein the fragmentation variable target region set comprises transcription start site regions.

Embodiment 8 is the method of embodiment 6 or 7, wherein the fragmentation variable target region set comprises CTCF binding regions.

Embodiment 9 is the method of any one of the preceding embodiments, wherein the target region set further comprises sequence-variable target regions.

Embodiment 10 is the method of the immediately preceding embodiment, wherein DNA molecules corresponding to the sequence-variable target region set are captured with a greater capture yield than DNA molecules corresponding to the epigenetic target region set.

Embodiment 11 is a method of analyzing DNA in a sample, the method comprising:
  a) partitioning the sample into a plurality of subsamples, including a first subsample and a second subsample, wherein the first subsample comprises DNA with a cytosine modification in a greater proportion than the second subsample;
  b) subjecting the second subsample to a procedure that affects a first nucleobase in the DNA differently from a second nucleobase in the DNA of the second subsample, wherein the first nucleobase is a modified or unmodified nucleobase, the second nucleobase is a modified or unmodified nucleobase different from the first nucleobase, and the first nucleobase and the second nucleobase have the same base pairing specificity, thereby producing a treated subsample; and
  c) sequencing DNA from the treated subsample and DNA from the first subsample in a manner that distinguishes the first nucleobase from the second nucleobase in the DNA of the target region set.

Embodiment 12 is the method of any one of the preceding embodiments, wherein the DNA of the first subsample is contacted with a methylation-sensitive nuclease, thereby degrading nonspecifically partitioned DNA in the first subsample.

Embodiment 13 is the method of any one of the preceding embodiments, wherein the DNA comprises cell-free DNA (cfDNA) obtained from a test subject.

Embodiment 14 is the method of any one of the preceding embodiments, further comprising capturing an additional target region set from the first subsample, wherein the DNA from the first subsample that is sequenced comprises the additional target region set.

Embodiment 15 is the method of any one of the preceding embodiments, further comprising subjecting the first subsample to a procedure that affects a first nucleobase in the DNA differently from a second nucleobase in the DNA of the second subsample, wherein the first nucleobase is a modified or unmodified nucleobase, the second nucleobase is a modified or unmodified nucleobase different from the first nucleobase, and the first nucleobase and the second nucleobase have the same base pairing specificity, thereby producing an additional treated subsample.

Embodiment 16 is the method of the immediately preceding embodiment, further comprising capturing an additional target region set from the additional treated subsample.

Embodiment 17 is the method of embodiment 14 or 16, wherein the additional target region set comprises a hypermethylation variable target region set.

Embodiment 18 is the method of the immediately preceding embodiment, wherein the hypermethylation variable target region set comprises regions having a higher degree of methylation in at least one type of tissue than the degree of methylation in cell-free DNA from a healthy subject.

Embodiment 19 is the method of embodiment 18 or 19, wherein the additional target region set comprises a methylation control target region set.

Embodiment 20 is the method of any one of embodiments 16-19, wherein the additional target region set comprises a fragmentation variable target region set.

Embodiment 21 is the method of the immediately preceding embodiment, wherein the fragmentation variable target region set comprises transcription start site regions.

Embodiment 22 is the method of embodiment 20 or 21, wherein the fragmentation variable target region set comprises CTCF binding regions.

Embodiment 23 is the method of any one of embodiments 16-22, wherein the additional target region set further comprises sequence-variable target regions.

Embodiment 24 is the method of the immediately preceding embodiment, wherein DNA molecules corresponding to the sequence-variable target region set are captured with a greater capture yield than DNA molecules corresponding to the epigenetic target region set.

Embodiment 25 is the method of any one of the preceding embodiments, wherein capturing comprises contacting DNA to be captured with a set of target-specific probes, whereby complexes of target-specific probes and DNA are formed.

Embodiment 26 is the method of the immediately preceding embodiment, wherein capturing further comprises separating the complexes from DNA not bound to target-specific probes, thereby providing captured DNA.

Embodiment 27 is the method of embodiment 25 or 26, wherein the set of target-specific probes is configured to capture DNA corresponding to the sequence-variable target region set with a greater capture yield than DNA corresponding to the epigenetic target region set.

Embodiment 28 is the method of any one of embodiments 9-22, comprising sequencing DNA molecules corresponding to the sequence-variable target region set to a greater depth of sequencing than DNA molecules corresponding to the epigenetic target region set.

Embodiment 29 is the method of any one of the preceding embodiments, wherein the DNA is amplified before the sequencing step, or the DNA is amplified before the capturing step.

Embodiment 30 is the method of any one of the preceding embodiments, further comprising ligating barcode-containing adapters to the DNA before capture, optionally wherein the ligating occurs before or simultaneously with amplification.

Embodiment 31 is the method of any one of the preceding embodiments, wherein partitioning the sample into a plurality of subsamples comprises partitioning on the basis of methylation level.

Embodiment 32 is the method of the immediately preceding embodiment, wherein the partitioning step comprises contacting the collected cfDNA with a methyl binding reagent immobilized on a solid support.

Embodiment 33 is the method of any one of the preceding embodiments, comprising differentially tagging the first subsample and second subsample or the first subsample and the treated subsample.

Embodiment 34 is the method of the immediately preceding embodiment, wherein DNA from the first subsample and the target region set or second subsample are pooled.

Embodiment 35 is the method of any one of embodiments 33-34, wherein DNA from the first subsample and the target region set or second subsample are sequenced in the same sequencing cell.

Embodiment 36 is the method of any one of the preceding embodiments, wherein the plurality of subsamples comprises a third subsample, which comprises DNA with a cytosine modification in a greater proportion than the second subsample but in a lesser proportion than the first subsample.

Embodiment 37 is the method of the immediately preceding embodiment, wherein the method further comprises differentially tagging the third subsample.

Embodiment 38 is the method of the immediately preceding embodiment, wherein DNA from the first subsample, DNA from the third sample, and the target region set are pooled, optionally wherein DNA from the first, second, and third subsamples is sequenced in the same sequencing cell.

Embodiment 39 is the method of any one of the preceding embodiments, further comprising determining a likelihood that the subject has cancer.

Embodiment 40 is the method of the immediately preceding embodiment, wherein the sequencing generates a plurality of sequencing reads; and the method further comprises mapping the plurality of sequence reads to one or more reference sequences to generate mapped sequence reads, and processing the mapped sequence reads corresponding to the sequence-variable target region set and to the epigenetic target region set to determine the likelihood that the subject has cancer.

Embodiment 41 is the method of any one of embodiments 1-38, wherein the test subject was previously diagnosed with a cancer and received one or more previous cancer treatments, optionally wherein the cfDNA is obtained at one or more preselected time points following the one or more previous cancer treatments, and sequencing the captured set of cfDNA molecules, whereby a set of sequence information is produced.

Embodiment 42 is the method of the immediately preceding embodiment, further comprising detecting a presence or absence of DNA originating or derived from a tumor cell at a preselected timepoint using the set of sequence information.

Embodiment 43 is the method of the immediately preceding embodiment, further comprising determining a cancer recurrence score that is indicative of the presence or absence of the DNA originating or derived from the tumor cell for the test subject, optionally further comprising determining a cancer recurrence status based on the cancer recurrence score, wherein the cancer recurrence status of the test subject is determined to be at risk for cancer recurrence when a cancer recurrence score is determined to be at or above a predetermined threshold or the cancer recurrence status of the test subject is determined to be at lower risk for cancer recurrence when the cancer recurrence score is below the predetermined threshold.

Embodiment 44 is the method of the immediately preceding embodiment, further comprising comparing the cancer recurrence score of the test subject with a predetermined cancer recurrence threshold, wherein the test subject is classified as a candidate for a subsequent cancer treatment when the cancer recurrence score is above the cancer recurrence threshold or not a candidate for a subsequent cancer treatment when the cancer recurrence score is below the cancer recurrence threshold.

Embodiment 45 is the method of any one of the preceding embodiments, wherein the cytosine modification is methylation.

Embodiment 46 is the method of any one of the preceding embodiments, wherein the cytosine modification is methylation at the 5 position of cytosine.

Embodiment 47 is the method of any one of the preceding embodiments, wherein the procedure to which the second subsample is subjected alters base-pairing specificity of the first nucleobase without substantially altering base-pairing specificity of the second nucleobase.

Embodiment 48 is the method of any one of the preceding embodiments, wherein the first nucleobase is a modified or unmodified cytosine and the second nucleobase is a modified or unmodified cytosine.

Embodiment 49 is the method of any one of the preceding embodiments, wherein the first nucleobase comprises unmodified cytosine (C).

Embodiment 50 is the method of any one of the preceding embodiments, wherein the second nucleobase comprises 5-methylcytosine (mC).

Embodiment 51 is the method of any one of the preceding embodiments, wherein the procedure to which the first subsample is subjected comprises bisulfite conversion.

Embodiment 52 is the method of any one of embodiments 1-49, wherein the first nucleobase comprises mC.

Embodiment 53 is the method of any one of the preceding embodiments, wherein the second nucleobase comprises 5-hydroxymethylcytosine (hmC).

Embodiment 54 is the method of embodiment 53, wherein the procedure to which the second subsample is subjected comprises protection of 5hmC.

Embodiment 55 is the method of embodiment 53, wherein the procedure to which the second subsample is subjected comprises Tet-assisted bisulfite conversion.

Embodiment 56 is the method of embodiment 53, wherein the procedure to which the second subsample is subjected comprises Tet-assisted conversion with a substituted borane reducing agent, optionally wherein the substituted borane reducing agent is 2-picoline borane, borane pyridine, tert-butylamine borane, or ammonia borane.

Embodiment 57 is the method of embodiment 56, wherein the substituted borane reducing agent is 2-picoline borane or borane pyridine.

Embodiment 58 is the method of any one of embodiments 52-54 or 56-57, wherein the second nucleobase comprises C.

Embodiment 59 is the method of any one of embodiments 52-54 or 58, wherein the procedure to which the second subsample is subjected comprises protection of hmC followed by Tet-assisted conversion with a substituted borane reducing agent, optionally wherein the substituted borane reducing agent is 2-picoline borane, borane pyridine, tert-butylamine borane, or ammonia borane.

Embodiment 60 is the method of embodiment 59, wherein the substituted borane reducing agent is 2-picoline borane or borane pyridine.

Embodiment 61 is the method of any one of embodiments 49, 50, 52-54, or 58, wherein the procedure to which the first subsample is subjected comprises protection of hmC followed by deamination of mC and/or C.

Embodiment 62 is the method of embodiment 61, wherein the deamination of mC and/or C comprises treatment with an AID/APOBEC family DNA deaminase enzyme.

Embodiment 63 is the method of any one of embodiments 54 or 58-62, wherein protection of hmC comprises glucosylation of hmC.

Embodiment 64 is the method of any one of embodiments 1-48, 50, 52, or 58, wherein the procedure to which the first subsample is subjected comprises chemical-assisted conversion with a substituted borane reducing agent, optionally wherein the substituted borane reducing agent is 2-picoline borane, borane pyridine, tert-butylamine borane, or ammonia borane.

Embodiment 65 is the method of embodiment 64, wherein the substituted borane reducing agent is 2-picoline borane or borane pyridine.

Embodiment 66 is the method of any one of embodiments 1-48, 50, 52, 58, or 64-65, wherein the first nucleobase comprises hmC.

Embodiment 67 is the method of any one of the preceding embodiments, wherein the DNA of the first subsample and the DNA of the second subsample are differentially tagged; after differential tagging, a portion of DNA from the second subsample or treated subsample is added to the first subsample or additional treated subsample or at least a portion thereof, thereby forming a pool; and sequence-variable target regions and epigenetic target regions are captured from the pool.

Embodiment 68 is the method of the immediately preceding embodiment, wherein the pool comprises less than or equal to about 45%, 40%, 35%, 30%, 25%, 20%, 15%, 10%, or 5% of the DNA of the second subsample.

Embodiment 69 is the method of the immediately preceding embodiment, wherein the pool comprises about 70-90%, about 75-85%, or about 80% of the DNA of the second subsample.

Embodiment 70 is the method of any one of embodiments 67-69, wherein the pool comprises substantially all of the DNA of the first subsample.

Embodiment 71 is the method of any one of embodiments 67-70, wherein the pool comprises substantially all of the DNA of the first subsample or treated first subsample.

Embodiment 72 is the method of any one of embodiments 67-72, wherein the first target region set is captured from at least a portion of the first subsample or treated first subsample after formation of the pool.

Embodiment 73 is the method of any one of embodiments 47-72, further comprising subjecting the first subsample to a procedure that affects a first nucleobase in the DNA differently from a second nucleobase in the DNA of the second subsample, wherein the procedure to which the first subsample is subjected is the same as the procedure to which the second subsample is subjected.

Embodiment 74 is the method of any one of embodiments 47-72, further comprising subjecting the first subsample to a procedure that affects a first nucleobase in the DNA differently from a second nucleobase in the DNA of the second subsample, wherein the procedure to which the first subsample is subjected is different from the procedure to which the second subsample is subjected.

I. BRIEF DESCRIPTION OF THE DRAWINGS

FIG. 1 illustrates an exemplary workflow according to certain embodiments of the disclosure beginning with a blood sample, in which cfDNA is isolated from the blood sample; the cfDNA is partitioned using a methyl-binding domain protein (MBD) into low and high methylation subsamples; and the low methylation subsample (and optionally the high methylation subsample) are subjected to a procedure (e.g., TAP) to differentially convert certain nucleotide forms to facilitate identification of nonspecifically partitioned molecules (e.g., conversion of methylated cytosine to thymine). The subsamples then undergo library preparation and enrichment for hypermethylated differentially methylated regions and hypomethylated differentially methylated regions (for the high and low methylation subsamples, respectively), followed by sequencing and analysis.

II. DETAILED DESCRIPTION OF CERTAIN EMBODIMENTS

Figure 1:
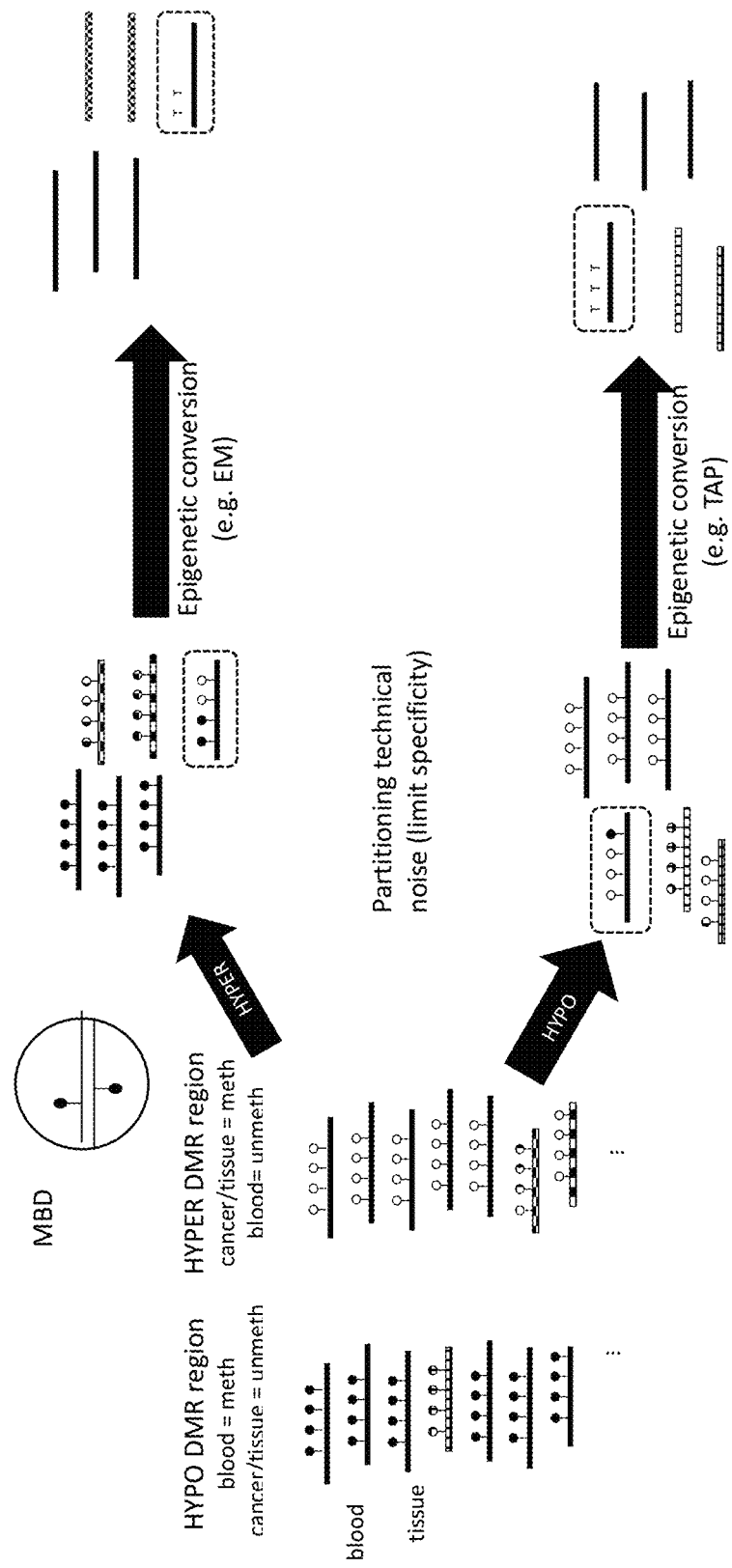
Figure 1:
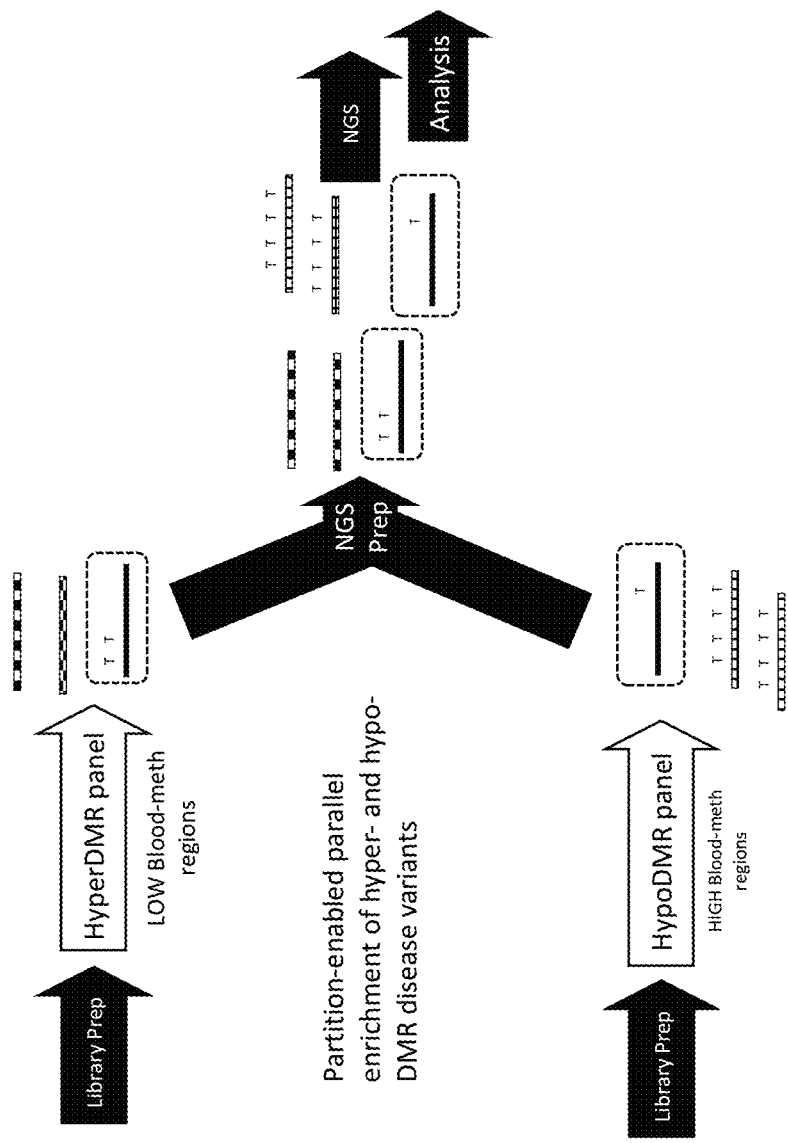

Reference will now be made in detail to certain embodiments of the invention. While the invention will be described in conjunction with such embodiments, it will be understood that they are not intended to limit the invention to those embodiments. On the contrary, the invention is intended to cover all alternatives, modifications, and equivalents, which may be included within the invention as defined by the appended claims.

Before describing the present teachings in detail, it is to be understood that the disclosure is not limited to specific compositions or process steps, as such may vary. It should be noted that, as used in this specification and the appended claims, the singular form "a", "an" and "the" include plural references unless the context clearly dictates otherwise. Thus, for example, reference to "a nucleic acid" includes a plurality of nucleic acids, reference to "a cell" includes a plurality of cells, and the like.

Numeric ranges are inclusive of the numbers defining the range. Measured and measurable values are understood to be approximate, taking into account significant digits and the error associated with the measurement. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings.

Unless specifically noted in the above specification, embodiments in the specification that recite "comprising" various components are also contemplated as "consisting of" or "consisting essentially of" the recited components; embodiments in the specification that recite "consisting of" various components are also contemplated as "comprising"

or "consisting essentially of" the recited components; and embodiments in the specification that recite "consisting essentially of" various components are also contemplated as "consisting of" or "comprising" the recited components (this interchangeability does not apply to the use of these terms in the claims).

The section headings used herein are for organizational purposes and are not to be construed as limiting the disclosed subject matter in any way. In the event that any document or other material incorporated by reference contradicts any explicit content of this specification, including definitions, this specification controls.

A. Definitions

"Cell-free DNA," "cfDNA molecules," or simply "cfDNA" include DNA molecules that naturally occur in a subject in extracellular form (e.g., in blood, serum, plasma, or other bodily fluids such as lymph, cerebrospinal fluid, urine, or sputum). While the cfDNA originally existed in a cell or cells in a large complex biological organism, e.g., a mammal, it has undergone release from the cell(s) into a fluid found in the organism, and may be obtained from a sample of the fluid without the need to perform an in vitro cell lysis step.

As used herein, "cellular nucleic acids" means nucleic acids that are disposed within one or more cells from which the nucleic acids have originated, at least at the point a sample is taken or collected from a subject, even if those nucleic acids are subsequently removed (e.g., via cell lysis) as part of a given analytical process.

As used herein, a modification or other feature is present in "a greater proportion" in a first sample or population of nucleic acid than in a second sample or population when the fraction of nucleotides with the modification or other feature is higher in the first sample or population than in the second population. For example, if in a first sample, one tenth of the nucleotides are mC, and in a second sample, one twentieth of the nucleotides are mC, then the first sample comprises the cytosine modification of 5-methylation in a greater proportion than the second sample.

As used herein, "without substantially altering base-pairing specificity" of a given nucleobase means that a majority of molecules comprising that nucleobase that can be sequenced do not have alterations of the base pairing specificity of the second nucleobase relative to its base pairing specificity as it was in the originally isolated sample. In some embodiments, 75%, 90%, 95%, or 99% of molecules comprising that nucleobase that can be sequenced do not have alterations of the base pairing specificity of the second nucleobase relative to its base pairing specificity as it was in the originally isolated sample.

As used herein, "base pairing specificity" refers to the standard DNA base (A, C, G, or T) for which a given base most preferentially pairs. Thus, for example, unmodified cytosine and 5-methylcytosine have the same base pairing specificity (i.e., specificity for G) whereas uracil and cytosine have different base pairing specificity because uracil has base pairing specificity for A while cytosine has base pairing specificity for G. The ability of uracil to form a wobble pair with G is irrelevant because uracil nonetheless most preferentially pairs with A among the four standard DNA bases.

As used herein, a "combination" comprising a plurality of members refers to either of a single composition comprising the members or a set of compositions in proximity, e.g., in separate containers or compartments within a larger container, such as a multiwell plate, tube rack, refrigerator, freezer, incubator, water bath, ice bucket, machine, or other form of storage.

The "capture yield" of a collection of probes for a given target set refers to the amount (e.g., amount relative to another target set or an absolute amount) of nucleic acid corresponding to the target set that the collection of probes captures under typical conditions. Exemplary typical capture conditions are an incubation of the sample nucleic acid and probes at 65° C. for 10-18 hours in a small reaction volume (about 20 µL) containing stringent hybridization buffer. The capture yield may be expressed in absolute terms or, for a plurality of collections of probes, relative terms. When capture yields for a plurality of sets of target regions are compared, they are normalized for the footprint size of the target region set (e.g., on a per-kilobase basis). Thus, for example, if the footprint sizes of first and second target regions are 50 kb and 500 kb, respectively (giving a normalization factor of 0.1), then the DNA corresponding to the first target region set is captured with a higher yield than DNA corresponding to the second target region set when the mass per volume concentration of the captured DNA corresponding to the first target region set is more than 0.1 times the mass per volume concentration of the captured DNA corresponding to the second target region set. As a further example, using the same footprint sizes, if the captured DNA corresponding to the first target region set has a mass per volume concentration of 0.2 times the mass per volume concentration of the captured DNA corresponding to the second target region set, then the DNA corresponding to the first target region set was captured with a two-fold greater capture yield than the DNA corresponding to the second target region set.

"Capturing" one or more target nucleic acids refers to preferentially isolating or separating the one or more target nucleic acids from non-target nucleic acids.

A "captured set" of nucleic acids refers to nucleic acids that have undergone capture.

A "target-region set" or "set of target regions" refers to a plurality of genomic loci targeted for capture and/or targeted by a set of probes (e.g., through sequence complementarity).

"Corresponding to a target region set" means that a nucleic acid, such as cfDNA, originated from a locus in the target region set or specifically binds one or more probes for the target-region set.

"Specifically binds" in the context of an probe or other oligonucleotide and a target sequence means that under appropriate hybridization conditions, the oligonucleotide or probe hybridizes to its target sequence, or replicates thereof, to form a stable probe:target hybrid, while at the same time formation of stable probe:non-target hybrids is minimized. Thus, a probe hybridizes to a target sequence or replicate thereof to a sufficiently greater extent than to a non-target sequence, to enable capture or detection of the target sequence. Appropriate hybridization conditions are well-known in the art, may be predicted based on sequence composition, or can be determined by using routine testing methods (see, e.g., Sambrook et al., Molecular Cloning, A Laboratory Manual, 2nd ed. (Cold Spring Harbor Laboratory Press, Cold Spring Harbor, NY, 1989) at §§ 1.90-1.91, 7.37-7.57, 9.47-9.51 and 11.47-11.57, particularly §§ 9.50-9.51, 11.12-11.13, 11.45-11.47 and 11.55-11.57, incorporated by reference herein).

"Sequence-variable target region set" refers to a set of target regions that may exhibit changes in sequence such as nucleotide substitutions (i.e., single nucleotide variations), insertions, deletions, or gene fusions or transpositions in neoplastic cells (e.g., tumor cells and cancer cells).

"Epigenetic target region set" refers to a set of target regions that may show sequence-independent changes in neoplastic cells (e.g., tumor cells and cancer cells) or that may show sequence-independent changes in cfDNA from subjects having cancer relative to cfDNA from healthy subjects. Examples of sequence-independent changes include, but not limited to, changes in methylation (increases or decreases), nucleosome distribution, CTCF binding, transcription start sites, and regulatory protein binding regions. For present purposes, loci susceptible to neoplasia-, tumor-, or cancer-associated focal amplifications and/or gene fusions may also be included in an epigenetic target region set because detection of a change in copy number by sequencing or a fused sequence that maps to more than one locus in a reference genome tends to be more similar to detection of exemplary epigenetic changes discussed above than detection of nucleotide substitutions, insertions, or deletions, e.g., in that the focal amplifications and/or gene fusions can be detected at a relatively shallow depth of sequencing because their detection does not depend on the accuracy of base calls at one or a few individual positions.

A nucleic acid is "produced by a tumor" or ctDNA or circulating tumor DNA, if it originated from a tumor cell. Tumor cells are neoplastic cells that originated from a tumor, regardless of whether they remain in the tumor or become separated from the tumor (as in the cases, e.g., of metastatic cancer cells and circulating tumor cells).

The term "methylation" or "DNA methylation" refers to addition of a methyl group to a nucleotide base in a nucleic acid molecule. In some embodiments, methylation refers to addition of a methyl group to a cytosine at a CpG site (cytosine-phosphate-guanine site (i.e., a cytosine followed by a guanine in a 5'→3' direction of the nucleic acid sequence). In some embodiments, DNA methylation refers to addition of a methyl group to adenine, such as in $N^6$-methyladenine. In some embodiments, DNA methylation is 5-methylation (modification of the 5th carbon of the 6-carbon ring of cytosine). In some embodiments, 5-methylation refers to addition of a methyl group to the 5C position of the cytosine to create 5-methylcytosine (5mC). In some embodiments, methylation comprises a derivative of 5mC. Derivatives of 5mC include, but are not limited to, 5-hydroxymethylcytosine (5-hmC), 5-formylcytosine (5-fC), and 5-caryboxylcytosine (5-caC). In some embodiments, DNA methylation is 3C methylation (modification of the 3rd carbon of the 6-carbon ring of cytosine). In some embodiments, 3C methylation comprises addition of a methyl group to the 3C position of the cytosine to generate 3-methylcytosine (3mC). Methylation can also occur at non CpG sites, for example, methylation can occur at a CpA, CpT, or CpC site. DNA methylation can change the activity of methylated DNA region. For example, when DNA in a promoter region is methylated, transcription of the gene may be repressed. DNA methylation is critical for normal development and abnormality in methylation may disrupt epigenetic regulation. The disruption, e.g., repression, in epigenetic regulation may cause diseases, such as cancer. Promoter methylation in DNA may be indicative of cancer The term "hypermethylation" refers to an increased level or degree of methylation of nucleic acid molecule(s) relative to the other nucleic acid molecules within a population (e.g., sample) of nucleic acid molecules. In some embodiments, hypermethylated DNA can include DNA molecules comprising at least 1 methylated residue, at least 2 methylated residues, at least 3 methylated residues, at least 5 methylated residues, or at least 10 methylated residues.

The term "hypomethylation" refers to a decreased level or degree of methylation of nucleic acid molecule(s) relative to the other nucleic acid molecules within a population (e.g., sample) of nucleic acid molecules. In some embodiments, hypomethylated DNA includes unmethylated DNA molecules. In some embodiments, hypomethylated DNA can include DNA molecules comprising 0 methylated residues, at most 1 methylated residue, at most 2 methylated residues, at most 3 methylated residues, at most 4 methylated residues, or at most 5 methylated residues.

The term "methylation-sensitive nuclease" refers to a nuclease that preferentially cuts unmethylated DNA relative to methylated DNA. For example, a methylation-sensitive nuclease may cut at or near a recognition sequence such as a restriction site in a manner dependent on lack of methylation of at least one of the nucleobases in the recognition sequence, such as a cytosine. In some embodiments, the nucleolytic activity of the methylation-sensitive nuclease is at least 10, 20, 50, or 100-fold higher on an unmethylated recognition site relative to a methylated control in a standard nucleolysis assay. Methylation-sensitive nucleases include methylation-sensitive restriction enzymes.

As used herein, "methylation sensitive restriction enzyme" or "MSRE" refers to a restriction enzyme that is sensitive to the methylation status of the DNA (e.g. cytosine methylation) i.e., the presence or absence of methyl group in a nucleotide base alters the rate at which the enzyme cleaves the target DNA. In some embodiments, the methylation sensitive restriction enzymes do not cleave the DNA if a particular nucleotide base is methylated at the recognition sequence. For example, HpaII is a methylation sensitive restriction enzyme with a recognition sequence "CCGG" and it does not cleave DNA if the second cytosine in the recognition sequence is methylated.

As used herein, "methylation status" can refer to the presence or absence of methyl group on a DNA base (e.g. cytosine) at a particular genomic position in a nucleic acid molecule. It can also refer to the degree of methylation in a nucleic acid sequence (e.g., highly methylated, low methylated, intermediately methylated or unmethylated nucleic acid molecules). The methylation status can also refer to the number of nucleotides methylated in a particular nucleic acid molecule.

As used herein, "mutation" refers to a variation from a known reference sequence and includes mutations such as, for example, single nucleotide variants (SNVs), and insertions or deletions (indels). A mutation can be a germline or somatic mutation. In some embodiments, a reference sequence for purposes of comparison is a wildtype genomic sequence of the species of the subject providing a test sample, typically the human genome.

As used herein, the terms "neoplasm" and "tumor" are used interchangeably. They refer to abnormal growth of cells in a subject. A neoplasm or tumor can be benign, potentially malignant, or malignant. A malignant tumor is a referred to as a cancer or a cancerous tumor.

As used herein, "next-generation sequencing" or "NGS" refers to sequencing technologies having increased throughput as compared to traditional Sanger- and capillary electrophoresis-based approaches, for example, with the ability to generate hundreds of thousands of relatively small sequence reads at a time. Some examples of next-generation sequencing techniques include, but are not limited to, sequencing by synthesis, sequencing by ligation, and sequencing by hybridization. In some embodiments, next-generation sequencing includes the use of instruments capable of sequencing single molecules. Example of commercially available instruments for performing next-generation sequencing include, but are not limited to, NextSeq, HiSeq, NovaSeq, MiSeq, Ion PGM and Ion GeneStudio S5.

As used herein, "nucleic acid tag" refers to a short nucleic acid (e.g., less than about 500 nucleotides, about 100 nucleotides, about 50 nucleotides, or about 10 nucleotides in length), used to distinguish nucleic acids from different samples (e.g., representing a sample index), distinguish nucleic acids from different partitions (e.g., representing a partition tag) or different nucleic acid molecules in the same sample (e.g., representing a molecular barcode), of different types, or which have undergone different processing. The nucleic acid tag comprises a predetermined, fixed, non-random, random or semi-random oligonucleotide sequence. Such nucleic acid tags may be used to label different nucleic acid molecules or different nucleic acid samples or subsamples. Nucleic acid tags can be single-stranded, double-stranded, or at least partially double-stranded. Nucleic acid tags optionally have the same length or varied lengths. Nucleic acid tags can also include double-stranded molecules having one or more blunt-ends, include 5' or 3' single-stranded regions (e.g., an overhang), and/or include one or more other single-stranded regions at other locations within a given molecule. Nucleic acid tags can be attached to one end or to both ends of the other nucleic acids (e.g., sample nucleic acids to be amplified and/or sequenced). Nucleic acid tags can be decoded to reveal information such as the sample of origin, form, or processing of a given nucleic acid. For example, nucleic acid tags can also be used to enable pooling and/or parallel processing of multiple samples comprising nucleic acids bearing different molecular barcodes and/or sample indexes in which the nucleic acids are subsequently being deconvolved by detecting (e.g., reading) the nucleic acid tags. Nucleic acid tags can also be referred to as identifiers (e.g. molecular identifier, sample identifier). Additionally, or alternatively, nucleic acid tags can be used as molecular identifiers (e.g., to distinguish between different molecules or amplicons of different parent molecules in the same sample or sub-sample). This includes, for example, uniquely tagging different nucleic acid molecules in a given sample, or non-uniquely tagging such molecules. In the case of non-unique tagging applications, a limited number of tags (i.e., molecular barcodes) may be used to tag each nucleic acid molecule such that different molecules can be distinguished based on their endogenous sequence information (for example, start and/or stop positions where they map to a selected reference genome, a sub-sequence of one or both ends of a sequence, and/or length of a sequence) in combination with at least one molecular barcode. Typically, a sufficient number of different molecular barcodes are used such that there is a low probability (e.g., less than about a 10%, less than about a 5%, less than about a 1%, or less than about a 0.1% chance) that any two molecules may have the same endogenous sequence information (e.g., start and/or stop positions, sub-sequences of one or both ends of a sequence, and/or lengths) and also have the same molecular barcode.

As used herein, "partitioning" refers to physically separating or fractionating a mixture of nucleic acid molecules in a sample based on a characteristic of the nucleic acid molecules. The partitioning can be physical partitioning of molecules. Partitioning can involve separating the nucleic acid molecules into groups or sets based on the level of epigenetic feature (for e.g., methylation). For example, the nucleic acid molecules can be partitioned based on the level of methylation of the nucleic acid molecules. In some embodiments, the methods and systems used for partitioning may be found in PCT Patent Application No. PCT/US2017/068329, which is hereby incorporated by reference in its entirety.

As used herein, "partitioned set" or "partition" refers to a set of nucleic acid molecules partitioned into a set or group based on the differential binding affinity of the nucleic acid molecules or proteins associated with the nucleic acid molecules to a binding agent. A partitioned set may also be referred to as a subsample. The binding agent binds preferentially to the nucleic acid molecules comprising nucleotides with epigenetic modification. For example, if the epigenetic modification is methylation, the binding agent can be a methyl binding domain (MBD) protein. In some embodiments, a partitioned set can comprise nucleic acid molecules belonging to a particular level or degree of epigenetic feature (for e.g., methylation). For example, the nucleic acid molecules can be partitioned into three sets—one set for highly methylated nucleic acid molecules (first subsample, hyper partition, hyper partitioned set or hypermethylated partitioned set), a second set for low methylated nucleic acid molecules (second subsample, hypo partition, hypo partitioned set or hypomethylated partitioned set), and a third set for intermediate methylated nucleic acid molecules (third subsample, intermediate partitioned set, intermediately methylated partitioned set, residual partitioned set, or residual partition). In another example, the nucleic acid molecules can be partitioned based on the number of methylated nucleotides—one partitioned set can have nucleic acid molecules with nine methylated nucleotides, and another partitioned set can have unmethylated nucleic acid molecules (zero methylated nucleotides).

As used herein, "polynucleotide", "nucleic acid", "nucleic acid molecule", or "oligonucleotide" refers to a linear polymer of nucleosides (including deoxyribonucleosides, ribonucleosides, or analogs thereof) joined by inter-nucleosidic linkages. Typically, a polynucleotide comprises at least three nucleosides. Oligonucleotides often range in size from a few monomeric units, e.g., 3-4, to hundreds of monomeric units. Whenever a polynucleotide is represented by a sequence of letters, such as "ATGCCTG", the nucleotides are in 5' 3' order from left to right, and in the case of DNA, "A" denotes deoxyadenosine, "C" denotes deoxycytidine, "G" denotes deoxyguanosine, and "T" denotes deoxythymidine, unless otherwise noted. The letters A, C, G, and T may be used to refer to the bases themselves, to nucleosides, or to nucleotides comprising the bases.

As used herein, "processing" refers to a set of steps used to generate a library of nucleic acids that is suitable for sequencing. The set of steps can include, but are not limited to, partitioning, end repairing, addition of sequencing adapters, tagging, and/or PCR amplification of nucleic acids.

As used herein, "quantitative measure" refers to an absolute or relative measure. A quantitative measure can be, without limitation, a number, a statistical measurement (e.g., frequency, mean, median, standard deviation, or quantile), or a degree or a relative quantity (e.g., high, medium, and low). A quantitative measure can be a ratio of two quantitative measures. A quantitative measure can be a linear combination of quantitative measures. A quantitative measure may be a normalized measure.

As used herein, "reference sequence" refers to a known sequence used for purposes of comparison with experimentally determined sequences. For example, a known sequence can be an entire genome, a chromosome, or any segment thereof. A reference sequence can align with a single contiguous sequence of a genome or chromosome or chromosome arm or can include non-contiguous segments that align with different regions of a genome or chromosome. Examples of reference sequences include, for example, human genomes, such as, hg19 and hg38.

As used herein, "restriction enzyme" is an enzyme that recognizes and cleaves the DNA at or near a specific recognition site.

As used herein, "sample" means anything capable of being analyzed by the methods and/or systems disclosed herein.

As used herein, "sequencing" refers to any of a number of technologies used to determine the sequence (e.g., the identity and order of monomer units) of a biomolecule, e.g., a nucleic acid such as DNA or RNA. Examples of sequencing methods include, but are not limited to, targeted sequencing, single molecule real-time sequencing, exon or exome sequencing, intron sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, and a combination thereof. In some embodiments, sequencing can be performed by a gene analyzer such as, for example, gene analyzers commercially available from Illumina, Inc., Pacific Biosciences, Inc., or Applied Biosystems/Thermo Fisher Scientific, among many others.

As used herein, "sequence information" in the context of a nucleic acid polymer means the order and identity of monomer units (e.g., nucleotides, etc.) in that polymer.

As used herein "sequence-variable target region set" refers to a set of target regions that may exhibit changes in sequence such as nucleotide substitutions, insertions, deletions, or gene fusions or transpositions in neoplastic cells (e.g., tumor cells and cancer cells).

As used herein, the terms "somatic mutation" or "somatic variation" are used interchangeably. They refer to a mutation in the genome that occurs after conception. Somatic mutations can occur in any cell of the body except germ cells and accordingly, are not passed on to progeny.

As used herein, "specifically binds" in the context of an probe or other oligonucleotide and a target sequence means that under appropriate hybridization conditions, the oligonucleotide or probe hybridizes to its target sequence, or replicates thereof, to form a stable probe:target hybrid, while at the same time formation of stable probe:non-target hybrids is minimized. Thus, a probe hybridizes to a target sequence or replicate thereof to a sufficiently greater extent than to a non-target sequence, to enable capture or detection of the target sequence. Appropriate hybridization conditions are well-known in the art, may be predicted based on sequence composition, or can be determined by using routine testing methods (see, e.g., Sambrook et al., Molecular Cloning, A Laboratory Manual, 2nd ed. (Cold Spring Harbor Laboratory Press, Cold Spring Harbor, NY, 1989) at §§ 1.90-1.91, 7.37-7.57, 9.47-9.51 and 11.47-11.57, particularly §§ 9.50-9.51, 11.12-11.13, 11.45-11.47 and 11.55-11.57, incorporated by reference herein).

As used herein, "subject" refers to an animal, such as a mammalian species (e.g., human) or avian (e.g., bird) species, or other organism, such as a plant. More specifically, a subject can be a vertebrate, e.g., a mammal such as a mouse, a primate, a simian or a human. Animals include farm animals (e.g., production cattle, dairy cattle, poultry, horses, pigs, and the like), sport animals, and companion animals (e.g., pets or support animals). A subject can be a healthy individual, an individual that has or is suspected of having a disease or a predisposition to the disease, or an individual in need of therapy or suspected of needing therapy. The terms "individual" or "patient" are intended to be interchangeable with "subject". For example, a subject can be an individual who has been diagnosed with having a cancer, is going to receive a cancer therapy, and/or has received at least one cancer therapy. The subject can be in remission of a cancer. As another example, the subject can be an individual who is diagnosed of having an autoimmune disease. As another example, the subject can be a female individual who is pregnant or who is planning on getting pregnant, who may have been diagnosed of or suspected of having a disease, e.g., a cancer, an auto-immune disease.

As used herein, "target-region set" or "set of target regions" or "target regions" or "target regions of interest" or "regions of interest" or "genomic regions of interest" refers to a plurality of genomic loci or a plurality of genomic regions targeted for capture and/or targeted by a set of probes (e.g., through sequence complementarity).

As used herein, "tumor fraction" refers to the proportion of cfDNA molecules that originated from tumor cells for a given sample, or sample-region pair.

The terms "or a combination thereof" and "or combinations thereof" as used herein refers to any and all permutations and combinations of the listed terms preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

"Or" is used in the inclusive sense, i.e., equivalent to "and/or," unless the context requires otherwise.

B. Exemplary Methods

1. Overview

Cancer formation and progression may arise from both genetic modification and epigenetic features of deoxyribonucleic acid (DNA). The present disclosure provides methods and systems for analyzing DNA, such as cell-free DNA (cfDNA). The present disclosure provides methods and systems for reducing signal to noise ratio of methylation partitioning assays.

Without wishing to be bound by any particular theory, cells in or around a cancer or neoplasm may shed more DNA than cells of the same tissue type in a healthy subject. As such, the distribution of tissue of origin of certain DNA samples, such as cfDNA, may change upon carcinogenesis. Thus, for example, an increase in the level of hypermethylation variable target regions that show lower methylation in healthy cfDNA than in at least one other tissue type can be an indicator of the presence (or recurrence, depending on the history of the subject) of cancer. Similarly, an increase in the level of hypomethylation variable target regions in the sample can be an indicator of the presence (or recurrence, depending on the history of the subject) of cancer.

Additionally, cancer can be indicated by non-sequence modifications, such as methylation. Examples of methylation changes in cancer include local gains of DNA methylation in the CpG islands at the TSS of genes involved in normal growth control, DNA repair, cell cycle regulation, and/or cell differentiation. This hypermethylation can be associated with an aberrant loss of transcriptional capacity of involved genes and occurs at least as frequently as point mutations and deletions as a cause of altered gene expression.

Thus, DNA methylation profiling can be used to detect aberrant methylation in DNA of a sample. The DNA can correspond to certain genomic regions ("differentially methylated regions" or "DMRs") that are normally hypermethylated or hypomethylated in a given sample type (e.g., cfDNA from the bloodstream) but which may show an abnormal degree of methylation that correlates to a neoplasm or cancer, e.g., because of unusually increased contributions of tissues to the type of sample (e.g., due to increased shedding of DNA in or around the neoplasm or cancer) and/or from extents of methylation of the genome that are altered during development or that are perturbed by disease, for example, cancer or any cancer-associated disease.

In some embodiments, DNA methylation comprises addition of a methyl group to a cytosine residue at a CpG site (cytosine-phosphate-guanine site (i.e., a cytosine followed by a guanine in a 5'→3' direction of the nucleic acid sequence). In some embodiments, DNA methylation comprises addition of a methyl group to an adenine residue, such as in N6-methyladenine. In some embodiments, DNA methylation is 5-methylation (modification of the 5th carbon of the 6-carbon ring of cytosine). In some embodiments, 5-methylation comprises addition of a methyl group to the 5C position of the cytosine residue to create 5-methylcytosine (m5c or 5-mC or 5mC). In some embodiments, methylation comprises a derivative of m5c. Derivatives of m5c include, but are not limited to, 5-hydroxymethylcytosine (5-hmC or 5hmC), 5-formylcytosine (5-fC), and 5-caryboxylcytosine (5-caC). In some embodiments, DNA methylation is 3C methylation (modification of the 3rd carbon of the 6-carbon ring of the cytosine residue). In some embodiments, 3C methylation comprises addition of a methyl group to the 3C position of the cytosine residue to generate 3-methylcytosine (3mC). Methylation can also occur at non-CpG sites, for example, methylation can occur at a CpA, CpT, or CpC site. DNA methylation can change the activity of methylated DNA region. For example, when DNA in a promoter region is methylated, transcription of the gene may be repressed. DNA methylation is critical for normal development and abnormality in methylation may disrupt epigenetic regulation. The disruption, e.g., repression, in epigenetic regulation may cause diseases, such as cancer. Promoter methylation in DNA may be indicative of cancer.

Methylation profiling can involve determining methylation patterns across different regions of the genome. For example, after partitioning molecules based on extent of methylation (e.g., relative number of methylated nucleotides per molecule) and sequencing, the sequences of molecules in the different partitions can be mapped to a reference genome. This can show regions of the genome that, compared with other regions, are more highly methylated or are less highly methylated. In this way, genomic regions, in contrast to individual molecules, may differ in their extent of methylation.

In some embodiments, combining the signals obtained from methylation profiling with the signals obtained from somatic variations (e.g., SNV, indel, CNV, and gene fusions) facilitates the detection of cancer.

Nucleic acid molecules in a sample may be fractionated or partitioned based on methylation status of the nucleic acid molecules. Partitioning nucleic acid molecules in a sample can increase a rare signal. For example, a genetic variation present in hypermethylated DNA but less (or not) present in hypomethylated DNA can be more easily detected by partitioning a sample into hypermethylated and hypomethylated nucleic acid molecules. By analyzing multiple fractions of a sample, a multi-dimensional analysis of a single molecule can be performed and hence, greater sensitivity can be achieved. Partitioning may include physically partitioning nucleic acid molecules into subsets or groups based on the presence or absence of one ore more methylated nucleotides. A sample may be fractionated or partitioned into one or more partitioned sets based on a characteristic that is indicative of differential gene expression or a disease state. A sample may be fractionated based on a characteristic, or combination thereof that provides a difference in signal between a normal and diseased state during analysis of nucleic acids, e.g., cell free DNA ("cfDNA"), non-cfDNA, tumor DNA, circulating tumor DNA ("ctDNA") and cell free nucleic acids ("cfNA").

Partitioning procedures may result in imperfect sorting of DNA molecules among the subsamples. For example, a minority of the molecules in the second subsample may be highly modified (e.g., hypermethylated), and/or a minority of the molecules in the first subsample may be unmodified or mostly unmodified (e.g., unmethylated or mostly unmethylated). Highly modified molecules in the second subsample and unmodified or mostly unmodified molecules in the first subsample are considered nonspecifically partitioned. The methods described herein comprise steps that can reduce technical noise from nonspecifically partitioned DNA, e.g., by converting certain bases such that nonspecifically partitioned DNA can be identified following sequencing and/or by degrading it. Thus, the methods described herein can provide improved sensitivity and/or streamlined analysis.

FIG. 1 illustrates an exemplary workflow, e.g., to detect the presence or absence of cancer, according to certain embodiments of the disclosure beginning with a cfDNA sample, in which cfDNA is isolated from the blood sample and the cfDNA sample comprises cfDNA molecules belonging to hypermethylation variable target regions (Hyper DMR) and hypomethylation variable target regions (Hypo DMR) and unmethylated control regions. The cfDNA is partitioned using a methyl-binding domain protein (MBD) into hypo methylated and hyper methylated subsamples; each subsample is subjected to molecular barcoding to distinguishably tag DNA from the subsamples; the hypo subsample and optionally the hyper subsample is subjected to a conversion procedure, facilitating identification of non-specifically partitioned molecules; and then partitioned sets are pooled, captured, amplified, and sequenced. The conversion procedure used with the hypo subsample can be a conversion procedure that changes the base pairing specificity of mC, but does not affect unmethylated C, such as TAP. When used, the conversion procedure for the hyper sample can be a conversion procedure that changes the base pairing specificity of C, but does not affect mC, such as EM.

Figure 2:
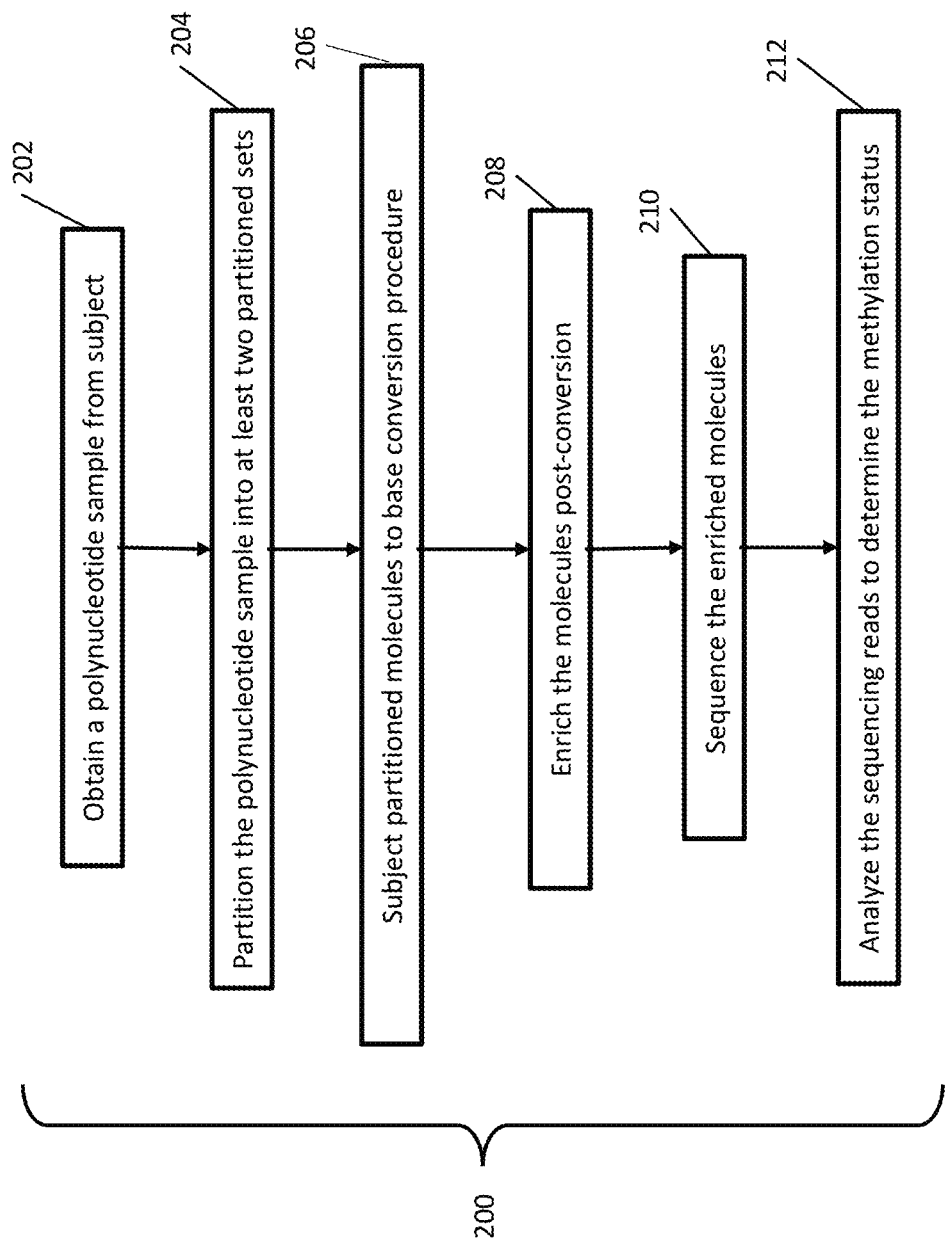
FIG. 2 is a flow chart representation of a method for determining the methylation status of nucleic acid molecules in a polynucleotide sample obtained from a subject according to an embodiment of the disclosure.

FIG. 2 illustrates an example embodiment of a method 200 for determining the methylation status of nucleic acid molecules in a sample obtained from a subject. In 202, a polynucleotide sample is obtained from the subject. In some embodiments, the sample is a DNA sample obtained from a tumor tissue biopsy. In some embodiments, the sample is a cell-free DNA (cfDNA) sample obtained from blood. In 204, the polynucleotides sample is partitioned into at least two partitioned sets (subsamples). In some embodiments, the partitioning comprises partitioning the nucleic acid molecules based on a differential binding affinity of the polynucleotides to a binding agent that preferentially binds to polynucleotides comprising methylated nucleotides.

In 206, the nucleic acid molecules in at least one partitioned set such as the second subsample (hypomethylated partition) is subjected to a base conversion procedure, i.e., a procedure that affects a first nucleobase in the DNA differently from a second nucleobase in the DNA of the second subsample, wherein the first nucleobase is a modified or unmodified nucleobase, the second nucleobase is a modified or unmodified nucleobase different from the first nucleobase, and the first nucleobase and the second nucleobase have the same base pairing specificity, thereby producing a treated subsample. Various conversion procedures are described herein. In some embodiments, the conversion procedure converts methylated cytosine to a different nucleobase. Where the first and second subsamples are subjected to a conversion procedure, the procedure may be the same or different. In some embodiments, the first subsample is subjected to a procedure that converts methylated cytosine to a different nucleobase and the second subsample is subjected to a procedure that converts unmethylated cytosine to a different nucleobase.

In some embodiments, prior to conversion, at least one adapter is attached to at least one end of the nucleic acid molecules (i.e., 5' and/or 3' ends of the DNA molecule). In other embodiments, after the digestion but prior to enriching in 208, at least one adapter is attached to at least one end of the nucleic acid molecules. In some embodiments, the adapter is resistant to conversion by the conversion procedure, e.g., due to the presence of unmethylated nucleotides or appropriate nucleotide analogs.

In 208, after conversion, the nucleic acid molecules in the one or more partitioned sets can be enriched for genomic regions of interest. Alternatively, an enrichment step can be performed before the partitioning step. In some embodiments, the genomic regions of interest can comprise differentially methylated regions (e.g., a hypermethylation variable target region set and/or hypomethylation variable target region set) for cancer detection. In 210, at least a subset of the enriched molecules is sequenced by a next generation sequencer. In 212, the sequencing reads generated by the sequencer are then analyzed using bioinformatic tools/algorithms to determine the number of molecules in the one or more partitioned sets, which in turn is used to determine the methylation status at one or more genetic loci of the nucleic acid molecules in at least one partitioned sets. In some embodiments, the one or more genetic loci can comprise multiple genetic loci. In some embodiments, the one or more genetic loci can comprise one or more genomic regions. In some embodiments, the genomic regions can be promoter region of genes. In some embodiments, prior to sequencing, the nucleic acid molecules can be amplified via PCR amplification. In some embodiments, the primers used in the amplification can comprise at least one sample index.

Figure 3:
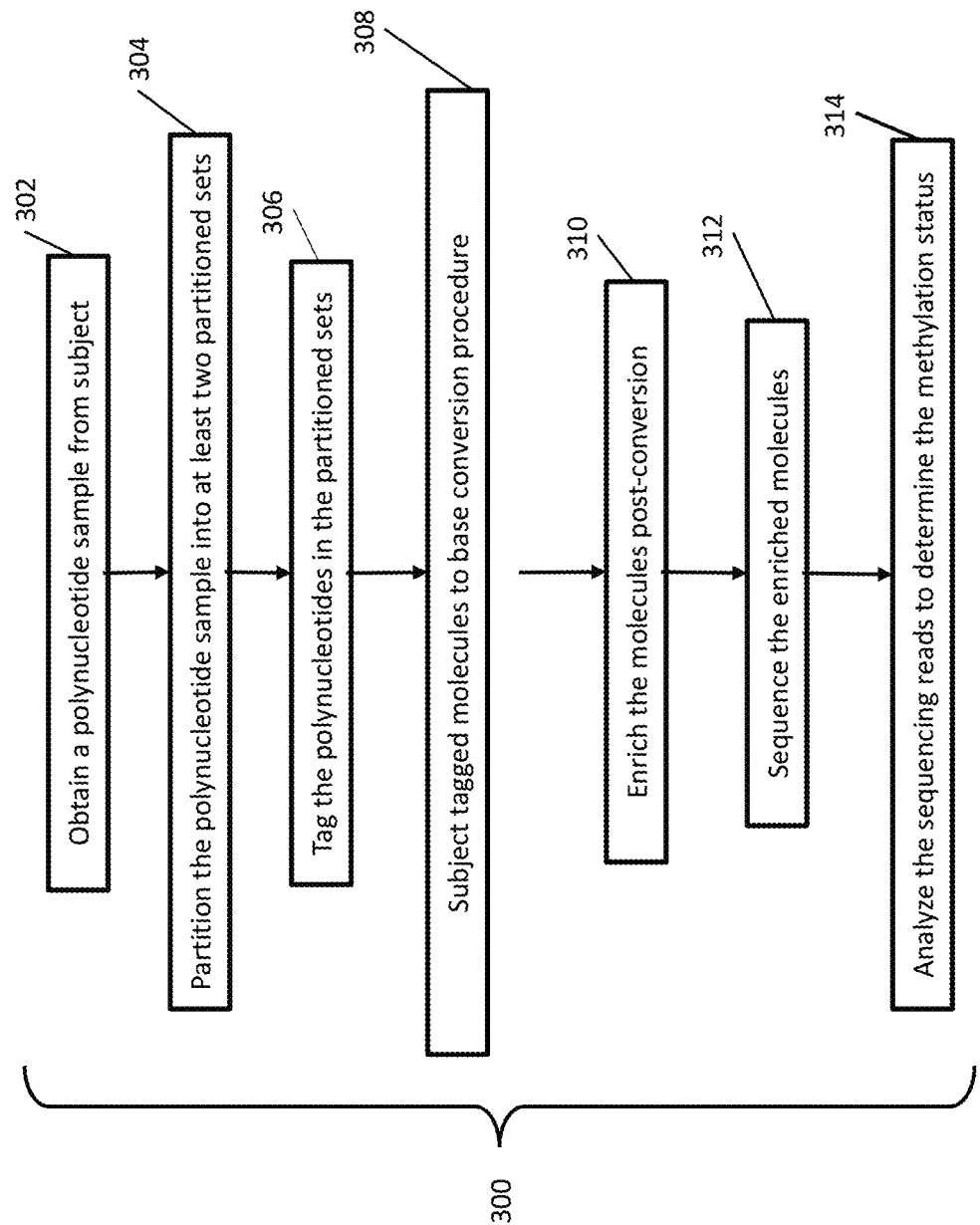
FIG. 3 is a flow chart representation of a method for determining the methylation status of nucleic acid molecules in a polynucleotide sample obtained from a subject according to an embodiment of the disclosure.

FIG. 3 illustrates an example embodiment of a method 300 for determining the methylation status of nucleic acid molecules in sample obtained from a subject according to an embodiment of the disclosure. In 302, a polynucleotide sample is obtained from the subject. In some embodiments, the polynucleotide sample is a DNA sample is obtained from a tumor tissue biopsy. In some embodiments, the polynucleotides sample is a cell-free DNA (cfDNA) sample obtained from blood. In 304, the polynucleotide sample is partitioned into at least two partitioned sets. In some embodiments, the partitioning comprises partitioning the nucleic acid molecules based on a differential binding affinity of the polynucleotides to a binding agent that preferentially binds to polynucleotides comprising methylated nucleotides. Examples of binding agents include, but are not limited to, methyl binding domain (MBDs) methyl binding proteins (MBPs), and antibodies to methylated nucleotides, which are discussed in detail elsewhere herein.

In 306, the nucleic acid molecules in the one or more partitioned sets are attached to adapters, wherein the adapter comprises at least one tag and is attached to at least one end of the nucleic acid molecules (i.e., 5' and/or 3' ends of the DNA molecule). In some embodiments, the tags may be provided as components of adapters. In some embodiments, the tag comprises molecular barcode (i.e., molecule identifier). In some embodiments, the tag attached to nucleic acid molecules in one partitioned set is different from the tag attached to nucleic acid molecules in the other partitioned set(s). In some embodiments, one partitioned set is differentially tagged from the other partitioned set(s). Differential tagging of the partitioned sets helps in keeping track of the nucleic acid molecules belonging to a particular partitioned set. The nucleic acid molecules in different partitioned sets receive different tags that can distinguish members of one partitioned set from another. The tags linked to nucleic acid molecules of the same partition set can be the same or different from one another. But if different from one another, the tags can have part of their sequence in common so as to identify the molecules to which they are attached as being of a particular partitioned set. For example, if the molecules of the sample are partitioned into two partitioned sets—P1 and P2, then the molecules in P1 can be tagged with A1, A2, A3, and so forth, and the molecules in P2 can be tagged with B1, B2, B3, and so forth. Such a tagging system allows distinguishing the partitioned sets and between the molecules within a partitioned set. In some embodiments, the tag comprises a partition tag (i.e., partition identifier). In such embodiments, the nucleic acid molecules within a partitioned set receive the same partition tag, which is different from the partition tag attached to the nucleic acid molecules of the other partitioned set(s).

In 308, the nucleic acid molecules in at least one partitioned set such as the second subsample (hypomethylated partition) are subjected to a base conversion procedure, i.e., a procedure that affects a first nucleobase in the DNA differently from a second nucleobase in the DNA of the second subsample, wherein the first nucleobase is a modified or unmodified nucleobase, the second nucleobase is a modified or unmodified nucleobase different from the first nucleobase, and the first nucleobase and the second nucleobase have the same base pairing specificity, thereby producing a treated subsample. Various conversion procedures are described herein. In some embodiments, the conversion procedure converts methylated cytosine to a different nucleobase. Where the first and second subsamples are subjected to a conversion procedure, the procedure may be the same or different. In some embodiments, the first subsample is subjected to a procedure that converts methylated cytosine to a different nucleobase and the second subsample is subjected to a procedure that converts unmethylated cytosine to a different nucleobase.

In some embodiments, the adapter is resistant to conversion by the base conversion procedure. In some embodiments, the adapters attached to the second subsample comprise or consist of unmethylated nucleotides. In some embodiments, the adapters attached to the first subsample comprise methylated nucleotides. In some embodiments, the adapter comprises one or more nucleotide analogs resistant to methylation dependent restriction enzymes.

In 310, after conversion, the nucleic acid molecules in the one or more partitioned sets can be enriched for genomic regions of interest. Alternatively, an enrichment step can be performed before the partitioning step. In some embodiments, the genomic regions of interest can comprise differentially methylated regions for cancer detection. In 312, at least a subset of the enriched molecules is sequenced by a next generation sequencer. In 314, the sequencing reads generated by the sequencer are then analyzed using bioinformatic tools/algorithms to determine the number of molecules in the one or more partitioned sets, which in turn is used to determine the methylation status at one or more genetic loci of the nucleic acid molecules in at least one partitioned sets. In some embodiments, the one or more genetic loci can comprise multiple genetic loci. In some embodiments, the one or more genetic loci can comprise one or more genomic regions. In some embodiments, the genomic regions can be promoter regions of genes. In some embodiments, prior to sequencing, the nucleic acid molecules can be amplified via PCR amplification. In some embodiments, the primers used in the amplification can comprise at least one sample index.

In some embodiments, the method can further comprise detecting the presence or absence of cancer in the subject, e.g., based on the methylation status at one or more genetic loci of the nucleic acid molecules in at least one partitioned set. In some embodiments, the method further comprises determining a level of DNA from tumor cells in the polynucleotide sample.

2. Partitioning the Sample into a Plurality of Subsamples; Aspects of Samples

In certain embodiments described herein, a population of different forms of nucleic acids (e.g., hypermethylated and hypomethylated DNA in a sample, such as cfDNA) can be physically partitioned based on one or more characteristics of the nucleic acids prior to further analysis, e.g., contacting with a nuclease, differentially modifying or isolating a nucleobase, tagging, and/or sequencing. This approach can be used to determine, for example, whether certain sequences are hypermethylated or hypomethylated. Additionally, by partitioning a heterogeneous nucleic acid population, one may increase rare signals, e.g., by enriching rare nucleic acid molecules that are more prevalent in one fraction (or partition) of the population. For example, a genetic variation present in hyper-methylated DNA but less (or not) in hypomethylated DNA can be more easily detected by partitioning a sample into hyper-methylated and hypomethylated nucleic acid molecules. By analyzing multiple fractions of a sample, a multi-dimensional analysis of a single locus of a genome or species of nucleic acid can be performed and hence, greater sensitivity can be achieved.

In some instances, a heterogeneous nucleic acid sample is partitioned into two or more partitions (e.g., at least 3, 4, 5, 6 or 7 partitions). Partitions of a sample are also referred to herein as subsamples. In some embodiments, each partition is differentially tagged. Tagged partitions can then be pooled together for collective sample prep and/or sequencing. The partitioning-tagging-pooling steps can occur more than once, with each round of partitioning occurring based on a different characteristics (examples provided herein), and tagged using differential tags that are distinguished from other partitions and partitioning means.

Examples of characteristics that can be used for partitioning include sequence length, methylation level, nucleosome binding, sequence mismatch, immunoprecipitation, and/or proteins that bind to DNA. Resulting partitions can include one or more of the following nucleic acid forms: single-stranded DNA (ssDNA), double-stranded DNA (dsDNA), shorter DNA fragments and longer DNA fragments. In some embodiments, partitioning based on a cytosine modification (e.g., cytosine methylation) or methylation generally is performed and is optionally combined with at least one additional partitioning step, which may be based on any of the foregoing characteristics or forms of DNA. In some embodiments, a heterogeneous population of nucleic acids is partitioned into nucleic acids with one or more epigenetic modifications and without the one or more epigenetic modifications. Examples of epigenetic modifications include presence or absence of methylation; level of methylation; type of methylation (e.g., 5-methylcytosine versus other types of methylation, such as adenine methylation and/or cytosine hydroxymethylation); and association and level of association with one or more proteins, such as histones. Alternatively or additionally, a heterogeneous population of nucleic acids can be partitioned into nucleic acid molecules associated with nucleosomes and nucleic acid molecules devoid of nucleosomes. Alternatively or additionally, a heterogeneous population of nucleic acids may be partitioned into single-stranded DNA (ssDNA) and double-stranded DNA (dsDNA). Alternatively, or additionally, a heterogeneous population of nucleic acids may be partitioned based on nucleic acid length (e.g., molecules of up to 160 bp and molecules having a length of greater than 160 bp).

In some instances, each partition (representative of a different nucleic acid form) is differentially labelled, and the partitions are pooled together prior to sequencing. In other instances, the different forms are separately sequenced.

In some embodiments, a population of different nucleic acids is partitioned into two or more different partitions. Each partition is representative of a different nucleic acid form, and a first partition (also referred to as a subsample) comprises DNA with a cytosine modification in a greater proportion than a second subsample. Each partition is distinctly tagged. The first subsample is subjected to a procedure that affects a first nucleobase in the DNA differently from a second nucleobase in the DNA of the first subsample, wherein the first nucleobase is a modified or unmodified nucleobase, the second nucleobase is a modified or unmodified nucleobase different from the first nucleobase, and the first nucleobase and the second nucleobase have the same base pairing specificity. The tagged nucleic acids are pooled together prior to sequencing. Sequence reads are obtained and analyzed, including to distinguish the first nucleobase from the second nucleobase in the DNA of the first subsample, in silico. Tags are used to sort reads from different partitions. Analysis to detect genetic variants can be performed on a partition-by-partition level, as well as whole nucleic acid population level. For example, analysis can include in silico analysis to determine genetic variants, such as CNV, SNV, indel, fusion in nucleic acids in each partition. In some instances, in silico analysis can include determining chromatin structure. For example, coverage of sequence reads can be used to determine nucleosome positioning in chromatin. Higher coverage can correlate with higher nucleosome occupancy in genomic region while lower coverage can correlate with lower nucleosome occupancy or nucleosome depleted region (NDR).

Samples can include nucleic acids varying in modifications including post-replication modifications to nucleotides and binding, usually noncovalently, to one or more proteins.

In an embodiment, the population of nucleic acids is one obtained from a serum, plasma or blood sample from a subject suspected of having neoplasia, a tumor, or cancer or previously diagnosed with neoplasia, a tumor, or cancer. The population of nucleic acids includes nucleic acids having varying levels of methylation. Methylation can occur from any one or more post-replication or transcriptional modifications. Post-replication modifications include modifications of the nucleotide cytosine, particularly at the 5-position of the nucleobase, e.g., 5-methylcytosine, 5-hydroxymethylcytosine, 5-formylcytosine and 5-carboxylcytosine.

The affinity agents can be antibodies with the desired specificity, natural binding partners or variants thereof (Bock et al., Nat Biotech 28: 1106-1114 (2010); Song et al., Nat Biotech 29: 68-72 (2011)), or artificial peptides selected e.g., by phage display to have specificity to a given target.

Examples of capture moieties contemplated herein include methyl binding domain (MBDs) and methyl binding proteins (MBPs) as described herein, including proteins such as MeCP2, an MBD such as MBD2, and antibodies preferentially binding to 5-methylcytosine. Where an antibody is used to immunoprecipitate methylated DNA, the methylated DNA may be recovered in single-stranded form. In such embodiments, a second strand can be synthesized. Hypermethylated (and optionally intermediately methylated) subsamples may then be contacted with a methylation sensitive nuclease that does not cleave hemi-methylated DNA, such as HpaII, BstUI, or Hin6i. Alternatively or in addition, hypomethylated (and optionally intermediately methylated) subsamples may then be contacted with a methylation dependent nuclease that cleaves hemi-methylated DNA.

Likewise, partitioning of different forms of nucleic acids can be performed using histone binding proteins which can separate nucleic acids bound to histones from free or unbound nucleic acids. Examples of histone binding proteins that can be used in the methods disclosed herein include RBBP4, RbAp48 and SANT domain peptides.

Although for some affinity agents and modifications, binding to the agent may occur in an essentially all or none manner depending on whether a nucleic acid bears a modification, the separation may be one of degree. In such instances, nucleic acids overrepresented in a modification bind to the agent at a greater extent that nucleic acids underrepresented in the modification. Alternatively, nucleic acids having modifications may bind in an all or nothing manner. But then, various levels of modifications may be sequentially eluted from the binding agent.

For example, in some embodiments, partitioning can be binary or based on degree/level of modifications. For example, all methylated fragments can be partitioned from unmethylated fragments using methyl-binding domain proteins (e.g., MethylMinder Methylated DNA Enrichment Kit (ThermoFisher Scientific). Subsequently, additional partitioning may involve eluting fragments having different levels of methylation by adjusting the salt concentration in a solution with the methyl-binding domain and bound fragments. As salt concentration increases, fragments having greater methylation levels are eluted.

In some instances, the final partitions are representative of nucleic acids having different extents of modifications (overrepresentative or underrepresentative of modifications). Overrepresentation and underrepresentation can be defined by the number of modifications born by a nucleic acid relative to the median number of modifications per strand in a population. For example, if the median number of 5-methylcytosine residues in nucleic acid in a sample is 2, a nucleic acid including more than two 5-methylcytosine residues is overrepresented in this modification and a nucleic acid with 1 or zero 5-methylcytosine residues is underrepresented. The effect of the affinity separation is to enrich for nucleic acids overrepresented in a modification in a bound phase and for nucleic acids underrepresented in a modification in an unbound phase (i.e. in solution). The nucleic acids in the bound phase can be eluted before subsequent processing.

When using MethylMiner Methylated DNA Enrichment Kit (ThermoFisher Scientific) various levels of methylation can be partitioned using sequential elutions. For example, a hypomethylated partition (no methylation) can be separated from a methylated partition by contacting the nucleic acid population with the MBD from the kit, which is attached to magnetic beads. The beads are used to separate out the methylated nucleic acids from the non-methylated nucleic acids. Subsequently, one or more elution steps are performed sequentially to elute nucleic acids having different levels of methylation. For example, a first set of methylated nucleic acids can be eluted at a salt concentration of 160 mM or higher, e.g., at least 150 mM, at least 200 mM, 300 mM, 400 mM, 500 mM, 600 mM, 700 mM, 800 mM, 900 mM, 1000 mM, or 2000 mM. After such methylated nucleic acids are eluted, magnetic separation is once again used to separate higher level of methylated nucleic acids from those with lower level of methylation. The elution and magnetic separation steps can repeat themselves to create various partitions such as a hypomethylated partition (representative of no methylation), a methylated partition (representative of low level of methylation), and a hyper methylated partition (representative of high level of methylation).

In some methods, nucleic acids bound to an agent used for affinity separation are subjected to a wash step. The wash step washes off nucleic acids weakly bound to the affinity agent. Such nucleic acids can be enriched in nucleic acids having the modification to an extent close to the mean or median (i.e., intermediate between nucleic acids remaining bound to the solid phase and nucleic acids not binding to the solid phase on initial contacting of the sample with the agent).

The affinity separation results in at least two, and sometimes three or more partitions of nucleic acids with different extents of a modification. While the partitions are still separate, the nucleic acids of at least one partition, and usually two or three (or more) partitions are linked to nucleic acid tags, usually provided as components of adapters, with the nucleic acids in different partitions receiving different tags that distinguish members of one partition from another. The tags linked to nucleic acid molecules of the same partition can be the same or different from one another. But if different from one another, the tags may have part of their code in common so as to identify the molecules to which they are attached as being of a particular partition.

For further details regarding partitioning nucleic acid samples based on characteristics such as methylation, see WO2018/119452, which is incorporated herein by reference.

In some embodiments, the nucleic acid molecules can be partitioned into different partitions based on the nucleic acid molecules that are bound to a specific protein or a fragment thereof and those that are not bound to that specific protein or fragment thereof.

Nucleic acid molecules can be partitioned based on DNA-protein binding. Protein-DNA complexes can be partitioned based on a specific property of a protein. Examples of such properties include various epitopes, modifications (e.g., histone methylation or acetylation) or enzymatic activity. Examples of proteins which may bind to DNA and serve as a basis for fractionation may include, but are not limited to, protein A and protein G. Any suitable method can be used to partition the nucleic acid molecules based on protein bound regions. Examples of methods used to partition nucleic acid molecules based on protein bound regions include, but are not limited to, SDS-PAGE, chromatin-immuno-precipitation (ChIP), heparin chromatography, and asymmetrical field flow fractionation (AF4).

In some embodiments, partitioning of the nucleic acids is performed by contacting the nucleic acids with a methylation binding domain ("MBD") of a methylation binding protein ("MBP"). MBD binds to 5-methylcytosine (5mC). MBD is coupled to paramagnetic beads, such as Dynabeads® M-280 Streptavidin via a biotin linker. Partitioning into fractions with different extents of methylation can be performed by eluting fractions by increasing the NaCl concentration.

Examples of MBPs contemplated herein include, but are not limited to:
(a) MeCP2 and MBD2 are proteins preferentially binding to 5-methyl-cytosine over unmodified cytosine.
(b) RPL26, PRP8 and the DNA mismatch repair protein MHS6 preferentially bind to 5-hydroxymethyl-cytosine over unmodified cytosine.
(c) FOXK1, FOXK2, FOXP1, FOXP4 and FOXI3 preferably bind to 5-formyl-cytosine over unmodified cytosine (Iurlaro et al., Genome Biol. 14: R119 (2013)).
(d) Antibodies specific to one or more methylated nucleotide bases (e.g., MeDIP).

In some embodiments, partitioning comprises methylated DNA immunoprecipitation. For example, partitioning by methylated DNA immunoprecipitation may be used in methods where a target region set is captured before the partitioning occurs.

In general, elution is a function of number of methylated sites per molecule, with molecules having more methylation eluting under increased salt concentrations. To elute the DNA into distinct populations based on the extent of methylation, one can use a series of elution buffers of increasing NaCl concentration. Salt concentration can range from about 100 nm to about 2500 mM NaCl. In one embodiment, the process results in three (3) partitions. Molecules are contacted with a solution at a first salt concentration and comprising a molecule comprising a methyl binding domain, which molecule can be attached to a capture moiety, such as streptavidin. At the first salt concentration a population of molecules will bind to the MBD and a population will remain unbound. The unbound population can be separated as a "hypomethylated" population. For example, a first partition representative of the hypomethylated form of DNA is that which remains unbound at a low salt concentration, e.g., 100 mM or 160 mM. A second partition representative of intermediate methylated DNA is eluted using an intermediate salt concentration, e.g., between 100 mM and 2000 mM concentration. This is also separated from the sample. A third partition representative of hypermethylated form of DNA is eluted using a high salt concentration, e.g., at least about 2000 mM.

a. Tagging of Partitions

In some embodiments, two or more partitions, e.g., each partition, is/are differentially tagged. Tags or indexes can be molecules, such as nucleic acids, containing information that indicates a feature of the molecule with which the tag is associated. Tags can allow one to differentiate molecules from which sequence reads originated. For example, molecules can bear a sample tag or sample index (which distinguishes molecules in one sample from those in a different sample), a partition tag (which distinguishes molecules in one partition from those in a different partition) or a molecular tag/molecular barcode/barcode (which distinguishes different molecules from one another (in both unique and non-unique tagging scenarios). In certain embodiments, a tag can comprise one or a combination of barcodes. As used herein, the term "barcode" refers to a nucleic acid molecule having a particular nucleotide sequence, or to the nucleotide sequence, itself, depending on context. A barcode can have, for example, between 10 and 100 nucleotides. A collection of barcodes can have degenerate sequences or can have sequences having a certain hamming distance, as desired for the specific purpose. So, for example, a molecular barcode can be comprised of one barcode or a combination of two barcodes, each attached to different ends of a molecule. Additionally or alternatively, for different partitions and/or samples, different sets of molecular barcodes, molecular tags, or molecular indexes can be used such that the barcodes serve as a molecular tag through their individual sequences and also serve to identify the partition and/or sample to which they correspond based the set of which they are a member. Tags comprising barcodes can be incorporated into or otherwise joined to adapters. Tags can be incorporated by ligation, overlap extension PCR among other methods.

Tagging strategies can be divided into unique tagging and non-unique tagging strategies. In unique tagging, all or substantially all of the molecules in a sample bear a different tag, so that reads can be assigned to original molecules based on tag information alone. Tags used in such methods are sometimes referred to as "unique tags". In non-unique tagging, different molecules in the same sample can bear the same tag, so that other information in addition to tag information is used to assign a sequence read to an original molecule. Such information may include start and stop coordinate, coordinate to which the molecule maps, start or stop coordinate alone, etc. Tags used in such methods are sometimes referred to as "non-unique tags". Accordingly, it is not necessary to uniquely tag every molecule in a sample. It suffices to uniquely tag molecules falling within an identifiable class within a sample. Thus, molecules in different identifiable families can bear the same tag without loss of information about the identity of the tagged molecule.

In certain embodiments of non-unique tagging, the number of different tags used can be sufficient that there is a very high likelihood (e.g., at least 99%, at least 99.9%, at least 99.99% or at least 99.999% that all molecules of a particular group bear a different tag. It is to be noted that when barcodes are used as tags, and when barcodes are attached, e.g., randomly, to both ends of a molecule, the combination of barcodes, together, can constitute a tag. This number, in term, is a function of the number of molecules falling into the calls. For example, the class may be all molecules mapping to the same start-stop position on a reference genome. The class may be all molecules mapping across a particular genetic locus, e.g., a particular base or a particular region (e.g., up to 100 bases or a gene or an exon of a gene). In certain embodiments, the number of different tags used to uniquely identify a number of molecules, z, in a class can be between any of $2*z$, $3*z$, $4*z$, $5*z$, $6*z$, $7*z$, $8*z$, $9*z$, $10*z$, $11*z$, $12*z$, $13*z$, $14*z$, $15*z$, $16*z$, $17*z$, $18*z$, $19*z$, $20*z$ or $100*z$ (e.g., lower limit) and any of $100,000*z$, $10,000*z$, $1000*z$ or $100*z$ (e.g., upper limit).

For example, in a sample of about 5 ng to 30 ng of cell free DNA, one expects around 3000 molecules to map to a particular nucleotide coordinate, and between about 3 and 10 molecules having any start coordinate to share the same stop coordinate. Accordingly, about 50 to about 50,000 different tags (e.g., between about 6 and 220 barcode combinations) can suffice to uniquely tag all such molecules. To uniquely tag all 3000 molecules mapping across a nucleotide coordinate, about 1 million to about 20 million different tags would be required.

Generally, assignment of unique or non-unique tags barcodes in reactions follows methods and systems described by US patent applications 20010053519, 20030152490, 20110160078, and U.S. Pat. Nos. 6,582,908 and 7,537,898 and 9,598,731. Tags can be linked to sample nucleic acids randomly or non-randomly.

In some embodiments, the tagged nucleic acids are sequenced after loading into a microwell plate. The microwell plate can have 96, 384, or 1536 microwells. In some cases, they are introduced at an expected ratio of unique tags to microwells. For example, the unique tags may be loaded so that more than about 1, 2, 3, 4, 5, 6, 7, 8, 9, 10, 20, 50, 100, 500, 1000, 5000, 10000, 50,000, 100,000, 500,000, 1,000,000, 10,000,000, 50,000,000 or 1,000,000,000 unique tags are loaded per genome sample. In some cases, the unique tags may be loaded so that less than about 2, 3, 4, 5, 6, 7, 8, 9, 10, 20, 50, 100, 500, 1000, 5000, 10000, 50,000, 100,000, 500,000, 1,000,000, 10,000,000, 50,000,000 or 1,000,000,000 unique tags are loaded per genome sample. In some cases, the average number of unique tags loaded per sample genome is less than, or greater than, about 1, 2, 3, 4, 5, 6, 7, 8, 9, 10, 20, 50, 100, 500, 1000, 5000, 10000, 50,000, 100,000, 500,000, 1,000,000, 10,000,000, 50,000,000 or 1,000,000,000 unique tags per genome sample.

A preferred format uses 20-50 different tags (e.g., barcodes) ligated to both ends of target nucleic acids. For example 35 different tags (e.g., barcodes) ligated to both ends of target molecules creating 35×35 permutations, which equals 1225 for 35 tags. Such numbers of tags are sufficient so that different molecules having the same start and stop points have a high probability (e.g., at least 94%, 99.5%, 99.99%, 99.999%) of receiving different combinations of tags. Other barcode combinations include any number between 10 and 500, e.g., about 15×15, about 35×35, about 75×75, about 100×100, about 250×250, about 500×500.

In some cases, unique tags may be predetermined or random or semi-random sequence oligonucleotides. In other cases, a plurality of barcodes may be used such that barcodes are not necessarily unique to one another in the plurality. In this example, barcodes may be ligated to individual molecules such that the combination of the barcode and the sequence it may be ligated to creates a unique sequence that may be individually tracked. As described herein, detection of non-unique barcodes in combination with sequence data of beginning (start) and end (stop) portions of sequence reads may allow assignment of a unique identity to a particular molecule. The length or number of base pairs, of an individual sequence read may also be used to assign a unique identity to such a molecule. As described herein, fragments from a single strand of nucleic acid having been assigned a unique identity, may thereby permit subsequent identification of fragments from the parent strand.

Tags can be used to label the individual polynucleotide population partitions so as to correlate the tag (or tags) with a specific partition. Alternatively, tags can be used in embodiments of the invention that do not employ a partitioning step. In some embodiments, a single tag can be used to label a specific partition. In some embodiments, multiple different tags can be used to label a specific partition. In embodiments employing multiple different tags to label a specific partition, the set of tags used to label one partition can be readily differentiated for the set of tags used to label other partitions. In some embodiments, the tags may have additional functions, for example the tags can be used to index sample sources or used as unique molecular identifiers (which can be used to improve the quality of sequencing data by differentiating sequencing errors from mutations, for example as in Kinde et al., Proc Nat'l Acad Sci USA 108: 9530-9535 (2011), Kou et al., *PLoS ONE*, 11: e0146638 (2016)) or used as non-unique molecule identifiers, for example as described in U.S. Pat. No. 9,598,731. Similarly, in some embodiments, the tags may have additional functions, for example the tags can be used to index sample sources or used as non-unique molecular identifiers (which can be used to improve the quality of sequencing data by differentiating sequencing errors from mutations).

In one embodiment, partition tagging comprises tagging molecules in each partition with a partition tag. After re-combining partitions (e.g., to reduce the number of sequencing runs needed and avoid unnecessary cost) and sequencing molecules, the partition tags identify the source partition. In another embodiment, different partitions are tagged with different sets of molecular tags, e.g., comprised of a pair of barcodes. In this way, each molecular barcode indicates the source partition as well as being useful to distinguish molecules within a partition. For example, a first set of 35 barcodes can be used to tag molecules in a first partition, while a second set of 35 barcodes can be used tag molecules in a second partition.

In some embodiments, after partitioning and tagging with partition tags, the molecules may be pooled for sequencing in a single run. In some embodiments, a sample tag is added to the molecules, e.g., in a step subsequent to addition of partition tags and pooling. Sample tags can facilitate pooling material generated from multiple samples for sequencing in a single sequencing run.

Alternatively, in some embodiments, partition tags may be correlated to the sample as well as the partition. As a simple example, a first tag can indicate a first partition of a first sample; a second tag can indicate a second partition of the first sample; a third tag can indicate a first partition of a second sample; and a fourth tag can indicate a second partition of the second sample.

While tags may be attached to molecules already partitioned based on one or more characteristics, the final tagged molecules in the library may no longer possess that characteristic. For example, while single stranded DNA molecules may be partitioned and tagged, the final tagged molecules in the library are likely to be double stranded. Similarly, while DNA may be subject to partition based on different levels of methylation, in the final library, tagged molecules derived from these molecules are likely to be unmethylated. Accordingly, the tag attached to molecule in the library typically indicates the characteristic of the "parent molecule" from which the ultimate tagged molecule is derived, not necessarily to characteristic of the tagged molecule, itself.

As an example, barcodes 1, 2, 3, 4, etc. are used to tag and label molecules in the first partition; barcodes A, B, C, D, etc. are used to tag and label molecules in the second partition; and barcodes a, b, c, d, etc. are used to tag and label molecules in the third partition. Differentially tagged partitions can be pooled prior to sequencing. Differentially tagged partitions can be separately sequenced or sequenced together concurrently, e.g., in the same flow cell of an Illumina sequencer.

After sequencing, analysis of reads to detect genetic variants can be performed on a partition-by-partition level, as well as a whole nucleic acid population level. Tags are used to sort reads from different partitions. Analysis can include in silico analysis to determine genetic and epigenetic variation (one or more of methylation, chromatin structure, etc.) using sequence information, genomic coordinates length, coverage, and/or copy number. In some embodiments, higher coverage can correlate with higher nucleosome occupancy in genomic region while lower coverage can correlate with lower nucleosome occupancy or a nucleosome depleted region (NDR).

In some embodiments, adapters are used that do not comprise a sequence recognized by nucleases used in the method, and/or are resistant to cleavage, e.g., because of the presence of nucleotide modifications such as linkage modifications (e.g., phosphorothioate). In some embodiments, tags are used that do not comprise a sequence recognized by nucleases used in the method, and/or are resistant to cleavage, e.g., because of the presence of nucleotide modifications such as linkage modifications (e.g., phosphorothioate). Where both one or more methylation-dependent restriction enzymes and one or more methylation-sensitive restriction enzymes are used, the adapters and/or tags may lack methylation and may lack recognition sequences of the one or more methylation-sensitive restriction enzymes, such that they are not substrates for cleavage by any of the restriction enzymes used.

b. Alternative Methods of Modified Nucleic Acid Analysis

In some embodiments the adapters are added to the nucleic acids after partitioning the nucleic acids, in other embodiments the adapters may be added to the nucleic acids prior to partitioning the nucleic acids. In some such methods, a population of nucleic acids bearing the modification to different extents (e.g., 0, 1, 2, 3, 4, 5 or more methyl groups per nucleic acid molecule) is contacted with adapters before fractionation of the population depending on the extent of the modification. Adapters attach to either one end or both ends of nucleic acid molecules in the population. Preferably, the adapters include different tags of sufficient numbers that the number of combinations of tags results in a low probability e.g., 95, 99 or 99.9% of two nucleic acids with the same start and stop points receiving the same combination of tags. Adapters, whether bearing the same or different tags, can include the same or different primer binding sites, but preferably adapters include the same primer binding site. Following attachment of adapters, the nucleic acids are contacted with an agent that preferentially binds to nucleic acids bearing the modification (such as the previously described such agents). The nucleic acids are partitioned into at least two subsamples differing in the extent to which the nucleic acids bear the modification from binding to the agents. For example, if the agent has affinity for nucleic acids bearing the modification, nucleic acids overrepresented in the modification (compared with median representation in the population) preferentially bind to the agent, whereas nucleic acids underrepresented for the modification do not bind or are more easily eluted from the agent. Following partitioning, the first subsample is subjected to a procedure that affects a first nucleobase in the DNA differently from a second nucleobase in the DNA of the first subsample, wherein the first nucleobase is a modified or unmodified nucleobase, the second nucleobase is a modified or unmodified nucleobase different from the first nucleobase, and the first nucleobase and the second nucleobase have the same base pairing specificity. The nucleic acids are then amplified from primers binding to the primer binding sites within the adapters. Following amplification, the different partitions can then be subject to further processing steps, which typically include further (e.g., clonal) amplification, and sequence analysis, in parallel but separately. Sequence data from the different partitions can then be compared.

In another embodiment, a partitioning scheme can be performed using the following exemplary procedure. Nucleic acids are linked at both ends to Y-shaped adapters including primer binding sites and tags. The molecules are amplified. The amplified molecules are then fractionated by contact with an antibody preferentially binding to 5-methylcytosine to produce two partitions. One partition includes original molecules lacking methylation and amplification copies having lost methylation. The other partition includes original DNA molecules with methylation. The partition including original DNA molecules with methylation is subjected to a procedure that affects a first nucleobase in the DNA differently from a second nucleobase in the DNA of the first subsample, wherein the first nucleobase is a modified or unmodified nucleobase, the second nucleobase is a modified or unmodified nucleobase different from the first nucleobase, and the first nucleobase and the second nucleobase have the same base pairing specificity. The two partitions are then processed and sequenced separately with further amplification of the methylated partition. The sequence data of the two partitions can then be compared. In this example, tags are not used to distinguish between methylated and unmethylated DNA but rather to distinguish between different molecules within these partitions so that one can determine whether reads with the same start and stop points are based on the same or different molecules.

The disclosure provides further methods for analyzing a population of nucleic acid in which at least some of the nucleic acids include one or more modified cytosine residues, such as 5-methylcytosine and any of the other modifications described previously. In these methods, after partitioning, the subsamples of nucleic acids are contacted with adapters including one or more cytosine residues modified at the 5C position, such as 5-methylcytosine. Preferably all cytosine residues in such adapters are also modified, or all such cytosines in a primer binding region of the adapters are modified. Adapters attach to both ends of nucleic acid molecules in the population. Preferably, the adapters include different tags of sufficient numbers that the number of combinations of tags results in a low probability e.g., 95, 99 or 99.9% of two nucleic acids with the same start and stop points receiving the same combination of tags. The primer binding sites in such adapters can be the same or different, but are preferably the same. After attachment of adapters, the nucleic acids are amplified from primers binding to the primer binding sites of the adapters. The amplified nucleic acids are split into first and second aliquots. The first aliquot is assayed for sequence data with or without further processing. The sequence data on molecules in the first aliquot is thus determined irrespective of the initial methylation state of the nucleic acid molecules. The nucleic acid molecules in the second aliquot are subjected to a procedure that affects a first nucleobase in the DNA differently from a second nucleobase in the DNA, wherein the first nucleobase comprises a cytosine modified at the 5 position, and the second nucleobase comprises unmodified cytosine. This procedure may be bisulfite treatment or another procedure that converts unmodified cytosines to uracils. The nucleic acids subjected to the procedure are then amplified with primers to the original primer binding sites of the adapters linked to nucleic acid. Only the nucleic acid molecules originally linked to adapters (as distinct from amplification products thereof) are now amplifiable because these nucleic acids retain cytosines in the primer binding sites of the adapters, whereas amplification products have lost the methylation of these cytosine residues, which have undergone conversion to uracils in the bisulfite treatment. Thus, only original molecules in the populations, at least some of which are methylated, undergo amplification. After amplification, these nucleic acids are subject to sequence analysis. Comparison of sequences determined from the first and second aliquots can indicate among other things, which cytosines in the nucleic acid population were subject to methylation.

Such an analysis can be performed using the following exemplary procedure. After partitioning, methylated DNA is linked to Y-shaped adapters at both ends including primer binding sites and tags. The cytosines in the adapters are modified at the 5 position (e.g., 5-methylated). The modification of the adapters serves to protect the primer binding sites in a subsequent conversion step (e.g., bisulfite treatment, TAP conversion, or any other conversion that does not affect the modified cytosine but affects unmodified cytosine). After attachment of adapters, the DNA molecules are amplified. The amplification product is split into two aliquots for sequencing with and without conversion. The aliquot not subjected to conversion can be subjected to sequence analysis with or without further processing. The other aliquot is subjected to a procedure that affects a first nucleobase in the DNA differently from a second nucleobase in the DNA, wherein the first nucleobase comprises a cytosine modified at the 5 position, and the second nucleobase comprises unmodified cytosine. This procedure may be bisulfite treatment or another procedure that converts unmodified cytosines to uracils. Only primer binding sites protected by modification of cytosines can support amplification when contacted with primers specific for original primer binding sites. Thus, only original molecules and not copies from the first amplification are subjected to further amplification. The further amplified molecules are then subjected to sequence analysis. Sequences can then be compared from the two aliquots. As in the separation scheme discussed above, nucleic acid tags in adapters are not used to distinguish between methylated and unmethylated DNA but to distinguish nucleic acid molecules within the same partition.

3. Subjecting the First Subsample to a Procedure that Affects a First Nucleobase in the DNA Differently from a Second Nucleobase in the DNA of the First Subsample Disclosed herein are methods comprising a step of subjecting the second subsample to a procedure that affects a first nucleobase in the DNA differently from a second nucleobase in the DNA of the second subsample, wherein the first nucleobase is a modified or unmodified nucleobase, the second nucleobase is a modified or unmodified nucleobase different from the first nucleobase, and the first nucleobase and the second nucleobase have the same base pairing specificity. In some embodiments, if the first nucleobase is a modified or unmodified adenine, then the second nucleobase is a modified or unmodified adenine; if the first nucleobase is a modified or unmodified cytosine, then the second nucleobase is a modified or unmodified cytosine; if the first nucleobase is a modified or unmodified guanine, then the second nucleobase is a modified or unmodified guanine; and if the first nucleobase is a modified or unmodified thymine, then the second nucleobase is a modified or unmodified thymine (where modified and unmodified uracil are encompassed within modified thymine for the purpose of this step). The methods may also comprise a step of subjecting the first subsample to a procedure that affects a first nucleobase in the DNA differently from a second nucleobase in the DNA of the first subsample, wherein the first nucleobase is a modified or unmodified nucleobase, the second nucleobase is a modified or unmodified nucleobase different from the first nucleobase, and the first nucleobase and the second nucleobase have the same base pairing specificity. In such embodiments, the same or different procedures may be used on the first and second subsamples. Such a procedure can be used to identify nucleotides in the subsample that have or lack certain modifications, such as methylation.

With respect to the procedure to which the second subsample is subjected, in some embodiments, the first nucleobase is a modified or unmodified cytosine, then the second nucleobase is a modified or unmodified cytosine. For example, first nucleobase may comprise unmodified cytosine (C) and the second nucleobase may comprise one or more of 5-methylcytosine (mC) and 5-hydroxymethylcytosine (hmC). Alternatively, the second nucleobase may comprise C and the first nucleobase may comprise one or more of mC and hmC. Other combinations are also possible, as indicated, e.g., in the Summary above and the following discussion, such as where one of the first and second nucleobases comprises mC and the other comprises hmC. Where the first subsample is also subjected to such a procedure, any of the foregoing can also apply to the procedure to which the first subsample is subjected.

In some embodiments, the procedure to which the first and/or second subsample is subjected that affects a first nucleobase in the DNA differently from a second nucleobase in the DNA of the first subsample comprises bisulfite conversion. Treatment with bisulfite converts unmodified cytosine and certain modified cytosine nucleotides (e.g. 5-formyl cytosine (fC) or 5-carboxylcytosine (caC)) to uracil whereas other modified cytosines (e.g., 5-methylcytosine, 5-hydroxylmethylcystosine) are not converted. Thus, where bisulfite conversion is used, the first nucleobase comprises one or more of unmodified cytosine, 5-formyl cytosine, 5-carboxylcytosine, or other cytosine forms affected by bisulfite, and the second nucleobase may comprise one or more of mC and hmC, such as mC and optionally hmC. Sequencing of bisulfite-treated DNA identifies positions that are read as cytosine as being mC or hmC positions. Meanwhile, positions that are read as T are identified as being T or a bisulfite-susceptible form of C, such as unmodified cytosine, 5-formyl cytosine, or 5-carboxylcytosine. Performing bisulfite conversion on a first subsample as described herein thus facilitates identifying positions containing mC or hmC using the sequence reads obtained from the first subsample. For an exemplary description of bisulfite conversion, see, e.g., Moss et al., *Nat Commun.* 2018; 9: 5068.

In some embodiments, the procedure to which the first and/or second subsample is subjected that affects a first nucleobase in the DNA differently from a second nucleobase in the DNA of the first subsample comprises oxidative bisulfite (Ox-BS) conversion. This procedure first converts hmC to fC, which is bisulfite susceptible, followed by bisulfite conversion. Thus, when oxidative bisulfite conversion is used, the first nucleobase comprises one or more of unmodified cytosine, fC, caC, hmC, or other cytosine forms affected by bisulfite, and the second nucleobase comprises mC. Sequencing of Ox-BS converted DNA identifies positions that are read as cytosine as being mC positions. Meanwhile, positions that are read as T are identified as being T, hmC, or a bisulfite-susceptible form of C, such as unmodified cytosine, fC, or hmC. Performing Ox-BS conversion on a first subsample as described herein thus facilitates identifying positions containing mC using the sequence reads obtained from the first subsample. For an exemplary description of oxidative bisulfite conversion, see, e.g., Booth et al., *Science* 2012; 336: 934-937.

In some embodiments, the procedure to which the first and/or second subsample is subjected that affects a first nucleobase in the DNA differently from a second nucleobase in the DNA of the first subsample comprises Tet-assisted bisulfite (TAB) conversion. In TAB conversion, hmC is protected from conversion and mC is oxidized in advance of bisulfite treatment, so that positions originally occupied by mC are converted to U while positions originally occupied by hmC remain as a protected form of cytosine. For example, as described in Yu et al., *Cell* 2012; 149: 1368-80, β-glucosyl transferase can be used to protect hmC (forming 5-glucosylhydroxymethylcytosine (ghmC)), then a TET protein such as mTet1 can be used to convert mC to caC, and then bisulfite treatment can be used to convert C and caC to U while ghmC remains unaffected. Thus, when TAB conversion is used, the first nucleobase comprises one or more of unmodified cytosine, fC, caC, mC, or other cytosine forms affected by bisulfite, and the second nucleobase comprises hmC. Sequencing of TAB-converted DNA identifies positions that are read as cytosine as being hmC positions. Meanwhile, positions that are read as T are identified as being T, mC, or a bisulfite-susceptible form of C, such as unmodified cytosine, fC, or caC. Performing TAB conversion on a first subsample as described herein thus facilitates identifying positions containing hmC using the sequence reads obtained from the first subsample.

In some embodiments, the procedure to which the first and/or second subsample is subjected that affects a first nucleobase in the DNA differently from a second nucleobase in the DNA of the first subsample comprises Tet-assisted conversion with a substituted borane reducing agent, optionally wherein the substituted borane reducing agent is 2-picoline borane, borane pyridine, tert-butylamine borane, or ammonia borane. In Tet-assisted pic-borane conversion with a substituted borane reducing agent (e.g., TAP), a TET protein is used to convert mC and hmC to caC, without affecting unmodified C. caC, and fC if present, are then converted to dihydrouracil (DHU) by treatment with 2-picoline borane (pic-borane) or another substituted borane reducing agent such as borane pyridine, tert-butylamine borane, or ammonia borane, also without affecting unmodified C. See, e.g., Liu et al., *Nature Biotechnology* 2019; 37:424-429 (e.g., at Supplementary FIG. 1 and Supplementary Note 7). DHU is read as a T in sequencing. Thus, when this type of conversion is used, the first nucleobase comprises one or more of mC, fC, caC, or hmC, and the second nucleobase comprises unmodified cytosine. Sequencing of the converted DNA identifies positions that are read as cytosine as being unmodified C positions. Meanwhile, positions that are read as T are identified as being T, mC, fC, caC, or hmC. Performing TAP conversion on a first subsample as described herein thus facilitates identifying positions containing unmodified C using the sequence reads obtained from the first subsample. This procedure encompasses Tet-assisted pyridine borane sequencing (TAPS), described in further detail in Liu et al. 2019, supra. In some embodiments, the procedure to which the second subsample is subjected is Tet-assisted pic-borane conversion with a substituted borane reducing agent, while the procedure to which the first subsample is subjected is a procedure that converts unmethylated cytosines, such as any of those described herein. This combination of procedures should facilitate identification of nonspecifically partitioned molecules while minimizing the impacts on hypermethylated molecules in the hypermethylated partition and hypomethylated molecules in the hypomethylated partition.

Alternatively, protection of hmC (e.g., using βGT) can be combined with Tet-assisted conversion with a substituted borane reducing agent. hmC can be protected as noted above through glucosylation using βGT, forming ghmC. Treatment with a TET protein such as mTet1 then converts mC to caC but does not convert C or ghmC. caC is then converted to DHU by treatment with pic-borane or another substituted borane reducing agent such as borane pyridine, tert-butylamine borane, or ammonia borane, also without affecting unmodified C or ghmC. Thus, when Tet-assisted conversion with a substituted borane reducing agent is used, the first nucleobase comprises mC, and the second nucleobase comprises one or more of unmodified cytosine or hmC, such as unmodified cytosine and optionally hmC, fC, and/or caC. Sequencing of the converted DNA identifies positions that are read as cytosine as being either hmC or unmodified C positions. Meanwhile, positions that are read as T are identified as being T, fC, caC, or mC. Performing TAPSβ conversion on a first subsample as described herein thus facilitates distinguishing positions containing unmodified C or hmC on the one hand from positions containing mC using the sequence reads obtained from the first subsample. For an exemplary description of this type of conversion, see, e.g., Liu et al., *Nature Biotechnology* 2019; 37:424-429.

In some embodiments, the procedure that affects a first nucleobase in the DNA differently from a second nucleobase in the DNA of the first subsample comprises chemical-assisted conversion with a substituted borane reducing agent, optionally wherein the substituted borane reducing agent is 2-picoline borane, borane pyridine, tert-butylamine borane, or ammonia borane. In chemical-assisted conversion with a substituted borane reducing agent, an oxidizing agent such as potassium perruthenate ($KRuO_4$) (also suitable for use in ox-BS conversion) is used to specifically oxidize hmC to fC. Treatment with pic-borane or another substituted borane reducing agent such as borane pyridine, tert-butylamine borane, or ammonia borane converts fC and caC to DHU but does not affect mC or unmodified C. Thus, when this type of conversion is used, the first nucleobase comprises one or more of hmC, fC, and caC, and the second nucleobase comprises one or more of unmodified cytosine or mC, such as unmodified cytosine and optionally mC. Sequencing of the converted DNA identifies positions that are read as cytosine as being either mC or unmodified C positions. Meanwhile, positions that are read as T are identified as being T, fC, caC, or hmC. Performing this type of conversion on a first subsample as described herein thus facilitates distinguishing positions containing unmodified C or mC on the one hand from positions containing hmC using the sequence reads obtained from the first subsample. For an exemplary description of this type of conversion, see, e.g., Liu et al., *Nature Biotechnology* 2019; 37:424-429.

In some embodiments, the procedure that affects a first nucleobase in the DNA differently from a second nucleobase in the DNA of the first subsample comprises APOBEC-coupled epigenetic (ACE) conversion. In ACE conversion, an AID/APOBEC family DNA deaminase enzyme such as APOBEC3A (A3A) is used to deaminate unmodified cytosine and mC without deaminating hmC, fC, or caC. Thus, when ACE conversion is used, the first nucleobase comprises unmodified C and/or mC (e.g., unmodified C and optionally mC), and the second nucleobase comprises hmC. Sequencing of ACE-converted DNA identifies positions that are read as cytosine as being hmC, fC, or caC positions. Meanwhile, positions that are read as T are identified as being T, unmodified C, or mC. Performing ACE conversion on a first subsample as described herein thus facilitates distinguishing positions containing hmC from positions containing mC or unmodified C using the sequence reads obtained from the first subsample. For an exemplary description of ACE conversion, see, e.g., Schutsky et al., *Nature Biotechnology* 2018; 36: 1083-1090.

In some embodiments, procedure that affects a first nucleobase in the DNA differently from a second nucleobase in the DNA of the first subsample comprises enzymatic conversion of the first nucleobase, e.g., as in EM-Seq. See, e.g., Vaisvila R, et al. (2019) EM-seq: Detection of DNA methylation at single base resolution from picograms of DNA. bioRxiv; DOI: 10.1101/2019.12.20.884692, available on www.biorxiv.org at/content/10.1101/2019.12.20.884692v1. For example, TET2 and T4-βGT can be used to convert 5mC and 5hmC into substrates that cannot be deaminated by a deaminase (e.g., APOBEC3A), and then a deaminase (e.g., APOBEC3A) can be used to deaminate unmodified cytosines converting them to uracils.

In some embodiments, the procedure that affects a first nucleobase in the DNA differently from a second nucleobase in the DNA of the first subsample comprises separating DNA originally comprising the first nucleobase from DNA not originally comprising the first nucleobase. In some such embodiments, the first nucleobase is hmC. DNA originally comprising the first nucleobase may be separated from other DNA using a labeling procedure comprising biotinylating positions that originally comprised the first nucleobase. In some embodiments, the first nucleobase is first derivatized with an azide-containing moiety, such as a glucosyl-azide containing moiety. The azide-containing moiety then may serve as a reagent for attaching biotin, e.g., through Huisgen cycloaddition chemistry. Then, the DNA originally comprising the first nucleobase, now biotinylated, can be separated from DNA not originally comprising the first nucleobase using a biotin-binding agent, such as avidin, neutravidin (deglycosylated avidin with an isoelectric point of about 6.3), or streptavidin. An example of a procedure for separating DNA originally comprising the first nucleobase from DNA not originally comprising the first nucleobase is hmC-seal, which labels hmC to form β-6-azide-glucosyl-5-hydroxymethylcytosine and then attaches a biotin moiety through Huisgen cycloaddition, followed by separation of the biotinylated DNA from other DNA using a biotin-binding agent. For an exemplary description of hmC-seal, see, e.g., Han et al., *Mol. Cell* 2016; 63: 711-719. This approach is useful for identifying fragments that include one or more hmC nucleobases.

In some embodiments, following such a separation, the method further comprises differentially tagging each of the DNA originally comprising the first nucleobase, the DNA not originally comprising the first nucleobase, and the DNA of the second subsample. The method may further comprise pooling the DNA originally comprising the first nucleobase, the DNA not originally comprising the first nucleobase, and the DNA of the second subsample following differential tagging. The DNA originally comprising the first nucleobase, the DNA not originally comprising the first nucleobase, and the DNA of the second subsample may then be sequenced in the same sequencing cell while retaining the ability to resolve whether a given read came from a molecule of DNA originally comprising the first nucleobase, DNA not originally comprising the first nucleobase, or DNA of the second subsample using the differential tags.

In some embodiments, the first nucleobase is a modified or unmodified adenine, and the second nucleobase is a modified or unmodified adenine. In some embodiments, the modified adenine is $N^6$-methyladenine (mA). In some embodiments, the modified adenine is one or more of $N^6$-methyladenine (mA), $N^6$-hydroxymethyladenine (hmA), or $N^6$-formyladenine (fA).

Techniques comprising methylated DNA immunoprecipitation (MeDIP) can be used to separate DNA containing modified bases such as mA from other DNA. See, e.g., Kumar et al., *Frontiers Genet.* 2018; 9: 640; Greer et al., *Cell* 2015; 161: 868-878. An antibody specific for mA is described in Sun et al., *Bioessays* 2015; 37:1155-62. Antibodies for various modified nucleobases, such as forms of thymine/uracil including halogenated forms such as 5-bromouracil, are commercially available. Various modified bases can also be detected based on alterations in their base-pairing specificity. For example, hypoxanthine is a modified form of adenine that can result from deamination and is read in sequencing as a G. See, e.g., U.S. Pat. No. 8,486,630; Brown, *Genomes,* 2nd Ed., John Wiley & Sons, Inc., New York, N.Y., 2002, chapter 14, "Mutation, Repair, and Recombination."

4. Contacting a Subsample with a Methylation-Sensitive Nuclease

In some embodiments, a subsample (e.g., a first and/or third subsample prepared by partitioning a sample as described herein, such as on the basis of a level of a cytosine modification, such as methylation, e.g., 5-methylation) is contacted with a methylation-sensitive nuclease. Unless otherwise indicated, where partitioning is performed on the basis of a cytosine modification, the first subsample is the subsample with a higher level of the modification; the second subsample is the subsample with a lower level of the modification; and, when present, the third subsample has a level of the modification intermediate between the first and second subsamples.

As discussed above, partitioning procedures may result in imperfect sorting of DNA molecules among the subsamples. The methylation-sensitive nuclease can be used to degrade nonspecifically partitioned DNA (e.g., hypomethylated DNA) in the first or third subsample. In some embodiments, the first subsample can be contacted with a methylation-sensitive endonuclease, such as a methylation-sensitive restriction enzyme, thereby degrading nonspecifically partitioned DNA in the first subsample to produce a treated first subsample. Degradation of nonspecifically partitioned DNA is proposed as an improvement to the performance of methods that rely on accurate partitioning of DNA on the basis of a cytosine modification, e.g., to detect the presence of aberrantly modified DNA in a sample, to determine the tissue of origin of DNA, and/or to determine whether a subject has cancer. For example, such degradation may provide improved sensitivity and/or simplify downstream analyses.

In a contacting a subsample with a nuclease, one or more nucleases can be used. In some embodiments, a subsample is contacted with a plurality of nucleases. The subsample may be contacted with the nucleases sequentially or simultaneously. Simultaneous use of nucleases may be advantageous when the nucleases are active under similar conditions (e.g., buffer composition) to avoid unnecessary sample manipulation. Contacting the second subsample with more than one methylation-dependent restriction enzyme can more completely degrade nonspecifically partitioned hypermethylated DNA. Similarly, contacting the first subsample with more than one methylation-sensitive restriction enzyme can more completely degrade nonspecifically partitioned hypomethylated and/or unmethylated DNA.

In some embodiments, a methylation-sensitive nuclease comprises one or more of AatII, AccII, AciI, Aor13HI, Aor15HI, BspT104I, BssHII, BstUI, Cfr10I, ClaI, CpoI, Eco52I, HaeII, HapII, HhaI, Hin6I, HpaII, HpyCH4IV, MluI, MspI, NaeI, NotI, NruI, NsbI, PmaCI, Psp1406I, PvuI, SacII, SalI, SmaI, and SnaBI. In some embodiments, at least two methylation-sensitive nucleases are used. In some embodiments, at least three methylation-sensitive nucleases are used. In some embodiments, the methylation-sensitive nucleases comprise BstUI and HpaII. In some embodiments, the two methylation-sensitive nucleases comprise HhaI and AccII. In some embodiments, the methylation-sensitive nucleases comprise BstUI, HpaII and Hin6I.

In embodiments involving a third subsample (e.g., an intermediately methylated partition), the nucleic acid molecules therein may be digested with a methylation-sensitive nuclease. In some embodiments, the nucleic acid molecules in a third subsample (e.g., an intermediately methylated partition) are digested with the same nuclease(s) as the first subsample (e.g., a hypermethylated partition). For example, the third subsample (e.g., intermediately methylated partition) may be pooled with the first subsample (e.g., hypermethylated partition) and then the pooled partitions may be subjected to digestion.

In some embodiments, a subsample is contacted with a nuclease as described above after a step of tagging or attaching adapters to both ends of the DNA. The tags or adapters can be resistant to cleavage by the nuclease using any of of the approaches described above. In this approach, cleavage can prevent the nonspecifically partitioned molecule from being carried through the analysis because the cleavage products lack tags or adapters at both ends.

Alternatively, a step of tagging or attaching adapters can be performed after cleavage with a nuclease as described above. Cleaved molecules can be then identified in sequence reads based on having an end (point of attachment to tag or adapter) corresponding to a nuclease recognition site. Processing the molecules in this way can also allow the acquisition of information from the cleaved molecule, e.g., observation of somatic mutations. When tagging or attaching adapters after contacting the subsample with a nuclease, and low molecular weight DNA such as cfDNA is being analyzed, it may be desirable to remove high molecular weight DNA (such as contaminating genomic DNA) from the sample before the contacting step. It may also be desirable to use nucleases that can be heat-inactivated at a relatively low temperature (e.g., 65° C. or less, or 60° C. or less) to avoid denaturing DNA, in that denaturation may interfere with subsequent ligation steps.

Where a sample is partitioned into three subsamples, including a third subsample containing intermediately methylated molecules, the third subsample is in some embodiments contacted with a methylation-sensitive nuclease. Such a step may have any of the features described elsewhere herein with respect to contacting steps, and may be performed before or after a step of tagging or attaching adapters as discussed above. In some embodiments, the first and third subsamples are combined before being contacted with a methylation-sensitive nuclease. Such a step may have any of the features described elsewhere herein with respect to contacting steps, and may be performed before or after a step of tagging or attaching adapters as discussed above. In some embodiments, the first and third subsamples are differentially tagged before being combined.

In some embodiments, the DNA is purified after being contacted with the nuclease, e.g., using SPRI beads. Such purification may occur after heat inactivation of the nuclease. Alternatively, purification can be omitted; thus, for example, a subsequent step such as amplification can be performed on the subsample containing heat-inactivated nuclease. In another embodiment, the contacting step can occur in the presence of a purification reagent such as SPRI beads, e.g., to minimize losses associated with tube transfers. After cleavage and heat inactivation, the SPRI beads can be re-used for cleanup by adding molecular crowding reagents (e.g., PEG) and salt.

5. Enriching/Capturing Step; Amplification; Adaptors; Barcodes

In some embodiments, methods disclosed herein comprise a step of capturing one or more sets of target regions of DNA, such as cfDNA. Capture may be performed using any suitable approach known in the art.

In some embodiments, capturing comprises contacting the DNA to be captured with a set of target-specific probes. The set of target-specific probes may have any of the features described herein for sets of target-specific probes, including but not limited to in the embodiments set forth above and the sections relating to probes below. Capturing may be performed on one or more subsamples prepared during methods disclosed herein. In some embodiments, DNA is captured from at least the first subsample or the second subsample, e.g., at least the first subsample and the second subsample. In some embodiments, the subsamples are differentially tagged (e.g., as described herein) and then pooled before undergoing capture.

The capturing step may be performed using conditions suitable for specific nucleic acid hybridization, which generally depend to some extent on features of the probes such as length, base composition, etc. Those skilled in the art will be familiar with appropriate conditions given general knowledge in the art regarding nucleic acid hybridization. In some embodiments, complexes of target-specific probes and DNA are formed.

In some embodiments, a method described herein comprises capturing cfDNA obtained from a test subject for a plurality of sets of target regions. The target regions comprise epigenetic target regions, which may show differences in methylation levels and/or fragmentation patterns depending on whether they originated from a tumor or from healthy cells. The target regions also comprise sequence-variable target regions, which may show differences in sequence depending on whether they originated from a tumor or from healthy cells. The capturing step produces a captured set of cfDNA molecules, and the cfDNA molecules corresponding to the sequence-variable target region set are captured at a greater capture yield in the captured set of cfDNA molecules than cfDNA molecules corresponding to the epigenetic target region set. For additional discussion of capturing steps, capture yields, and related aspects, see WO2020/160414, which is incorporated herein by reference for all purposes.

In some embodiments, a method described herein comprises contacting cfDNA obtained from a test subject with a set of target-specific probes, wherein the set of target-specific probes is configured to capture cfDNA corresponding to the sequence-variable target region set at a greater capture yield than cfDNA corresponding to the epigenetic target region set.

It can be beneficial to capture cfDNA corresponding to the sequence-variable target region set at a greater capture yield than cfDNA corresponding to the epigenetic target region set because a greater depth of sequencing may be necessary to analyze the sequence-variable target regions with sufficient confidence or accuracy than may be necessary to analyze the epigenetic target regions. The volume of data needed to determine fragmentation patterns (e.g., to test fsor perturbation of transcription start sites or CTCF binding sites) or fragment abundance (e.g., in hypermethylated and hypomethylated partitions) is generally less than the volume of data needed to determine the presence or absence of cancer-related sequence mutations. Capturing the target region sets at different yields can facilitate sequencing the target regions to different depths of sequencing in the same sequencing run (e.g., using a pooled mixture and/or in the same sequencing cell).

In various embodiments, the methods further comprise sequencing the captured cfDNA, e.g., to different degrees of sequencing depth for the epigenetic and sequence-variable target region sets, consistent with the discussion herein.

In some embodiments, complexes of target-specific probes and DNA are separated from DNA not bound to target-specific probes. For example, where target-specific probes are bound covalently or noncovalently to a solid support, a washing or aspiration step can be used to separate unbound material. Alternatively, where the complexes have chromatographic properties distinct from unbound material (e.g., where the probes comprise a ligand that binds a chromatographic resin), chromatography can be used.

As discussed in detail elsewhere herein, the set of target-specific probes may comprise a plurality of sets such as probes for a sequence-variable target region set and probes for an epigenetic target region set. In some such embodiments, the capturing step is performed with the probes for the sequence-variable target region set and the probes for the epigenetic target region set in the same vessel at the same time, e.g., the probes for the sequence-variable and epigenetic target region sets are in the same composition. This approach provides a relatively streamlined workflow. In some embodiments, the concentration of the probes for the sequence-variable target region set is greater that the concentration of the probes for the epigenetic target region set.

Alternatively, the capturing step is performed with the sequence-variable target region probe set in a first vessel and with the epigenetic target region probe set in a second vessel, or the contacting step is performed with the sequence-variable target region probe set at a first time and a first vessel and the epigenetic target region probe set at a second time before or after the first time. This approach allows for preparation of separate first and second compositions comprising captured DNA corresponding to the sequence-variable target region set and captured DNA corresponding to the epigenetic target region set. The compositions can be processed separately as desired (e.g., to fractionate based on methylation as described elsewhere herein) and recombined in appropriate proportions to provide material for further processing and analysis such as sequencing.

In some embodiments, the DNA is amplified. In some embodiments, amplification is performed before the capturing step. In some embodiments, amplification is performed after the capturing step.

In some embodiments, adapters are included in the DNA. This may be done concurrently with an amplification procedure, e.g., by providing the adapters in a 5' portion of a primer, e.g., as described above. Alternatively, adapters can be added by other approaches, such as ligation.

In some embodiments, tags, which may be or include barcodes, are included in the DNA. Tags can facilitate identification of the origin of a nucleic acid. For example, barcodes can be used to allow the origin (e.g., subject) whence the DNA came to be identified following pooling of a plurality of samples for parallel sequencing. This may be done concurrently with an amplification procedure, e.g., by providing the barcodes in a 5' portion of a primer, e.g., as described above. In some embodiments, adapters and tags/barcodes are provided by the same primer or primer set. For example, the barcode may be located 3' of the adapter and 5' of the target-hybridizing portion of the primer. Alternatively, barcodes can be added by other approaches, such as ligation, optionally together with adapters in the same ligation substrate.

Additional details regarding amplification, tags, and barcodes are discussed in the "General Features of the Methods" section below, which can be combined to the extent practicable with any of the foregoing embodiments and the embodiments set forth in the introduction and summary section.

6. Captured Set

In some embodiments, a captured set of DNA (e.g., cfDNA) is provided. With respect to the disclosed methods, the captured set of DNA may be provided, e.g., by performing a capturing step after a partitioning step as described herein. The captured set may comprise DNA corresponding to a sequence-variable target region set, an epigenetic target region set, or a combination thereof.

In some embodiments, a first target region set is captured from the first subsample, comprising at least epigenetic target regions. The epigenetic target regions captured from the first subsample may comprise hypermethylation variable target regions. In some embodiments, the hypermethylation variable target regions are CpG-containing regions that are unmethylated or have low methylation in cfDNA from healthy subjects (e.g., below-average methylation relative to bulk cfDNA). In some embodiments, the hypermethylation variable target regions are regions that show lower methylation in healthy cfDNA than in at least one other tissue type. Without wishing to be bound by any particular theory, cancer cells may shed more DNA into the bloodstream than healthy cells of the same tissue type. As such, the distribution of tissue of origin of cfDNA may change upon carcinogenesis. Thus, an increase in the level of hypermethylation variable target regions in the first subsample can be an indicator of the presence (or recurrence, depending on the history of the subject) of cancer.

In some embodiments, a second target region set is captured from the second subsample, comprising at least epigenetic target regions. The epigenetic target regions may comprise hypomethylation variable target regions. In some embodiments, the hypomethylation variable target regions are CpG-containing regions that are methylated or have high methylation in cfDNA from healthy subjects (e.g., above-average methylation relative to bulk cfDNA). In some embodiments, the hypomethylation variable target regions are regions that show higher methylation in healthy cfDNA than in at least one other tissue type. Without wishing to be bound by any particular theory, cancer cells may shed more DNA into the bloodstream than healthy cells of the same tissue type. As such, the distribution of tissue of origin of cfDNA may change upon carcinogenesis. Thus, an increase in the level of hypomethylation variable target regions in the second subsample can be an indicator of the presence (or recurrence, depending on the history of the subject) of cancer.

In some embodiments the quantity of captured sequence-variable target region DNA is greater than the quantity of the captured epigenetic target region DNA, when normalized for the difference in the size of the targeted regions (footprint size).

Alternatively, first and second captured sets may be provided, comprising, respectively, DNA corresponding to a sequence-variable target region set and DNA corresponding to an epigenetic target region set. The first and second captured sets may be combined to provide a combined captured set.

In some embodiments in which a captured set comprising DNA corresponding to the sequence-variable target region set and the epigenetic target region set includes a combined captured set as discussed above, the DNA corresponding to the sequence-variable target region set may be present at a greater concentration than the DNA corresponding to the epigenetic target region set, e.g., a 1.1 to 1.2-fold greater concentration, a 1.2- to 1.4-fold greater concentration, a 1.4- to 1.6-fold greater concentration, a 1.6- to 1.8-fold greater concentration, a 1.8- to 2.0-fold greater concentration, a 2.0- to 2.2-fold greater concentration, a 2.2- to 2.4-fold greater concentration a 2.4- to 2.6-fold greater concentration, a 2.6- to 2.8-fold greater concentration, a 2.8- to 3.0-fold greater concentration, a 3.0- to 3.5-fold greater concentration, a 3.5- to 4.0, a 4.0- to 4.5-fold greater concentration, a 4.5- to 5.0-fold greater concentration, a 5.0- to 5.5-fold greater concentration, a 5.5- to 6.0-fold greater concentration, a 6.0- to 6.5-fold greater concentration, a 6.5- to 7.0-fold greater, a 7.0- to 7.5-fold greater concentration, a 7.5- to 8.0-fold greater concentration, an 8.0- to 8.5-fold greater concentration, an 8.5- to 9.0-fold greater concentration, a 9.0- to 9.5-fold greater concentration, 9.5- to 10.0-fold greater concentration, a 10- to 11-fold greater concentration, an 11- to 12-fold greater concentration a 12- to 13-fold greater concentration, a 13- to 14-fold greater concentration, a 14- to 15-fold greater concentration, a 15- to 16-fold greater concentration, a 16- to 17-fold greater concentration, a 17- to 18-fold greater concentration, an 18- to 19-fold greater concentration, a 19- to 20-fold greater concentration, a 20- to 30-fold greater concentration, a 30- to 40-fold greater concentration, a 40- to 50-fold greater concentration, a 50- to 60-fold greater concentration, a 60- to 70-fold greater concentration, a 70- to 80-fold greater concentration, a 80- to 90-fold greater concentration, or a 90- to 100-fold greater concentration. The degree of difference in concentrations accounts for normalization for the footprint sizes of the target regions, as discussed in the definition section.

a. Epigenetic Target Region Set

The epigenetic target region set may comprise one or more types of target regions likely to differentiate DNA from neoplastic (e.g., tumor or cancer) cells and from healthy cells, e.g., non-neoplastic circulating cells. Exemplary types of such regions are discussed in detail herein. The epigenetic target region set may also comprise one or more control regions, e.g., as described herein.

In some embodiments, the epigenetic target region set has a footprint of at least 100 kbp, e.g., at least 200 kbp, at least 300 kbp, or at least 400 kbp. In some embodiments, the epigenetic target region set has a footprint in the range of 100-20 Mbp, e.g., 100-200 kbp, 200-300 kbp, 300-400 kbp, 400-500 kbp, 500-600 kbp, 600-700 kbp, 700-800 kbp, 800-900 kbp, 900-1,000 kbp, 1-1.5 Mbp, 1.5-2 Mbp, 2-3 Mbp, 3-4 Mbp, 4-5 Mbp, 5-6 Mbp, 6-7 Mbp, 7-8 Mbp, 8-9 Mbp, 9-10 Mbp, or 10-20 Mbp. In some embodiments, the epigenetic target region set has a footprint of at least 20 Mbp.

i. Hypermethylation Variable Target Regions

In some embodiments, the epigenetic target region set comprises one or more hypermethylation variable target regions. In general, hypermethylation variable target regions refer to regions where an increase in the level of observed methylation, e.g., in a cfDNA sample, indicates an increased likelihood that a sample (e.g., of cfDNA) contains DNA produced by neoplastic cells, such as tumor or cancer cells. For example, hypermethylation of promoters of tumor suppressor genes has been observed repeatedly. See, e.g., Kang et al., Genome Biol. 18:53 (2017) and references cited therein. In another example, as discussed above, hypermethylation variable target regions can include regions that do not necessarily differ in methylation in cancerous tissue relative to DNA from healthy tissue of the same type, but do differ in methylation (e.g., have more methylation) relative to cfDNA that is typical in healthy subjects. Where, for example, the presence of a cancer results in increased cell death such as apoptosis of cells of the tissue type corresponding to the cancer, such a cancer can be detected at least in part using such hypermethylation variable target regions.

An extensive discussion of methylation variable target regions in colorectal cancer is provided in Lam et al., Biochim Biophys Acta. 1866:106-20 (2016). These include VIM, SEPT9, ITGA4, OSM4, GATA4 and NDRG4. An exemplary set of hypermethylation variable target regions based on colorectal cancer (CRC) studies is provided in Table 1. Many of these genes likely have relevance to cancers beyond colorectal cancer; for example, TP53 is widely recognized as a critically important tumor suppressor and hypermethylation-based inactivation of this gene may be a common oncogenic mechanism.

TABLE 1

Exemplary Hypermethylation Target Regions based on CRC studies.

| Gene Name | Additional Gene Name | Chromosome |
| --- | --- | --- |
| VIM |  | chr10 |
| SEPT9 |  | chr17 |
| CYCD2 | CCND2 | chr12 |
| TFPI2 |  | chr7 |
| GATA4 |  | chr8 |
| RARB2 | RARB | chr3 |
| p16INK4a | CDKN2A | chr9 |
| MGMT | MGMT | chr10 |
| APC |  | chr5 |
| NDRG4 |  | chr16 |
| HLTF |  | chr3 |
| HPP1 | TMEFF2 | chr2 |
| hMLH1 | MLH1 | chr3 |
| RASSF1A | RASSF1 | chr3 |
| CDH13 |  | chr16 |
| IGFBP3 |  | chr7 |
| ITGA4 |  | chr2 |

In some embodiments, the hypermethylation variable target regions comprise a plurality of loci listed in Table 1, e.g., at least 10%, 20%, 30%, 40%, 50%, 60%, 70%, 80%, 90%, or 100% of the loci listed in Table 1. For example, for each locus included as a target region, there may be one or more probes with a hybridization site that binds between the transcription start site and the stop codon (the last stop codon for genes that are alternatively spliced) of the gene, or in the promoter region of the gene. In some embodiments, the one or more probes bind within 300 bp of the transcription start site of a gene in Table 1, e.g., within 200 or 100 bp.

Methylation variable target regions in various types of lung cancer are discussed in detail, e.g., in Ooki et al., Clin. Cancer Res. 23:7141-52 (2017); Belinksy, Annu. Rev. Physiol. 77:453-74 (2015); Hulbert et al., Clin. Cancer Res. 23:1998-2005 (2017); Shi et al., *BMC Genomics* 18:901 (2017); Schneider et al., BMC Cancer. 11:102 (2011); Lissa et al., Transl Lung Cancer Res 5(5):492-504 (2016); Skvortsova et al., Br. J. Cancer. 94(10):1492-1495 (2006); Kim et al., Cancer Res. 61:3419-3424 (2001); Furonaka et al., Pathology International 55:303-309 (2005); Gomes et al., Rev. Port. Pneumol. 20:20-30 (2014); Kim et al., Oncogene. 20:1765-70 (2001); Hopkins-Donaldson et al., Cell Death Differ. 10:356-64 (2003); Kikuchi et al., Clin. Cancer Res. 11:2954-61 (2005); Heller et al., Oncogene 25:959-968 (2006); Licchesi et al., Carcinogenesis. 29:895-904 (2008); Guo et al., Clin. Cancer Res. 10:7917-24 (2004); Palmisano et al., Cancer Res. 63:4620-4625 (2003); and Toyooka et al., Cancer Res. 61:4556-4560, (2001).

An exemplary set of hypermethylation variable target regions based on lung cancer studies is provided in Table 2. Many of these genes likely have relevance to cancers beyond lung cancer; for example, Casp8 (Caspase 8) is a key enzyme in programmed cell death and hypermethylation-based inactivation of this gene may be a common oncogenic mechanism not limited to lung cancer. Additionally, a number of genes appear in both Tables 1 and 2, indicating generality.

TABLE 2

Exemplary Hypermethylation Target Regions based on Lung Cancer studies

| Gene Name | Chromosome |
|---|---|
| MARCH11 | chr5 |
| TAC1 | chr7 |
| TCF21 | chr6 |
| SHOX2 | chr3 |
| p16 | chr3 |
| Casp8 | chr2 |
| CDH13 | chr16 |
| MGMT | chr10 |
| MLH1 | chr3 |
| MSH2 | chr2 |
| TSLC1 | chr11 |
| APC | chr5 |
| DKK1 | chr10 |
| DKK3 | chr11 |
| LKB1 | chr11 |
| WIF1 | chr12 |
| RUNX3 | chr1 |
| GATA4 | chr8 |
| GATA5 | chr20 |
| PAX5 | chr9 |
| E-Cadherin | chr16 |
| H-Cadherin | chr16 |

Any of the foregoing embodiments concerning target regions identified in Table 2 may be combined with any of the embodiments described above concerning target regions identified in Table 1. In some embodiments, the hypermethylation variable target regions comprise a plurality of loci listed in Table 1 or Table 2, e.g., at least 10%, 20%, 30%, 40%, 50%, 60%, 70%, 80%, 90%, or 100% of the loci listed in Table 1 or Table 2.

Additional hypermethylation target regions may be obtained, e.g., from the Cancer Genome Atlas. Kang et al., Genome Biology 18:53 (2017), describe construction of a probabilistic method called CancerLocator using hypermethylation target regions from breast, colon, kidney, liver, and lung. In some embodiments, the hypermethylation target regions can be specific to one or more types of cancer. Accordingly, in some embodiments, the hypermethylation target regions include one, two, three, four, or five subsets of hypermethylation target regions that collectively show hypermethylation in one, two, three, four, or five of breast, colon, kidney, liver, and lung cancers.

In some embodiments, where different epigenetic target regions are captured from the first and second subsamples, the epigenetic target regions captured from the first subsample comprise hypermethylation variable target regions.

ii. Hypomethylation Variable Target Regions

Global hypomethylation is a commonly observed phenomenon in various cancers. See, e.g., Hon et al., Genome Res. 22:246-258 (2012) (breast cancer); Ehrlich, Epigenomics 1:239-259 (2009) (review article noting observations of hypomethylation in colon, ovarian, prostate, leukemia, hepatocellular, and cervical cancers). For example, regions such as repeated elements, e.g., LINE1 elements, Alu elements, centromeric tandem repeats, pericentromeric tandem repeats, and satellite DNA, and intergenic regions that are ordinarily methylated in healthy cells may show reduced methylation in tumor cells. Accordingly, in some embodiments, the epigenetic target region set includes hypomethylation variable target regions, where a decrease in the level of observed methylation indicates an increased likelihood that a sample (e.g., of cfDNA) contains DNA produced by neoplastic cells, such as tumor or cancer cells. In another example, as discussed above, hypomethylation variable target regions can include regions that do not necessarily differ in methylation in cancerous tissue relative to DNA from healthy tissue of the same type, but do differ in methylation (e.g., are less methylated) relative to cfDNA that is typical in healthy subjects. Where, for example, the presence of a cancer results in increased cell death such as apoptosis of cells of the tissue type corresponding to the cancer, such a cancer can be detected at least in part using such hypomethylation variable target regions.

In some embodiments, hypomethylation variable target regions include repeated elements and/or intergenic regions. In some embodiments, repeated elements include one, two, three, four, or five of LINE1 elements, Alu elements, centromeric tandem repeats, pericentromeric tandem repeats, and/or satellite DNA.

Exemplary specific genomic regions that show cancer-associated hypomethylation include nucleotides 8403565-8953708 and 151104701-151106035 of human chromosome 1. In some embodiments, the hypomethylation variable target regions overlap or comprise one or both of these regions.

In some embodiments, where different epigenetic target regions are captured from the first and second subsamples, the epigenetic target regions captured from the second subsample comprise hypomethylation variable target regions. In some embodiments, the epigenetic target regions captured from the second subsample comprise hypomethylation variable target regions and the epigenetic target regions captured from the first subsample comprise hypermethylation variable target regions.

iii. CTCF Binding Regions

CTCF is a DNA-binding protein that contributes to chromatin organization and often colocalizes with cohesin. Perturbation of CTCF binding sites has been reported in a variety of different cancers. See, e.g., Katainen et al., Nature Genetics, doi:10.1038/ng.3335, published online 8 Jun. 2015; Guo et al., Nat. Commun. 9:1520 (2018). CTCF binding results in recognizable patterns in cfDNA that can be detected by sequencing, e.g., through fragment length analysis. Details regarding sequencing-based fragment length analysis are provided in Snyder et al., Cell 164:57-68 (2016); WO 2018/009723; and US20170211143A1, each of which are incorporated herein by reference.

Thus, perturbations of CTCF binding result in variation in the fragmentation patterns of cfDNA. As such, CTCF binding sites represent a type of fragmentation variable target regions.

There are many known CTCF binding sites. See, e.g., the CTCFBSDB (CTCF Binding Site Database), available on the Internet at insulatordb.uthsc.edu/; Cuddapah et al., Genome Res. 19:24-32 (2009); Martin et al., Nat. Struct. Mol. Biol. 18:708-14 (2011); Rhee et al., Cell. 147:1408-19 (2011), each of which are incorporated by reference. Exemplary CTCF binding sites are at nucleotides 56014955-56016161 on chromosome 8 and nucleotides 95359169-95360473 on chromosome 13.

Accordingly, in some embodiments, the epigenetic target region set includes CTCF binding regions. In some embodiments, the CTCF binding regions comprise at least 10, 20, 50, 100, 200, or 500 CTCF binding regions, or 10-20, 20-50, 50-100, 100-200, 200-500, or 500-1000 CTCF binding regions, e.g., such as CTCF binding regions described above or in one or more of CTCFBSDB or the Cuddapah et al., Martin et al., or Rhee et al. articles cited above.

In some embodiments, at least some of the CTCF sites can be methylated or unmethylated, wherein the methylation state is correlated with the whether or not the cell is a cancer cell. In some embodiments, the epigenetic target region set comprises at least 100 bp, at least 200 bp, at least 300 bp, at least 400 bp, at least 500 bp, at least 750 bp, at least 1000 bp upstream and downstream regions of the CTCF binding sites.

iv. Transcription Start Sites

Transcription start sites may also show perturbations in neoplastic cells. For example, nucleosome organization at various transcription start sites in healthy cells of the hematopoietic lineage—which contributes substantially to cfDNA in healthy individuals—may differ from nucleosome organization at those transcription start sites in neoplastic cells. This results in different cfDNA patterns that can be detected by sequencing, as discussed generally in Snyder et al., Cell 164:57-68 (2016); WO 2018/009723; and US20170211143A1. In another example, transcription start sites that do not necessarily differ epigenetically in cancerous tissue relative to DNA from healthy tissue of the same type, but do differ epigenetically (e.g., with respect to nucleosome organization) relative to cfDNA that is typical in healthy subjects. Where, for example, the presence of a cancer results in increased cell death such as apoptosis of cells of the tissue type corresponding to the cancer, such a cancer can be detected at least in part using such transcription start sites.

Thus, perturbations of transcription start sites also result in variation in the fragmentation patterns of cfDNA. As such, transcription start sites also represent a type of fragmentation variable target regions.

Human transcriptional start sites are available from DBTSS (DataBase of Human Transcription Start Sites), available on the Internet at dbtss.hgc.jp and described in Yamashita et al., Nucleic Acids Res. 34(Database issue): D86-D89 (2006), which is incorporated herein by reference.

Accordingly, in some embodiments, the epigenetic target region set includes transcriptional start sites. In some embodiments, the transcriptional start sites comprise at least 10, 20, 50, 100, 200, or 500 transcriptional start sites, or 10-20, 20-50, 50-100, 100-200, 200-500, or 500-1000 transcriptional start sites, e.g., such as transcriptional start sites listed in DBTSS. In some embodiments, at least some of the transcription start sites can be methylated or unmethylated, wherein the methylation state is correlated with whether or not the cell is a cancer cell. In some embodiments, the epigenetic target region set comprises at least 100 bp, at least 200 bp, at least 300 bp, at least 400 bp, at least 500 bp, at least 750 bp, at least 1000 bp upstream and downstream regions of the transcription start sites.

v. Focal Amplifications

Although focal amplifications are somatic mutations, they can be detected by sequencing based on read frequency in a manner analogous to approaches for detecting certain epigenetic changes such as changes in methylation. As such, regions that may show focal amplifications in cancer can be included in the epigenetic target region set and may comprise one or more of AR, BRAF, CCND1, CCND2, CCNE1, CDK4, CDK6, EGFR, ERBB2, FGFR1, FGFR2, KIT, KRAS, MET, MYC, PDGFRA, PIK3CA, and RAF1. For example, in some embodiments, the epigenetic target region set comprises at least 2, 3, 4, 5, 6, 7, 8, 9, 10, 11, 12, 13, 14, 15, 16, 17, or 18 of the foregoing targets.

vi. Methylation Control Regions

It can be useful to include control regions to facilitate data validation. In some embodiments, the epigenetic target region set includes control regions that are expected to be methylated or unmethylated in essentially all samples, regardless of whether the DNA is derived from a cancer cell or a normal cell. In some embodiments, the epigenetic target region set includes control hypomethylated regions that are expected to be hypomethylated in essentially all samples. In some embodiments, the epigenetic target region set includes control hypermethylated regions that are expected to be hypermethylated in essentially all samples.

b. Sequence-Variable Target Region Set

In some embodiments, the sequence-variable target region set comprises a plurality of regions known to undergo somatic mutations in cancer.

In some aspects, the sequence-variable target region set targets a plurality of different genes or genomic regions ("panel") selected such that a determined proportion of subjects having a cancer exhibits a genetic variant or tumor marker in one or more different genes or genomic regions in the panel. The panel may be selected to limit a region for sequencing to a fixed number of base pairs. The panel may be selected to sequence a desired amount of DNA, e.g., by adjusting the affinity and/or amount of the probes as described elsewhere herein. The panel may be further selected to achieve a desired sequence read depth. The panel may be selected to achieve a desired sequence read depth or sequence read coverage for an amount of sequenced base pairs. The panel may be selected to achieve a theoretical sensitivity, a theoretical specificity, and/or a theoretical accuracy for detecting one or more genetic variants in a sample.

Probes for detecting the panel of regions can include those for detecting genomic regions of interest (hotspot regions) as well as nucleosome-aware probes (e.g., KRAS codons 12 and 13) and may be designed to optimize capture based on analysis of cfDNA coverage and fragment size variation impacted by nucleosome binding patterns and GC sequence composition. Regions used herein can also include non-hotspot regions optimized based on nucleosome positions and GC models.

Examples of listings of genomic locations of interest may be found in Table 3 and Table 4. In some embodiments, a sequence-variable target region set used in the methods of the present disclosure comprises at least a portion of at least 5, at least 10, at least 15, at least 20, at least 25, at least 30, at least 35, at least 40, at least 45, at least 50, at least 55, at least 60, at least 65, or 70 of the genes of Table 3. In some embodiments, a sequence-variable target region set used in the methods of the present disclosure comprises at least 5, at least 10, at least 15, at least 20, at least 25, at least 30, at least 35, at least 40, at least 45, at least 50, at least 55, at least 60, at least 65, or 70 of the SNVs of Table 3. In some embodiments, a sequence-variable target region set used in the methods of the present disclosure comprises at least 1, at least 2, at least 3, at least 4, at least 5, or 6 of the fusions of Table 3. In some embodiments, a sequence-variable target region set used in the methods of the present disclosure comprise at least a portion of at least 1, at least 2, or 3 of the indels of Table 3. In some embodiments, a sequence-variable target region set used in the methods of the present disclosure comprises at least a portion of at least 5, at least 10, at least 15, at least 20, at least 25, at least 30, at least 35, at least 40, at least 45, at least 50, at least 55, at least 60, at least 65, at least 70, or 73 of the genes of Table 4. In some embodiments, a sequence-variable target region set used in the methods of the present disclosure comprises at least 5, at least 10, at least 15, at least 20, at least 25, at least 30, at least 35, at least 40, at least 45, at least 50, at least 55, at least 60, at least 65, at least 70, or 73 of the SNVs of Table 4. In some embodiments, a sequence-variable target region set used in the methods of the present disclosure comprises at least 1, at least 2, at least 3, at least 4, at least 5, or 6 of the fusions of Table 4. In some embodiments, a sequence-variable target region set used in the methods of the present disclosure comprises at least a portion of at least 1, at least 2, at least 3, at least 4, at least 5, at least 6, at least 7, at least 8, at least 9, at least 10, at least 11, at least 12, at least 13, at least 14, at least 15, at least 16, at least 17, or 18 of the indels of Table 4. Each of these genomic locations of interest may be identified as a backbone region or hot-spot region for a given panel. An example of a listing of hot-spot genomic locations of interest may be found in Table 5. In some embodiments, a sequence-variable target region set used in the methods of the present disclosure comprises at least a portion of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 of the genes of Table 5. Each hot-spot genomic region is listed with several characteristics, including the associated gene, chromosome on which it resides, the start and stop position of the genome representing the gene's locus, the length of the gene's locus in base pairs, the exons covered by the gene, and the critical feature (e.g., type of mutation) that a given genomic region of interest may seek to capture.

TABLE 3

| Point Mutations (SNVs) | | | | | | Fusions |
|---|---|---|---|---|---|---|
| AKT1 | ALK | APC | AR | ARAF | ARID1A | ALK |
| ATM | BRAF | BRCA1 | BRCA2 | CCND1 | CCND2 | FGFR2 |
| CCNE1 | CDH1 | CDK4 | CDK6 | CDKN2A | CDKN2B | FGFR3 |
| CTNNB1 | EGFR | ERBB2 | ESR1 | EZH2 | FBXW7 | NTRK1 |
| FGFR1 | FGFR2 | FGFR3 | GATA3 | GNA11 | GNAQ | RET |
| GNAS | HNF1A | HRAS | IDH1 | IDH2 | JAK2 | ROS1 |
| JAK3 | KIT | KRAS | MAP2K1 | MAP2K2 | MET | |
| MLH1 | MPL | MYC | NF1 | NFE2L2 | NOTCH1 | |
| NPM1 | NRAS | NTRK1 | PDGFRA | PIK3CA | PTEN | |
| PTPN11 | RAF1 | RB1 | RET | RHEB | RHOA | |
| RIT1 | ROS1 | SMAD4 | SMO | SRC | STK11 | |
| TERT | TP53 | TSC1 | VHL | | | |

TABLE 4

| Point Mutations (SNVs) | | | | | | Fusions |
|---|---|---|---|---|---|---|
| AKT1 | ALK | APC | AR | ARAF | ARID1A | ALK |
| ATM | BRAF | BRCA1 | BRCA2 | CCND1 | CCND2 | FGFR2 |
| CCNE1 | CDH1 | CDK4 | CDK6 | CDKN2A | DDR2 | FGFR3 |
| CTNNB1 | EGFR | ERBB2 | ESR1 | EZH2 | FBXW7 | NTRK1 |
| FGFR1 | FGFR2 | FGFR3 | GATA3 | GNA11 | GNAQ | RET |
| GNAS | HNF1A | HRAS | IDH1 | IDH2 | JAK2 | ROS1 |
| JAK3 | KIT | KRAS | MAP2K1 | MAP2K2 | MET | |
| MLH1 | MPL | MYC | NF1 | NFE2L2 | NOTCH1 | |
| NPM1 | NRAS | NTRK1 | PDGFRA | PIK3CA | PTEN | |
| PTPN11 | RAF1 | RB1 | RET | RHEB | RHOA | |
| RIT1 | ROS1 | SMAD4 | SMO | MAPK1 | STK11 | |
| TERT | TP53 | TSC1 | VHL | MAPK3 | MTOR | |
| NTRK3 | | | | | | |

TABLE 5

| Gene | Chromosome | Start Position | Stop Position | Length (bp) | Exons Covered | Critical Feature |
|---|---|---|---|---|---|---|
| ALK | chr2 | 29446405 | 29446655 | 250 | intron 19 | Fusion |
| ALK | chr2 | 29446062 | 29446197 | 135 | intron 20 | Fusion |
| ALK | chr2 | 29446198 | 29446404 | 206 | 20 | Fusion |
| ALK | chr2 | 29447353 | 29447473 | 120 | intron 19 | Fusion |
| ALK | chr2 | 29447614 | 29448316 | 702 | intron 19 | Fusion |
| ALK | chr2 | 29448317 | 29448441 | 124 | 19 | Fusion |
| ALK | chr2 | 29449366 | 29449777 | 411 | intron 18 | Fusion |
| ALK | chr2 | 29449778 | 29449950 | 172 | 18 | Fusion |
| BRAF | chr7 | 140453064 | 140453203 | 139 | 15 | BRAF V600 |
| CTNNB1 | chr3 | 41266007 | 41266254 | 247 | 3 | S37 |
| EGFR | chr7 | 55240528 | 55240827 | 299 | 18 and 19 | G719 and deletions |
| EGFR | chr7 | 55241603 | 55241746 | 143 | 20 | Insertions/T790M |
| EGFR | chr7 | 55242404 | 55242523 | 119 | 21 | L858R |
| ERBB2 | chr17 | 37880952 | 37881174 | 222 | 20 | Insertions |
| ESR1 | chr6 | 152419857 | 152420111 | 254 | 10 | V534, P535, L536, Y537, D538 |
| FGFR2 | chr10 | 123279482 | 123279693 | 211 | 6 | S252 |
| GATA3 | chr10 | 8111426 | 8111571 | 145 | 5 | SS/Indels |
| GATA3 | chr10 | 8115692 | 8116002 | 310 | 6 | SS/Indels |
| GNAS | chr20 | 57484395 | 57484488 | 93 | 8 | R844 |
| IDH1 | chr2 | 209113083 | 209113394 | 311 | 4 | R132 |
| IDH2 | chr15 | 90631809 | 90631989 | 180 | 4 | R140, R172 |
| KIT | chr4 | 55524171 | 55524258 | 87 | 1 | |
| KIT | chr4 | 55561667 | 55561957 | 290 | 2 | |
| KIT | chr4 | 55564439 | 55564741 | 302 | 3 | |
| KIT | chr4 | 55565785 | 55565942 | 157 | 4 | |
| KIT | chr4 | 55569879 | 55570068 | 189 | 5 | |
| KIT | chr4 | 55573253 | 55573463 | 210 | 6 | |
| KIT | chr4 | 55575579 | 55575719 | 140 | 7 | |
| KIT | chr4 | 55589739 | 55589874 | 135 | 8 | |
| KIT | chr4 | 55592012 | 55592226 | 214 | 9 | |
| KIT | chr4 | 55593373 | 55593718 | 345 | 10 and 11 | 557, 559, 560, 576 |
| KIT | chr4 | 55593978 | 55594297 | 319 | 12 and 13 | V654 |
| KIT | chr4 | 55595490 | 55595661 | 171 | 14 | T670, S709 |
| KIT | chr4 | 55597483 | 55597595 | 112 | 15 | D716 |
| KIT | chr4 | 55598026 | 55598174 | 148 | 16 | L783 |
| KIT | chr4 | 55599225 | 55599368 | 143 | 17 | C809, R815, D816, L818, D820, S821F, N822, Y823 |
| KIT | chr4 | 55602653 | 55602785 | 132 | 18 | A829P |
| KIT | chr4 | 55602876 | 55602996 | 120 | 19 | |
| KIT | chr4 | 55603330 | 55603456 | 126 | 20 | |
| KIT | chr4 | 55604584 | 55604733 | 149 | 21 | |
| KRAS | chr12 | 25378537 | 25378717 | 180 | 4 | A146 |
| KRAS | chr12 | 25380157 | 25380356 | 199 | 3 | Q61 |
| KRAS | chr12 | 25398197 | 25398328 | 131 | 2 | G12/G13 |
| MET | chr7 | 116411535 | 116412255 | 720 | 13, 14, intron 13, intron 14 | MET exon 14 SS |
| NRAS | chr1 | 115256410 | 115256609 | 199 | 3 | Q61 |
| NRAS | chr1 | 115258660 | 115258791 | 131 | 2 | G12/G13 |
| PIK3CA | chr3 | 178935987 | 178936132 | 145 | 10 | E545K |
| PIK3CA | chr3 | 178951871 | 178952162 | 291 | 21 | H1047R |
| PTEN | chr10 | 89692759 | 89693018 | 259 | 5 | R130 |
| SMAD4 | chr18 | 48604616 | 48604849 | 233 | 12 | D537 |
| TERT | chr5 | 1294841 | 1295512 | 671 | promoter | chr5: 1295228 |
| TP53 | chr17 | 7573916 | 7574043 | 127 | 11 | Q331, R337, R342 |
| TP53 | chr17 | 7577008 | 7577165 | 157 | 8 | R273 |
| TP53 | chr17 | 7577488 | 7577618 | 130 | 7 | R248 |
| TP53 | chr17 | 7578127 | 7578299 | 172 | 6 | R213/Y220 |
| TP53 | chr17 | 7578360 | 7578564 | 204 | 5 | R175/Deletions |
| TP53 | chr17 | 7579301 | 7579600 | 299 | 4 | |
| | | | | 12574 (total target region) | | |
| | | | | 16330 (total probe coverage) | | |

Additionally or alternatively, suitable target region sets are available from the literature. For example, Gale et al., PLoS One 13: e0194630 (2018), which is incorporated herein by reference, describes a panel of 35 cancer-related gene targets that can be used as part or all of a sequence-variable target region set. These 35 targets are AKT1, ALK, BRAF, CCND1, CDK2A, CTNNB1, EGFR, ERBB2, ESR1, FGFR1, FGFR2, FGFR3, FOXL2, GATA3, GNA11, GNAQ, GNAS, HRAS, IDH1, IDH2, KIT, KRAS, MED12, MET, MYC, NFE2L2, NRAS, PDGFRA, PIK3CA, PPP2R1A, PTEN, RET, STK11, TP53, and U2AF1.

In some embodiments, the sequence-variable target region set comprises target regions from at least 10, 20, 30, or 35 cancer-related genes, such as the cancer-related genes listed above.

In some embodiments, the sequence-variable target region set has a footprint of at least 50 kbp, e.g., at least 100 kbp, at least 200 kbp, at least 300 kbp, or at least 400 kbp. In some embodiments, the sequence-variable target region set has a footprint in the range of 100-2000 kbp, e.g., 100-200 kbp, 200-300 kbp, 300-400 kbp, 400-500 kbp, 500-600 kbp, 600-700 kbp, 700-800 kbp, 800-900 kbp, 900-1,000 kbp, 1-1.5 Mbp or 1.5-2 Mbp. In some embodiments, the sequence-variable target region set has a footprint of at least 2 Mbp.

7. Subjects

In some embodiments, the DNA (e.g., cfDNA) is obtained from a subject having a cancer. In some embodiments, the DNA (e.g., cfDNA) is obtained from a subject suspected of having a cancer. In some embodiments, the DNA (e.g., cfDNA) is obtained from a subject having a tumor. In some embodiments, the DNA (e.g., cfDNA) is obtained from a subject suspected of having a tumor. In some embodiments, the DNA (e.g., cfDNA) is obtained from a subject having neoplasia. In some embodiments, the DNA (e.g., cfDNA) is obtained from a subject suspected of having neoplasia. In some embodiments, the DNA (e.g., cfDNA) is obtained from a subject in remission from a tumor, cancer, or neoplasia (e.g., following chemotherapy, surgical resection, radiation, or a combination thereof). In any of the foregoing embodiments, the cancer, tumor, or neoplasia or suspected cancer, tumor, or neoplasia may be of the lung, colon, rectum, kidney, breast, prostate, or liver. In some embodiments, the cancer, tumor, or neoplasia or suspected cancer, tumor, or neoplasia is of the lung. In some embodiments, the cancer, tumor, or neoplasia or suspected cancer, tumor, or neoplasia is of the colon or rectum. In some embodiments, the cancer, tumor, or neoplasia or suspected cancer, tumor, or neoplasia is of the breast. In some embodiments, the cancer, tumor, or neoplasia or suspected cancer, tumor, or neoplasia is of the prostate. In any of the foregoing embodiments, the subject may be a human subject.

8. Pooling of DNA from First and Second Subsamples or Portions Thereof.

In some embodiments, the methods comprise preparing a pool comprising at least a portion of the DNA of the treated subsample or second subsample (also referred to as the hypomethylated partition) and at least a portion of the DNA of the first subsample or additional treated subsample (also referred to as the hypermethylated partition). Target regions, e.g., including epigenetic target regions and/or sequence-variable target regions, may be captured from the pool. The steps of capturing a target region set from at least a portion of a subsample described elsewhere herein encompass capture steps performed on a pool comprising DNA from the first and second subsamples. A step of amplifying DNA in the pool may be performed before capturing target regions from the pool. The capturing step may have any of the features described for capturing steps elsewhere herein.

The epigenetic target regions may show differences in methylation levels and/or fragmentation patterns depending on whether they originated from a tumor or from healthy cells, or what type of tissue they originated from, as discussed elsewhere herein. The sequence-variable target regions may show differences in sequence depending on whether they originated from a tumor or from healthy cells.

Analysis of epigenetic target regions from the hypomethylated partition may be less informative in some applications than analysis of sequence-variable target-regions from the hypermethylated and hypomethylated partitions and epigenetic target regions from the hypermethylated partition. As such, in methods where sequence-variable target-regions and epigenetic target regions are being captured, the latter may be captured to a lesser extent than one or more of the sequence-variable target-regions from the hypermethylated and hypomethylated partitions and epigenetic target regions from the hypermethylated partition. For example, sequence-variable target regions can be captured from the portion of the hypomethylated partition not pooled with the hypermethylated partition, and the pool can be prepared with some (e.g., a majority, substantially all, or all) of the DNA from the hypermethylated partition and none or some (e.g., a minority) of the DNA from the hypomethylated partition. Such approaches can reduce or eliminate sequencing of epigenetic target regions from the hypomethylated partition, thereby reducing the amount of sequencing data that suffices for further analysis.

In some embodiments, including a minority of the DNA of the hypomethylated partition in the pool facilitates quantification of one or more epigenetic features (e.g., methylation or other epigenetic feature(s) discussed in detail elsewhere herein), e.g., on a relative basis.

In some embodiments, the pool comprises a minority of the DNA of the hypomethylated partition, e.g., less than about 50% of the DNA of the hypomethylated partition, such as less than or equal to about 45%, 40%, 35%, 30%, 25%, 20%, 15%, 10%, or 5% of the DNA of the hypomethylated partition. In some embodiments, the pool comprises about 5%-25% of the DNA of the hypomethylated partition. In some embodiments, the pool comprises about 10%-20% of the DNA of the hypomethylated partition. In some embodiments, the pool comprises about 10% of the DNA of the hypomethylated partition. In some embodiments, the pool comprises about 15% of the DNA of the hypomethylated partition. In some embodiments, the pool comprises about 20% of the DNA of the hypomethylated partition.

In some embodiments, the pool comprises a portion of the hypermethylated partition, which may be at least about 50% of the DNA of the hypermethylated partition. For example, the pool may comprise at least about 55%, 60%, 65%, 70%, 75%, 80%, 85%, 90%, or 95% of the DNA of the hypermethylated partition. In some embodiments, the pool comprises 50-55%, 55-60%, 60-65%, 65-70%, 70-75%, 75-80%, 80-85%, 85-90%, 90-95%, or 95-100% of the DNA of the hypermethylated partition. In some embodiments, the second pool comprises all or substantially all of the hypermethylated partition.

In some embodiments, the methods comprise preparing a first pool comprising at least a portion of the DNA of the hypomethylated partition. In some embodiments, the methods comprise preparing a second pool comprising at least a portion of the DNA of the hypermethylated partition. In some embodiments, the first pool further comprises a portion of the DNA of the hypermethylated partition. In some embodiments, the second pool further comprises a portion of the DNA of the hypomethylated partition. In some embodiments, the first pool comprises a majority of the DNA of the hypomethylated partition, and optionally and a minority of the DNA of the hypermethylated partition. In some embodiments, the second pool comprises a majority of the DNA of the hypermethylated partition and a minority of the DNA of the hypomethylated partition. In some embodiments involving an intermediately methylated partition, the second pool comprises at least a portion of the DNA of the intermediately methylated partition, e.g., a majority of the DNA of the intermediately methylated partition. In some embodiments, the first pool comprises a majority of the DNA of the hypomethylated partition, and the second pool comprises a majority of the DNA of the hypermethylated partition and a majority of the DNA of the intermediately methylated partition.

In some embodiments, the methods comprise capturing at least a first set of target regions from the first pool, e.g., wherein the first pool is as set forth in any of the embodiments above. In some embodiments, the first set comprises sequence-variable target regions. In some embodiments, the first set comprises hypomethylation variable target regions and/or fragmentation variable target regions. In some embodiments, the first set comprises sequence-variable target regions and fragmentation variable target regions. In some embodiments, the first set comprises sequence-variable target regions, hypomethylation variable target regions and fragmentation variable target regions. A step of amplifying DNA in the first pool may be performed before this capture step. In some embodiments, capturing the first set of target regions from the first pool comprises contacting the DNA of the first pool with a first set of target-specific probes. In some embodiments, the first set of target-specific probes comprises target-binding probes specific for the sequence-variable target regions. In some embodiments, the first set of target-specific probes comprises target-binding probes specific for the sequence-variable target regions, hypomethylation variable target regions and/or fragmentation variable target regions.

In some embodiments, the methods comprise capturing a second set of target regions or plurality of sets of target regions from the second pool, e.g., wherein the first pool is as set forth in any of the embodiments above. In some embodiments, the second plurality comprises epigenetic target regions, such as hypermethylation variable target regions and/or fragmentation variable target regions. In some embodiments, the second plurality comprises sequence-variable target regions and epigenetic target regions, such as hypermethylation variable target regions and/or fragmentation variable target regions. A step of amplifying DNA in the second pool may be performed before this capture step. In some embodiments, capturing the second plurality of sets of target regions from the second pool comprises contacting the DNA of the first pool with a second set of target-specific probes, wherein the second set of target-specific probes comprises target-binding probes specific for the sequence-variable target regions and target-binding probes specific for the epigenetic target regions. In some embodiments, the first set of target regions and the second set of target regions are not identical. For example, the first set of target regions may comprise one or more target regions not present in the second set of target regions. Alternatively or in addition, the second set of target regions may comprise one or more target regions not present in the first set of target regions. In some embodiments, at least one hypermethylation variable target region is captured from the second pool but not from the first pool. In some embodiments, a plurality of hypermethylation variable target regions are captured from the second pool but not from the first pool. In some embodiments, the first set of target regions comprises sequence-variable target regions and/or the second set of target regions comprises epigenetic target regions. In some embodiments, the first set of target regions comprises sequence-variable target regions, and fragmentation variable target regions; and the second set of target regions comprises epigenetic target regions, such as hypermethylation variable target regions and fragmentation variable target regions. In some embodiments, the first set of target regions comprises sequence-variable target regions, fragmentation variable target regions, and comprises hypomethylation variable target regions; and the second set of target regions comprises epigenetic target regions, such as hypermethylation variable target regions and fragmentation variable target regions.

In some embodiments, the first pool comprises a majority of the DNA of the hypomethylated partition and a portion of the DNA of the hypermethylated partition (e.g., about half), and the second pool comprises a portion of the DNA of the hypermethylated partition (e.g., about half). In some such embodiments, the first set of target regions comprises sequence-variable target regions and/or the second set of target regions comprises epigenetic target regions. The sequence-variable target regions and/or the epigenetic target regions may be as set forth in any of the embodiments described elsewhere herein.

9. Sequencing

In general, sample nucleic acids flanked by adapters with or without prior amplification can be subject to sequencing. Sequencing methods include, for example, Sanger sequencing, high-throughput sequencing, pyrosequencing, sequencing-by-synthesis, single-molecule sequencing, nanopore sequencing, semiconductor sequencing, sequencing-by-ligation, sequencing-by-hybridization, Digital Gene Expression (Helicos), Next generation sequencing (NGS), Single Molecule Sequencing by Synthesis (SMSS) (Helicos), massively-parallel sequencing, Clonal Single Molecule Array (Solexa), shotgun sequencing, Ion Torrent, Oxford Nanopore, Roche Genia, Maxim-Gilbert sequencing, primer walking, and sequencing using PacBio, SOLiD, Ion Torrent, or Nanopore platforms. Sequencing reactions can be performed in a variety of sample processing units, which may multiple lanes, multiple channels, multiple wells, or other mean of processing multiple sample sets substantially simultaneously. Sample processing unit can also include multiple sample chambers to enable processing of multiple runs simultaneously.

In some embodiments, a sequencing step is performed on a library comprising captured set of target regions, which may comprise any of the target region sets described herein. In some embodiments, a sequencing step is performed on a library comprising a subsample that has not undergone capture/enrichment (e.g., a whole genome subsample). For example, target regions may be captured from the first subsample and the second sample and then sequenced; or target regions may be captured from the first subsample and combined with the second subsample after processing such as contacting and tagging steps; or target regions may be captured from the second subsample and combined with the first subsample after processing such as contacting and tagging steps; or both the first and second subsamples may be processed and combined without undergoing capture/enrichment.

The sequencing reactions can be performed on one or more forms of nucleic acids at least one of which is known to contain markers of cancer or of other disease. The sequencing reactions can also be performed on any nucleic acid fragments present in the sample. In some embodiments, sequence coverage of the genome may be less than 5%, 10%, 15%, 20%, 25%, 30%, 40%, 50%, 60%, 70%, 80%, 90%, 95%, 99%, 99.9% or 100%. In some embodiments, the sequence reactions may provide for sequence coverage of at least 5%, 10%, 15%, 20%, 25%, 30%, 40%, 50%, 60%, 70%, or 80% of the genome. Sequence coverage can performed on at least 5, 10, 20, 70, 100, 200 or 500 different genes, or at most 5000, 2500, 1000, 500 or 100 different genes.

Simultaneous sequencing reactions may be performed using multiplex sequencing. In some cases, cell-free nucleic acids may be sequenced with at least 1000, 2000, 3000, 4000, 5000, 6000, 7000, 8000, 9000, 10000, 50000, 100,000 sequencing reactions. In other cases cell-free nucleic acids may be sequenced with less than 1000, 2000, 3000, 4000, 5000, 6000, 7000, 8000, 9000, 10000, 50000, 100,000 sequencing reactions. Sequencing reactions may be performed sequentially or simultaneously. Subsequent data analysis may be performed on all or part of the sequencing reactions. In some cases, data analysis may be performed on at least 1000, 2000, 3000, 4000, 5000, 6000, 7000, 8000, 9000, 10000, 50000, 100,000 sequencing reactions. In other cases, data analysis may be performed on less than 1000, 2000, 3000, 4000, 5000, 6000, 7000, 8000, 9000, 10000, 50000, 100,000 sequencing reactions. An exemplary read depth is 1000-50000 reads per locus (base).

a. Differential Depth of Sequencing

In some embodiments, nucleic acids corresponding to the sequence-variable target region set are sequenced to a greater depth of sequencing than nucleic acids corresponding to the epigenetic target region set. For example, the depth of sequencing for nucleic acids corresponding to the sequence variant target region set may be at least 1.25-, 1.5-, 1.75-, 2-, 2.25-, 2.5-, 2.75-, 3-, 3.5-, 4-, 4.5-, 5-, 6-, 7-, 8-, 9-, 10-, 11-, 12-, 13-, 14-, or 15-fold greater, or 1.25- to 1.5-, 1.5- to 1.75-, 1.75- to 2-, 2- to 2.25-, 2.25- to 2.5-, 2.5- to 2.75-, 2.75- to 3-, 3- to 3.5-, 3.5- to 4-, 4- to 4.5-, 4.5- to 5-, 5- to 5.5-, 5.5- to 6-, 6- to 7-, 7- to 8-, 8- to 9-, 9- to 10-, 10- to 11-, 11- to 12-, 13- to 14-, 14- to 15-fold, or 15- to 100-fold greater, than the depth of sequencing for nucleic acids corresponding to the epigenetic target region set. In some embodiments, said depth of sequencing is at least 2-fold greater. In some embodiments, said depth of sequencing is at least 5-fold greater. In some embodiments, said depth of sequencing is at least 10-fold greater. In some embodiments, said depth of sequencing is 4- to 10-fold greater. In some embodiments, said depth of sequencing is 4- to 100-fold greater. Each of these embodiments refer to the extent to which nucleic acids corresponding to the sequence-variable target region set are sequenced to a greater depth of sequencing than nucleic acids corresponding to the epigenetic target region set.

In some embodiments, the captured cfDNA corresponding to the sequence-variable target region set and the captured cfDNA corresponding to the epigenetic target region set are sequenced concurrently, e.g., in the same sequencing cell (such as the flow cell of an Illumina sequencer) and/or in the same composition, which may be a pooled composition resulting from recombining separately captured sets or a composition obtained by capturing the cfDNA corresponding to the sequence-variable target region set and the captured cfDNA corresponding to the epigenetic target region set in the same vessel.

10. Analysis

In some embodiments, a method described herein comprises identifying the presence of DNA produced by a tumor (or neoplastic cells, or cancer cells).

The present methods can be used to diagnose presence of conditions, particularly cancer, in a subject, to characterize conditions (e.g., staging cancer or determining heterogeneity of a cancer), monitor response to treatment of a condition, effect prognosis risk of developing a condition or subsequent course of a condition. The present disclosure can also be useful in determining the efficacy of a particular treatment option. Successful treatment options may increase the amount of copy number variation or rare mutations detected in subject's blood if the treatment is successful as more cancers may die and shed DNA. In other examples, this may not occur. In another example, perhaps certain treatment options may be correlated with genetic profiles of cancers over time. This correlation may be useful in selecting a therapy.

Additionally, if a cancer is observed to be in remission after treatment, the present methods can be used to monitor residual disease or recurrence of disease.

The types and number of cancers that may be detected may include blood cancers, brain cancers, lung cancers, skin cancers, nose cancers, throat cancers, liver cancers, bone cancers, lymphomas, pancreatic cancers, skin cancers, bowel cancers, rectal cancers, thyroid cancers, bladder cancers, kidney cancers, mouth cancers, stomach cancers, solid state tumors, heterogeneous tumors, homogenous tumors and the like. Type and/or stage of cancer can be detected from genetic variations including mutations, rare mutations, indels, copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns, and abnormal changes in nucleic acid 5-methylcytosine.

Genetic data can also be used for characterizing a specific form of cancer. Cancers are often heterogeneous in both composition and staging. Genetic profile data may allow characterization of specific sub-types of cancer that may be important in the diagnosis or treatment of that specific sub-type. This information may also provide a subject or practitioner clues regarding the prognosis of a specific type of cancer and allow either a subject or practitioner to adapt treatment options in accord with the progress of the disease. Some cancers can progress to become more aggressive and genetically unstable. Other cancers may remain benign, inactive or dormant. The system and methods of this disclosure may be useful in determining disease progression.

Further, the methods of the disclosure may be used to characterize the heterogeneity of an abnormal condition in a subject. Such methods can include, e.g., generating a genetic profile of extracellular polynucleotides derived from the subject, wherein the genetic profile comprises a plurality of data resulting from copy number variation and rare mutation analyses. In some embodiments, an abnormal condition is cancer. In some embodiments, the abnormal condition may be one resulting in a heterogeneous genomic population. In the example of cancer, some tumors are known to comprise tumor cells in different stages of the cancer. In other examples, heterogeneity may comprise multiple foci of disease. Again, in the example of cancer, there may be multiple tumor foci, perhaps where one or more foci are the result of metastases that have spread from a primary site.

The present methods can be used to generate or profile, fingerprint or set of data that is a summation of genetic information derived from different cells in a heterogeneous disease. This set of data may comprise copy number variation, epigenetic variation, and mutation analyses alone or in combination.

The present methods can be used to diagnose, prognose, monitor or observe cancers, or other diseases. In some embodiments, the methods herein do not involve the diagnosing, prognosing or monitoring a fetus and as such are not directed to non-invasive prenatal testing. In other embodiments, these methodologies may be employed in a pregnant subject to diagnose, prognose, monitor or observe cancers or other diseases in an unborn subject whose DNA and other polynucleotides may co-circulate with maternal molecules.

An exemplary method for molecular tag identification of MBD-bead partitioned libraries through NGS which includes a step of subjecting the second subsample to a procedure that affects a first nucleobase in the DNA differently from a second nucleobase in the DNA of the first subsample is as follows:

1. Physical partitioning of an extracted DNA sample (e.g., extracted blood plasma DNA from a human sample, which has optionally been subjected to target capture as described herein) using a methyl-binding domain protein-bead purification kit, saving all elutions from process for downstream processing.
2. Parallel application of differential molecular tags and NGS-enabling adapter sequences to each partition. For example, the hypermethylated, residual methylation ('wash'), and hypomethylated partitions are ligated with NGS-adapters with molecular tags.
3. Subject hypomethylated partition to a procedure that affects a first nucleobase in the DNA differently from a second nucleobase in the DNA, such as any of those described herein.
4. Re-combining all molecular tagged partitions, and subsequent amplification using adapter-specific DNA primer sequences.
5. Capture/hybridization of re-combined and amplified total library, targeting genomic regions of interest (e.g., cancer-specific genetic variants and differentially methylated regions).
6. Re-amplification of the captured DNA library, appending a sample tag. Different samples are pooled, and assayed in multiplex on an NGS instrument.
7. Bioinformatics analysis of NGS data, with the molecular tags being used to identify unique molecules, as well deconvolution of the sample into molecules that were differentially MBD-partitioned. This analysis can yield information on relative 5-methylcytosine for genomic regions, concurrent with standard genetic sequencing/variant detection.

In some embodiments of methods described herein, including but not limited to the method shown above, the molecular tags consist of nucleotides that are not altered by the procedure that affects a first nucleobase in the DNA differently from a second nucleobase in the DNA, such as any of those described herein (e.g., mC along with A, T, and G where the procedure is bisulfite conversion or any other conversion that does not affect mC; hmC along with A, T, and G where the procedure is a conversion that does not affect hmC; etc.). In some embodiments of methods described herein, including but not limited to the method shown above, the molecular tags do not comprise nucleotides that are altered by the procedure that affects a first nucleobase in the DNA differently from a second nucleobase in the DNA, such as any of those described herein (e.g., the tags do not comprise unmodified C where the procedure is bisulfite conversion or any other conversion that affects C; the tags do not comprise mC where the procedure is a conversion that affects mC; the tags do not comprise hmC where the procedure is a conversion that affects hmC; etc.).

In general, the procedure that affects a first nucleobase in the DNA differently from a second nucleobase in the DNA may instead be performed before the step of parallel application of differential molecular tags and NGS-enabling adapter sequences to each partition. For example, this may be done where the procedure that affects a first nucleobase in the DNA differently from a second nucleobase in the DNA is a separation, such as hmC-seal, and in such a case the separated populations may themselves be differentially tagged relative to each other. Such an exemplary method is as follows:

1. Physical partitioning of an extracted DNA sample (e.g., extracted blood plasma DNA from a human sample, which has optionally been subjected to target capture as described herein) using a methyl-binding domain protein-bead purification kit, saving all elutions from process for downstream processing.
2. Subject hypomethylated partition to a procedure that affects a first nucleobase in the DNA differently from a second nucleobase in the DNA, such as any of those described herein.
3. Parallel application of differential molecular tags and NGS-enabling adapter sequences to each partition. For example, the hypermethylated partition (or where applicable, two or more sub-partitions of the hypermethylated partition), residual methylation ('wash') partition, and hypomethylated partition are ligated with NGS-adapters with molecular tags.
4. Re-combining all molecular tagged partitions, and subsequent amplification using adapter-specific DNA primer sequences.
5. Capture/hybridization of re-combined and amplified total library, targeting genomic regions of interest (e.g., cancer-specific genetic variants and differentially methylated regions).
6. Re-amplification of the captured DNA library, appending a sample tag. Different samples are pooled, and assayed in multiplex on an NGS instrument.
7. Bioinformatics analysis of NGS data, with the molecular tags being used to identify unique molecules, as well deconvolution of the sample into molecules that were differentially MBD-partitioned. This analysis can yield information on relative 5-methylcytosine for genomic regions, concurrent with standard genetic sequencing/variant detection.

11. Exemplary Workflows

Exemplary workflows for partitioning and library preparation are provided herein. In some embodiments, some or all features of the partitioning and library preparation workflows may be used in combination.

a. Partitioning

In some embodiments, sample DNA (e.g., between 5 and 200 ng) is mixed with methyl binding domain (MBD) buffer and magnetic beads conjugated with MBD proteins and incubated overnight. Methylated DNA (hypermethylated DNA) binds the MBD protein on the magnetic beads during this incubation. Non-methylated (hypomethylated DNA) or less methylated DNA (intermediately methylated) is washed away from the beads with buffers containing increasing concentrations of salt. For example, one, two, or more fractions containing non-methylated, hypomethylated, and/or intermediately methylated DNA may be obtained from such washes. Finally, a high salt buffer is used to elute the heavily methylated DNA (hypermethylated DNA) from the MBD protein. In some embodiments, these washes result in three partitions (hypomethylated partition, intermediately methylated fraction and hypermethylated partition) of DNA having increasing levels of methylation.

In some embodiments, the three partitions of DNA are desalted and concentrated in preparation for the enzymatic steps of library preparation.

b. Library Preparation

In some embodiments (e.g., after concentrating the DNA in the partitions), the partitioned DNA is made ligatable, e.g., by extending the end overhangs of the DNA molecules are extended, and adding adenosine residues to the 3' ends of fragments and phosphorylating the 5' end of each DNA fragment. DNA ligase and adapters are added to ligate each partitioned DNA molecule with an adapter on each end. These adapters contain partition tags (e.g., non-random, non-unique barcodes) that are distinguishable from the partition tags in the adapters used in the other partitions. Either before or after making the portioned DNA ligatable and performing the ligation, the hypomethylated partition is subjected to a procedure that affects a first nucleobase in the DNA differently from a second nucleobase in the DNA, such as any of those described herein. Where the procedure that affects a first nucleobase in the DNA differently from a second nucleobase in the DNA further partitions the hypomethylated partition, the ligation of adapters should be performed after the procedure so that the sub-partitions of the hypomethylated partition can be differentially tagged. Optionally, the hypermethylated partition may be digested with a methylation-sensitive nuclease, such as a methylation-sensitive restriction enzyme (e.g., one or more, or each of HpaII, BstUI and Hin6i). Optionally, the hypermethylated partition may be subjected to a procedure that affects a first nucleobase in the DNA differently from a second nucleobase in the DNA, such as any of those described herein. Where the procedure that affects a first nucleobase in the DNA differently from a second nucleobase in the DNA further partitions the hypermethylated partition, the ligation of adapters should be performed after the procedure so that the sub-partitions of the hypermethylated partition can be differentially tagged. Then, the two, three, or more partitions are pooled together and are amplified (e.g., by PCR, such as with primers specific for the adapters).

Following PCR, amplified DNA may be cleaned and concentrated prior to enrichment. The amplified DNA is contacted with a collection of probes described herein (which may be, e.g., biotinylated RNA probes) that target specific regions of interest. The mixture is incubated, e.g., overnight, e.g., in a salt buffer. The probes are captured (e.g., using streptavidin magnetic beads) and separated from the amplified DNA that was not captured, such as by a series of salt washes, thereby enriching the sample. After the enrichment, the enriched sample is amplified by PCR. In some embodiments, the PCR primers contain a sample tag, thereby incorporating the sample tag into the DNA molecules. In some embodiments, DNA from different samples is pooled together and then multiplex sequenced, e.g., using an Illumina NovaSeq sequencer.

C. Additional Features of Certain Disclosed Methods

1. Samples

A sample can be any biological sample isolated from a subject. A sample can be a bodily sample. Samples can include body tissues, such as known or suspected solid tumors, whole blood, platelets, serum, plasma, stool, red blood cells, white blood cells or leucocytes, endothelial cells, tissue biopsies, cerebrospinal fluid synovial fluid, lymphatic fluid, ascites fluid, interstitial or extracellular fluid, the fluid in spaces between cells, including gingival crevicular fluid, bone marrow, pleural effusions, cerebrospinal fluid, saliva, mucous, sputum, semen, sweat, urine. Samples are preferably body fluids, particularly blood and fractions thereof, and urine. A sample can be in the form originally isolated from a subject or can have been subjected to further processing to remove or add components, such as cells, or enrich for one component relative to another. Thus, a preferred body fluid for analysis is plasma or serum containing cell-free nucleic acids. A sample can be isolated or obtained from a subject and transported to a site of sample analysis. The sample may be preserved and shipped at a desirable temperature, e.g., room temperature, 4° C., −20° C., and/or −80° C. A sample can be isolated or obtained from a subject at the site of the sample analysis. The subject can be a human, a mammal, an animal, a companion animal, a service animal, or a pet. The subject may have a cancer. The subject may not have cancer or a detectable cancer symptom. The subject may have been treated with one or more cancer therapy, e.g., any one or more of chemotherapies, antibodies, vaccines or biologies. The subject may be in remission. The subject may or may not be diagnosed of being susceptible to cancer or any cancer-associated genetic mutations/disorders.

The volume of plasma can depend on the desired read depth for sequenced regions. Exemplary volumes are 0.4-40 ml, 5-20 ml, 10-20 ml. For examples, the volume can be 0.5 mL, 1 mL, 5 mL 10 mL, 20 mL, 30 mL, or 40 mL. A volume of sampled plasma may be 5 to 20 mL.

A sample can comprise various amount of nucleic acid that contains genome equivalents. For example, a sample of about 30 ng DNA can contain about 10,000 ($10^4$) haploid human genome equivalents and, in the case of cfDNA, about 200 billion ($2 \times 10^{11}$) individual polynucleotide molecules. Similarly, a sample of about 100 ng of DNA can contain about 30,000 haploid human genome equivalents and, in the case of cfDNA, about 600 billion individual molecules.

A sample can comprise nucleic acids from different sources, e.g., from cells and cell-free of the same subject, from cells and cell-free of different subjects. A sample can comprise nucleic acids carrying mutations. For example, a sample can comprise DNA carrying germline mutations and/or somatic mutations. Germline mutations refer to mutations existing in germline DNA of a subject. Somatic mutations refer to mutations originating in somatic cells of a subject, e.g., cancer cells. A sample can comprise DNA carrying cancer-associated mutations (e.g., cancer-associated somatic mutations). A sample can comprise an epigenetic variant (i.e. a chemical or protein modification), wherein the epigenetic variant associated with the presence of a genetic variant such as a cancer-associated mutation. In some embodiments, the sample comprises an epigenetic variant associated with the presence of a genetic variant, wherein the sample does not comprise the genetic variant.

Exemplary amounts of cell-free nucleic acids in a sample before amplification range from about 1 fg to about 1 µg, e.g., 1 µg to 200 ng, 1 ng to 100 ng, 10 ng to 1000 ng. For example, the amount can be up to about 600 ng, up to about 500 ng, up to about 400 ng, up to about 300 ng, up to about 200 ng, up to about 100 ng, up to about 50 ng, or up to about 20 ng of cell-free nucleic acid molecules. The amount can be at least 1 fg, at least 10 fg, at least 100 fg, at least 1 pg, at least 10 pg, at least 100 pg, at least 1 ng, at least 10 ng, at least 100 ng, at least 150 ng, or at least 200 ng of cell-free nucleic acid molecules. The amount can be up to 1 femtogram (fg), 10 fg, 100 fg, 1 picogram (pg), 10 pg, 100 pg, 1 ng, 10 ng, 100 ng, 150 ng, or 200 ng of cell-free nucleic acid molecules. The method can comprise obtaining 1 femtogram (fg) to 200 ng-13141 Cell-free DNA refers to DNA not contained within a cell at the time of its isolation from a subject. For example, cfDNA can be isolated from a sample as the DNA remaining in the sample after removing intact cells, without lysing the cells or otherwise extracting intracellular DNA. Cell-free nucleic acids include DNA, RNA, and hybrids thereof, including genomic DNA, mitochondrial DNA, siRNA, miRNA, circulating RNA (cRNA), tRNA, rRNA, small nucleolar RNA (snoRNA), Piwi-interacting RNA (piRNA), long non-coding RNA (long ncRNA), or fragments of any of these. Cell-free nucleic acids can be double-stranded, single-stranded, or a hybrid thereof. A cell-free nucleic acid can be released into bodily fluid through secretion or cell death processes, e.g., cellular necrosis and apoptosis. Some cell-free nucleic acids are released into bodily fluid from cancer cells e.g., circulating tumor DNA, (ctDNA). Others are released from healthy cells. In some embodiments, cfDNA is cell-free fetal DNA (cffDNA) In some embodiments, cell free nucleic acids are produced by tumor cells. In some embodiments, cell free nucleic acids are produced by a mixture of tumor cells and non-tumor cells.

Cell-free nucleic acids have an exemplary size distribution of about 100-500 nucleotides, with molecules of 110 to about 230 nucleotides representing about 90% of molecules, with a mode of about 168 nucleotides and a second minor peak in a range between 240 to 440 nucleotides.

Cell-free nucleic acids can be isolated from bodily fluids through a fractionation or partitioning step in which cell-free nucleic acids, as found in solution, are separated from intact cells and other non-soluble components of the bodily fluid. Partitioning may include techniques such as centrifugation or filtration. Alternatively, cells in bodily fluids can be lysed and cell-free and cellular nucleic acids processed together. Generally, after addition of buffers and wash steps, nucleic acids can be precipitated with an alcohol. Further clean up steps may be used such as silica based columns to remove contaminants or salts. Non-specific bulk carrier nucleic acids, such as C 1 DNA, DNA or protein for bisulfite sequencing, hybridization, and/or ligation, may be added throughout the reaction to optimize certain aspects of the procedure such as yield.

After such processing, samples can include various forms of nucleic acid including double stranded DNA, single stranded DNA and single stranded RNA. In some embodiments, single stranded DNA and RNA can be converted to double stranded forms so they are included in subsequent processing and analysis steps.

Double-stranded DNA molecules in a sample and single stranded nucleic acid molecules converted to double stranded DNA molecules can be linked to adapters at either one end or both ends. Typically, double stranded molecules are blunt ended by treatment with a polymerase with a 5'-3' polymerase and a 3 '-5' exonuclease (or proof reading function), in the presence of all four standard nucleotides. Klenow large fragment and T4 polymerase are examples of suitable polymerase. The blunt ended DNA molecules can be ligated with at least partially double stranded adapter (e.g., a Y shaped or bell-shaped adapter). Alternatively, complementary nucleotides can be added to blunt ends of sample nucleic acids and adapters to facilitate ligation. Contemplated herein are both blunt end ligation and sticky end ligation. In blunt end ligation, both the nucleic acid molecules and the adapter tags have blunt ends. In stickyend ligation, typically, the nucleic acid molecules bear an "A" overhang and the adapters bear a "T" overhang.

2. Amplification

Sample nucleic acids flanked by adapters can be amplified by PCR and other amplification methods. Amplification is typically primed by primers binding to primer binding sites in adapters flanking a DNA molecule to be amplified. Amplification methods can involve cycles of denaturation, annealing and extension, resulting from thermocycling or can be isothermal as in transcription-mediated amplification. Other amplification methods include the ligase chain reaction, strand displacement amplification, nucleic acid sequence based amplification, and self-sustained sequence based replication.

In some embodiments, the present methods perform dsDNA ligations with T-tailed and C-tailed adapters, which result in amplification of at least 50, 60, 70 or 80% of double stranded nucleic acids before linking to adapters. Preferably the present methods increase the amount or number of amplified molecules relative to control methods performed with T-tailed adapters alone by at least 10, 15 or 20%.

3. Bait Sets; Capture Moieties

As discussed above, nucleic acids in a sample can be subject to a capture step, in which molecules having target sequences are captured for subsequent analysis. Target capture can involve use of a bait set comprising oligonucleotide baits labeled with a capture moiety, such as biotin or the other examples noted below. The probes can have sequences selected to tile across a panel of regions, such as genes. In some embodiments, a bait set can have higher and lower capture yields for sets of target regions such as those of the sequence-variable target region set and the epigenetic target region set, respectively, as discussed elsewhere herein. Such bait sets are combined with a sample under conditions that allow hybridization of the target molecules with the baits. Then, captured molecules are isolated using the capture moiety. For example, a biotin capture moiety by bead-based streptavidin. Such methods are further described in, for example, U.S. Pat. No. 9,850,523, issuing Dec. 26, 2017, which is incorporated herein by reference.

Capture moieties include, without limitation, biotin, avidin, streptavidin, a nucleic acid comprising a particular nucleotide sequence, a hapten recognized by an antibody, and magnetically attractable particles. The extraction moiety can be a member of a binding pair, such as biotin/streptavidin or hapten/antibody. In some embodiments, a capture moiety that is attached to an analyte is captured by its binding pair which is attached to an isolatable moiety, such as a magnetically attractable particle or a large particle that can be sedimented through centrifugation. The capture moiety can be any type of molecule that allows affinity separation of nucleic acids bearing the capture moiety from nucleic acids lacking the capture moiety. Exemplary capture moieties are biotin which allows affinity separation by binding to streptavidin linked or linkable to a solid phase or an oligonucleotide, which allows affinity separation through binding to a complementary oligonucleotide linked or linkable to a solid phase.

D. Collections of Target-Specific Probes

In some embodiments, a collection of target-specific probes is used in methods described herein. In some embodiments, the collection of target-specific probes comprises target-binding probes specific for a sequence-variable target region set and target-binding probes specific for an epigenetic target region set. In some embodiments, the capture yield of the target-binding probes specific for the sequence-variable target region set is higher (e.g., at least 2-fold higher) than the capture yield of the target-binding probes specific for the epigenetic target region set. In some embodiments, the collection of target-specific probes is configured to have a capture yield specific for the sequence-variable target region set higher (e.g., at least 2-fold higher) than its capture yield specific for the epigenetic target region set.

In some embodiments, the capture yield of the target-binding probes specific for the sequence-variable target region set is at least 1.25-, 1.5-, 1.75-, 2-, 2.25-, 2.5-, 2.75-, 3-, 3.5-, 4-, 4.5-, 5-, 6-, 7-, 8-, 9-, 10-, 11-, 12-, 13-, 14-, or 15-fold higher than the capture yield of the target-binding probes specific for the epigenetic target region set. In some embodiments, the capture yield of the target-binding probes specific for the sequence-variable target region set is 1.25- to 1.5-, 1.5- to 1.75-, 1.75- to 2-, 2- to 2.25-, 2.25- to 2.5-, 2.5- to 2.75-, 2.75- to 3-, 3- to 3.5-, 3.5- to 4-, 4- to 4.5-, 4.5- to 5-, 5- to 5.5-, 5.5- to 6-, 6- to 7-, 7- to 8-, 8- to 9-, 9- to 10-, 10- to 11-, 11- to 12-, 13- to 14-, or 14- to 15-fold higher than the capture yield of the target-binding Probes specific for the epigenetic target region set.

In some embodiments, the collection of target-specific probes is configured to have a capture yield specific for the sequence-variable target region set at least 1.25-, 1.5-, 1.75-, 2-, 2.25-, 2.5-, 2.75-, 3-, 3.5-, 4-, 4.5-, 5-, 6-, 7-, 8-, 9-, 10-, 11-, 12-, 13-, 14-, or 15-fold higher than its capture yield for the epigenetic target region set. In some embodiments, the collection of target-specific probes is configured to have a capture yield specific for the sequence-variable target region set is 1.25- to 1.5-, 1.5- to 1.75-, 1.75- to 2-, 2- to 2.25-, 2.25- to 2.5-, 2.5- to 2.75-, 2.75- to 3-, 3- to 3.5-, 3.5- to 4-, 4- to 4.5-, 4.5- to 5-, 5- to 5.5-, 5.5- to 6-, 6- to 7-, 7- to 8-, 8- to 9-, 9- to 10-, 10- to 11-, 11- to 12-, 13- to 14-, or 14- to 15-fold higher than its capture yield specific for the epigenetic target region set.

The collection of probes can be configured to provide higher capture yields for the sequence-variable target region set in various ways, including concentration, different lengths and/or chemistries (e.g., that affect affinity), and combinations thereof. Affinity can be modulated by adjusting probe length and/or including nucleotide modifications as discussed below.

In some embodiments, the target-specific probes specific for the sequence-variable target region set are present at a higher concentration than the target-specific probes specific for the epigenetic target region set. In some embodiments, concentration of the target-binding probes specific for the sequence-variable target region set is at least 1.25-, 1.5-, 1.75-, 2-, 2.25-, 2.5-, 2.75-, 3-, 3.5-, 4-, 4.5-, 5-, 6-, 7-, 8-, 9-, 10-, 11-, 12-, 13-, 14-, or 15-fold higher than the concentration of the target-binding probes specific for the epigenetic target region set. In some embodiments, the concentration of the target-binding probes specific for the sequence-variable target region set is 1.25- to 1.5-, 1.5- to 1.75-, 1.75- to 2-, 2- to 2.25-, 2.25- to 2.5-, 2.5- to 2.75-, 2.75- to 3-, 3- to 3.5-, 3.5- to 4-, 4- to 4.5-, 4.5- to 5-, 5- to 5.5-, 5.5- to 6-, 6- to 7-, 7- to 8-, 8- to 9-, 9- to 10-, 10- to 11-, 11- to 12-, 13- to 14-, or 14- to 15-fold higher than the concentration of the target-binding probes specific for the epigenetic target region set. In such embodiments, concentration may refer to the average mass per volume concentration of individual probes in each set.

In some embodiments, the target-specific probes specific for the sequence-variable target region set have a higher affinity for their targets than the target-specific probes specific for the epigenetic target region set. Affinity can be modulated in any way known to those skilled in the art, including by using different probe chemistries. For example, certain nucleotide modifications, such as cytosine 5-methylation (in certain sequence contexts), modifications that provide a heteroatom at the 2' sugar position, and LNA nucleotides, can increase stability of double-stranded nucleic acids, indicating that oligonucleotides with such modifications have relatively higher affinity for their complementary sequences. See, e.g., Severin et al., Nucleic Acids Res. 39: 8740-8751 (2011); Freier et al., Nucleic Acids Res. 25: 4429-4443 (1997); U.S. Pat. No. 9,738,894. Also, longer sequence lengths will generally provide increased affinity. Other nucleotide modifications, such as the substitution of the nucleobase hypoxanthine for guanine, reduce affinity by reducing the amount of hydrogen bonding between the oligonucleotide and its complementary sequence. In some embodiments, the target-specific probes specific for the sequence-variable target region set have modifications that increase their affinity for their targets. In some embodiments, alternatively or additionally, the target-specific probes specific for the epigenetic target region set have modifications that decrease their affinity for their targets. In some embodiments, the target-specific probes specific for the sequence-variable target region set have longer average lengths and/or higher average melting temperatures than the target-specific probes specific for the epigenetic target region set. These embodiments may be combined with each other and/or with differences in concentration as discussed above to achieve a desired fold difference in capture yield, such as any fold difference or range thereof described above.

In some embodiments, the target-specific probes comprise a capture moiety. The capture moiety may be any of the capture moieties described herein, e.g., biotin. In some embodiments, the target-specific probes are linked to a solid support, e.g., covalently or non-covalently such as through the interaction of a binding pair of capture moieties. In some embodiments, the solid support is a bead, such as a magnetic bead.

In some embodiments, the target-specific probes specific for the sequence-variable target region set and/or the target-specific probes specific for the epigenetic target region set are a bait set as discussed above, e.g., probes comprising capture moieties and sequences selected to tile across a panel of regions, such as genes.

In some embodiments, the target-specific probes are provided in a single composition. The single composition may be a solution (liquid or frozen). Alternatively, it may be a lyophilizate.

Alternatively, the target-specific probes may be provided as a plurality of compositions, e.g., comprising a first composition comprising probes specific for the epigenetic target region set and a second composition comprising probes specific for the sequence-variable target region set. These probes may be mixed in appropriate proportions to provide a combined probe composition with any of the foregoing fold differences in concentration and/or capture yield. Alternatively, they may be used in separate capture procedures (e.g., with aliquots of a sample or sequentially with the same sample) to provide first and second compositions comprising captured epigenetic target regions and sequence-variable target regions, respectively.

1. Probes Specific for Epigenetic Target Regions

The probes for the epigenetic target region set may comprise probes specific for one or more types of target regions likely to differentiate DNA from neoplastic (e.g., tumor or cancer) cells from healthy cells, e.g., non-neoplastic circulating cells. Exemplary types of such regions are discussed in detail herein, e.g., in the sections above concerning captured sets. The probes for the epigenetic target region set may also comprise probes for one or more control regions, e.g., as described herein.

In some embodiments, the probes for the epigenetic target region set have a footprint of at least 100 kbp, e.g., at least 200 kbp, at least 300 kbp, or at least 400 kbp. In some embodiments, the epigenetic target region set has a footprint in the range of 100-20 Mbp, e.g., 100-200 kbp, 200-300 kbp, 300-400 kbp, 400-500 kbp, 500-600 kbp, 600-700 kbp, 700-800 kbp, 800-900 kbp, 900-1,000 kbp, 1-1.5 Mbp, 1.5-2 Mbp, 2-3 Mbp, 3-4 Mbp, 4-5 Mbp, 5-6 Mbp, 6-7 Mbp, 7-8 Mbp, 8-9 Mbp, 9-10 Mbp, or 10-20 Mbp. In some embodiments, the epigenetic target region set has a footprint of at least 20 Mbp.

a. Hypermethylation Variable Target Regions

In some embodiments, the probes for the epigenetic target region set comprise probes specific for one or more hypermethylation variable target regions. Hypermethylation variable target regions may also be referred to herein as hypermethylated DMRs (differentially methylated regions). The hypermethylation variable target regions may be any of those set forth above. For example, in some embodiments, the probes specific for hypermethylation variable target regions comprise probes specific for a plurality of loci listed in Table 1, e.g., at least 10%, 20%, 30%, 40%, 50%, 60%, 70%, 80%, 90%, or 100% of the loci listed in Table 1. In some embodiments, the probes specific for hypermethylation variable target regions comprise probes specific for a plurality of loci listed in Table 2, e.g., at least 10%, 20%, 30%, 40%, 50%, 60%, 70%, 80%, 90%, or 100% of the loci listed in Table 2. In some embodiments, the probes specific for hypermethylation variable target regions comprise probes specific for a plurality of loci listed in Table 1 or Table 2, e.g., at least 10%, 20%, 30%, 40%, 50%, 60%, 70%, 80%, 90%, or 100% of the loci listed in Table 1 or Table 2. In some embodiments, for each locus included as a target region, there may be one or more probes with a hybridization site that binds between the transcription start site and the stop codon (the last stop codon for genes that are alternatively spliced) of the gene. In some embodiments, the one or more probes bind within 300 bp of the listed position, e.g., within 200 or 100 bp. In some embodiments, a probe has a hybridization site overlapping the position listed above. In some embodiments, the probes specific for the hypermethylation target regions include probes specific for one, two, three, four, or five subsets of hypermethylation target regions that collectively show hypermethylation in one, two, three, four, or five of breast, colon, kidney, liver, and lung cancers.

b. Hypomethylation Variable Target Regions

In some embodiments, the probes for the epigenetic target region set comprise probes specific for one or more hypomethylation variable target regions. Hypomethylation variable target regions may also be referred to herein as hypomethylated DMRs (differentially methylated regions). The hypomethylation variable target regions may be any of those set forth above. For example, the probes specific for one or more hypomethylation variable target regions may include probes for regions such as repeated elements, e.g., LINE1 elements, Alu elements, centromeric tandem repeats, pericentromeric tandem repeats, and satellite DNA, and intergenic regions that are ordinarily methylated in healthy cells may show reduced methylation in tumor cells.

In some embodiments, probes specific for hypomethylation variable target regions include probes specific for repeated elements and/or intergenic regions. In some embodiments, probes specific for repeated elements include probes specific for one, two, three, four, or five of LINE1 elements, Alu elements, centromeric tandem repeats, pericentromeric tandem repeats, and/or satellite DNA.

Exemplary probes specific for genomic regions that show cancer-associated hypomethylation include probes specific for nucleotides 8403565-8953708 and/or 151104701-151106035 of human chromosome 1. In some embodiments, the probes specific for hypomethylation variable target regions include probes specific for regions overlapping or comprising nucleotides 8403565-8953708 and/or 151104701-151106035 of human chromosome 1.

c. CTCF Binding Regions

In some embodiments, the probes for the epigenetic target region set include probes specific for CTCF binding regions. In some embodiments, the probes specific for CTCF binding regions comprise probes specific for at least 10, 20, 50, 100, 200, or 500 CTCF binding regions, or 10-20, 20-50, 50-100, 100-200, 200-500, or 500-1000 CTCF binding regions, e.g., such as CTCF binding regions described above or in one or more of CTCFBSDB or the Cuddapah et al., Martin et al., or Rhee et al. articles cited above. In some embodiments, the probes for the epigenetic target region set comprise at least 100 bp, at least 200 bp at least 300 bp, at least 400 bp, at least 500 bp, at least 750 bp, or at least 1000 bp upstream and downstream regions of the CTCF binding sites.

d. Transcription Start Sites

In some embodiments, the probes for the epigenetic target region set include probes specific for transcriptional start sites. In some embodiments, the probes specific for transcriptional start sites comprise probes specific for at least 10, 20, 50, 100, 200, or 500 transcriptional start sites, or 10-20, 20-50, 50-100, 100-200, 200-500, or 500-1000 transcriptional start sites, e.g., such as transcriptional start sites listed in DBTSS. In some embodiments, the probes for the epigenetic target region set comprise probes for sequences at least 100 bp, at least 200 bp, at least 300 bp, at least 400 bp, at least 500 bp, at least 750 bp, or at least 1000 bp upstream and downstream of the transcriptional start sites.

e. Focal Amplifications

As noted above, although focal amplifications are somatic mutations, they can be detected by sequencing based on read frequency in a manner analogous to approaches for detecting certain epigenetic changes such as changes in methylation. As such, regions that may show focal amplifications in cancer can be included in the epigenetic target region set, as discussed above. In some embodiments, the probes specific for the epigenetic target region set include probes specific for focal amplifications. In some embodiments, the probes specific for focal amplifications include probes specific for one or more of AR, BRAF, CCND1, CCND2, CCNE1, CDK4, CDK6, EGFR, ERBB2, FGFR1, FGFR2, KIT, KRAS, MET, MYC, PDGFRA, PIK3CA, and RAF1. For example, in some embodiments, the probes specific for focal amplifications include probes specific for one or more of at least 2, 3, 4, 5, 6, 7, 8, 9, 10, 11, 12, 13, 14, 15, 16, 17, or 18 of the foregoing targets.

f. Control Regions

It can be useful to include control regions to facilitate data validation. In some embodiments, the probes specific for the epigenetic target region set include probes specific for control methylated regions that are expected to be methylated in essentially all samples. In some embodiments, the probes specific for the epigenetic target region set include probes specific for control hypomethylated regions that are expected to be hypomethylated in essentially all samples.

2. Probes Specific for Sequence-Variable Target Regions

The probes for the sequence-variable target region set may comprise probes specific for a plurality of regions known to undergo somatic mutations in cancer. The probes may be specific for any sequence-variable target region set described herein. Exemplary sequence-variable target region sets are discussed in detail herein, e.g., in the sections above concerning captured sets.

In some embodiments, the sequence-variable target region probe set has a footprint of at least 0.5 kb, e.g., at least 1 kb, at least 2 kb, at least 5 kb, at least 10 kb, at least 20 kb, at least 30 kb, or at least 40 kb. In some embodiments, the epigenetic target region probe set has a footprint in the range of 0.5-100 kb, e.g., 0.5-2 kb, 2-10 kb, 10-20 kb, 20-30 kb, 30-40 kb, 40-50 kb, 50-60 kb, 60-70 kb, 70-80 kb, 80-90 kb, and 90-100 kb. In some embodiments, the sequence-variable target region probe set has a footprint of at least 50 kbp, e.g., at least 100 kbp, at least 200 kbp, at least 300 kbp, or at least 400 kbp. In some embodiments, the sequence-variable target region probe set has a footprint in the range of 100-2000 kbp, e.g., 100-200 kbp, 200-300 kbp, 300-400 kbp, 400-500 kbp, 500-600 kbp, 600-700 kbp, 700-800 kbp, 800-900 kbp, 900-1,000 kbp, 1-1.5 Mbp or 1.5-2 Mbp. In some embodiments, the sequence-variable target region set has a footprint of at least 2 Mbp.

In some embodiments, probes specific for the sequence-variable target region set comprise probes specific for at least a portion of at least 5, at least 10, at least 15, at least 20, at least 25, at least 30, at least 35, at least 40, at least 45, at least 50, at least 55, at least 60, at least 65, or at 70 of the genes of Table 3. In some embodiments, probes specific for the sequence-variable target region set comprise probes specific for the at least 5, at least 10, at least 15, at least 20, at least 25, at least 30, at least 35, at least 40, at least 45, at least 50, at least 55, at least 60, at least 65, or 70 of the SNVs of Table 3. In some embodiments, probes specific for the sequence-variable target region set comprise probes specific for at least 1, at least 2, at least 3, at least 4, at least 5, or 6 of the fusions of Table 3. In some embodiments, probes specific for the sequence-variable target region set comprise probes specific for at least a portion of at least 1, at least 2, or 3 of the indels of Table 3. In some embodiments, probes specific for the sequence-variable target region set comprise probes specific for at least a portion of at least 5, at least 10, at least 15, at least 20, at least 25, at least 30, at least 35, at least 40, at least 45, at least 50, at least 55, at least 60, at least 65, at least 70, or 73 of the genes of Table 4. In some embodiments, probes specific for the sequence-variable target region set comprise probes specific for at least 5, at least 10, at least 15, at least 20, at least 25, at least 30, at least 35, at least 40, at least 45, at least 50, at least 55, at least 60, at least 65, at least 70, or 73 of the SNVs of Table 4. In some embodiments, probes specific for the sequence-variable target region set comprise probes specific for at least 1, at least 2, at least 3, at least 4, at least 5, or 6 of the fusions of Table 4. In some embodiments, probes specific for the sequence-variable target region set comprise probes specific for at least a portion of at least 1, at least 2, at least 3, at least 4, at least 5, at least 6, at least 7, at least 8, at least 9, at least 10, at least 11, at least 12, at least 13, at least 14, at least 15, at least 16, at least 17, or 18 of the indels of Table 4. In some embodiments, probes specific for the sequence-variable target region set comprise probes specific for at least a portion of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 of the genes of Table 5.

In some embodiments, the probes specific for the sequence-variable target region set comprise probes specific for target regions from at least 10, 20, 30, or 35 cancer-related genes, such as AKT1, ALK, BRAF, CCND1, CDK2A, CTNNB1, EGFR, ERBB2, ESR1, FGFR1, FGFR2, FGFR3, FOXL2, GATA3, GNA11, GNAQ, GNAS, HRAS, IDH1, IDH2, KIT, KRAS, MED12, MET, MYC, NFE2L2, NRAS, PDGFRA, PIK3CA, PPP2R1A, PTEN, RET, STK11, TP53, and U2AF1.

E. Compositions Comprising Captured DNA

Provided herein is a combination comprising first and second populations of DNA, wherein the second population comprises fragments of DNA wherein a first nucleobase has undergone a conversion procedure, e.g., any of the conversion procedures described herein. For example, the DNA may comprise bases that were converted from methylated cytosines to another nucleobase, such as thymine. In some embodiments, the first and second populations are differentially tagged. Provided herein is a combination comprising first and second populations of DNA, wherein the second population may comprise a form of a first nucleobase originally present in the DNA with altered base pairing specificity and a second nucleobase without altered base pairing specificity, wherein the form of the first nucleobase originally present in the DNA prior to alteration of base pairing specificity is a modified or unmodified nucleobase, the second nucleobase is a modified or unmodified nucleobase different from the first nucleobase, and the form of the first nucleobase originally present in the DNA prior to alteration of base pairing specificity and the second nucleobase have the same base pairing specificity. The first population may comprise or be derived from DNA with a cytosine modification (e.g., cytosine methylation) in a greater proportion than the second population. The first population may comprise a form of a first nucleobase originally present in the DNA with altered base pairing specificity and a second nucleobase without altered base pairing specificity, wherein the form of the first nucleobase originally present in the DNA prior to alteration of base pairing specificity is a modified or unmodified nucleobase, the second nucleobase is a modified or unmodified nucleobase different from the first nucleobase, and the form of the first nucleobase originally present in the DNA prior to alteration of base pairing specificity and the second nucleobase have the same base pairing specificity. In some embodiments, the cytosine modification is cytosine methylation. In some embodiments, the first nucleobase is a modified or unmodified cytosine and the second nucleobase is a modified or unmodified cytosine. The first and second nucleobase may be any of those discussed herein in the Summary or with respect to subjecting the first subsample to a procedure that affects a first nucleobase in the DNA differently from a second nucleobase in the DNA of the first subsample. In some embodiments, the first population comprises fragments of DNA with ends, or attached tags or adapters, at a recognition site of at least one methylation-sensitive nuclease, which may be any one or any combination of the methylation-sensitive nucleases described herein.

In some embodiments, the first population comprises a sequence tag selected from a first set of one or more sequence tags and the second population comprises a sequence tag selected from a second set of one or more sequence tags, and the second set of sequence tags is different from the first set of sequence tags. The sequence tags may comprise barcodes.

In some embodiments, the first population comprises protected hmC, such as glucosylated hmC.

In some embodiments, the first population was subjected to any of the conversion procedures discussed herein, such as bisulfite conversion, Ox-BS conversion, TAB conversion, ACE conversion, TAP conversion, TAPSβ conversion, or CAP conversion. In some embodiments, the first population was subjected to protection of hmC followed by deamination of mC and/or C.

In some embodiments of the combination, the first population comprises or was derived from DNA with a cytosine modification in a greater proportion than the second population and the first population comprises first and second subpopulations, and the first nucleobase is a modified or unmodified nucleobase, the second nucleobase is a modified or unmodified nucleobase different from the first nucleobase, and the first nucleobase and the second nucleobase have the same base pairing specificity. In some embodiments, the second population does not comprise the first nucleobase. In some embodiments, the first nucleobase is a modified or unmodified cytosine, and the second nucleobase is a modified or unmodified cytosine, optionally wherein the modified cytosine is mC or hmC. In some embodiments, the first nucleobase is a modified or unmodified adenine, and the second nucleobase is a modified or unmodified adenine, optionally wherein the modified adenine is mA.

In some embodiments, the first nucleobase (e.g., a modified cytosine) is biotinylated. In some embodiments, the first nucleobase (e.g., a modified cytosine) is a product of a Huisgen cycloaddition to β-6-azide-glucosyl-5-hydroxymethylcytosine that comprises an affinity label (e.g., biotin).

In any of the combinations described herein, the captured DNA may comprise cfDNA.

The captured DNA may have any of the features described herein concerning captured sets, including, e.g., a greater concentration of the DNA corresponding to the sequence-variable target region set (normalized for footprint size as discussed above) than of the DNA corresponding to the epigenetic target region set. In some embodiments, the DNA of the captured set comprises sequence tags, which may be added to the DNA as described herein. In general, the inclusion of sequence tags results in the DNA molecules differing from their naturally occurring, untagged form.

The combination may further comprise a probe set described herein or sequencing primers, each of which may differ from naturally occurring nucleic acid molecules. For example, a probe set described herein may comprise a capture moiety, and sequencing primers may comprise a non-naturally occurring label.

F. Computer Systems

Methods of the present disclosure can be implemented using, or with the aid of, computer systems. For example, such methods may comprise: partitioning the sample into a plurality of subsamples, including a first subsample and a second subsample, wherein the first subsample comprises DNA with a cytosine modification in a greater proportion than the second subsample; subjecting the second subsample to a procedure that affects a first nucleobase in the DNA differently from a second nucleobase in the DNA of the second subsample, wherein the first nucleobase is a modified or unmodified nucleobase, the second nucleobase is a modified or unmodified nucleobase different from the first nucleobase, and the first nucleobase and the second nucleobase have the same base pairing specificity, thereby producing a treated subsample; capturing a target region set comprising epigenetic target regions from the treated subsample; and sequencing DNA in the target region set and DNA from the first subsample, wherein DNA from the second subsample is sequenced in a manner that distinguishes the first nucleobase from the second nucleobase in the DNA of the target region set.

Figure 4:
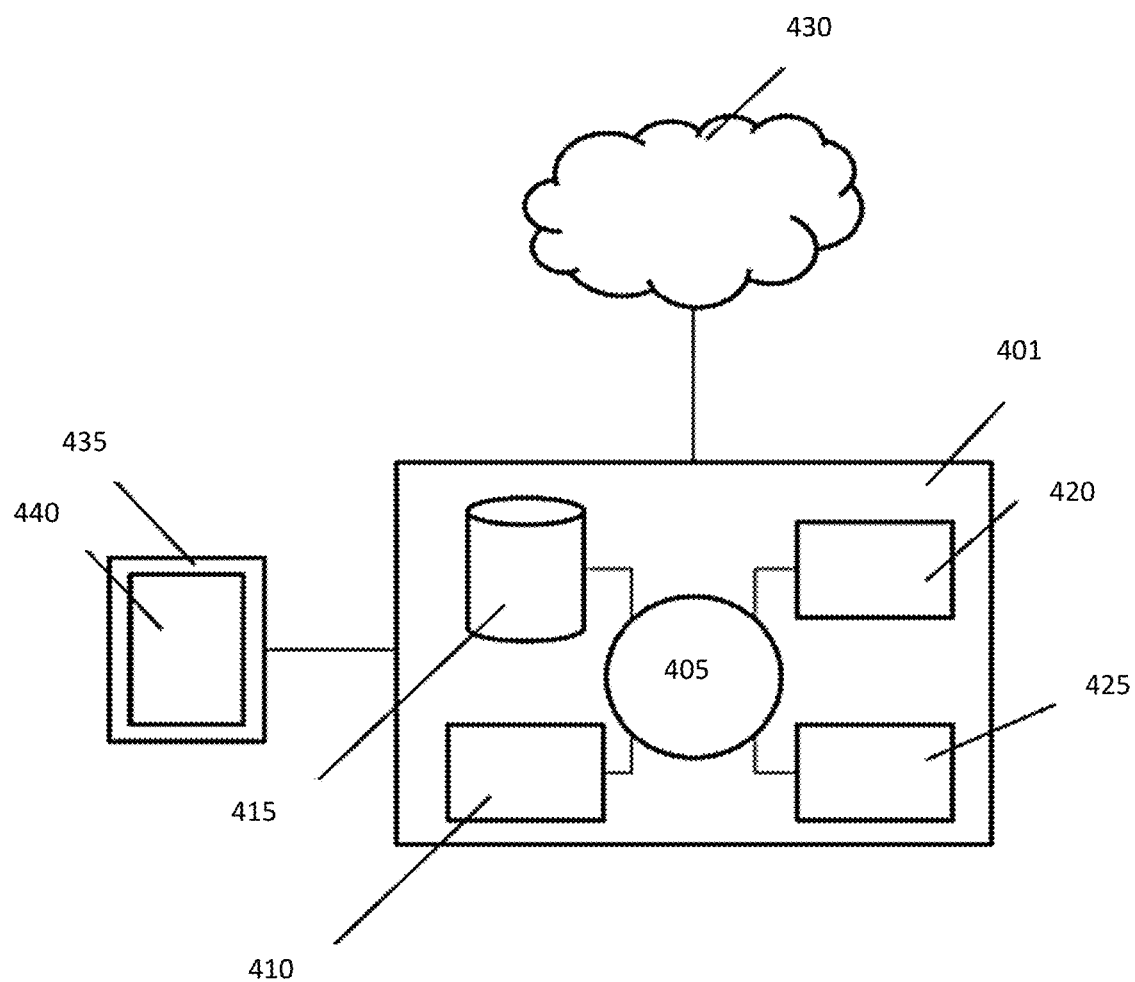
FIG. 4 is a schematic diagram of an example of a system suitable for use with some embodiments of the disclosure.

FIG. 4 shows a computer system 401 that is programmed or otherwise configured to implement the methods of the present disclosure. The computer system 401 can regulate various aspects sample preparation, sequencing, and/or analysis. In some examples, the computer system 401 is configured to perform sample preparation and sample analysis, including nucleic acid sequencing.

The computer system 401 includes a central processing unit (CPU, also "processor" and "computer processor" herein) 405, which can be a single core or multi core processor, or a plurality of processors for parallel processing. The computer system 401 also includes memory or memory location 410 (e.g., random-access memory, read-only memory, flash memory), electronic storage unit 415 (e.g., hard disk), communication interface 420 (e.g., network adapter) for communicating with one or more other systems, and peripheral devices 425, such as cache, other memory, data storage, and/or electronic display adapters. The memory 410, storage unit 415, interface 420, and peripheral devices 425 are in communication with the CPU 405 through a communication network or bus (solid lines), such as a motherboard. The storage unit 415 can be a data storage unit (or data repository) for storing data. The computer system 401 can be operatively coupled to a computer network 430 with the aid of the communication interface 420. The computer network 430 can be the Internet, an internet and/or extranet, or an intranet and/or extranet that is in communication with the Internet. The computer network 430 in some cases is a telecommunication and/or data network. The computer network 430 can include one or more computer servers, which can enable distributed computing, such as cloud computing. The computer network 430, in some cases with the aid of the computer system 401, can implement a peer-to-peer network, which may enable devices coupled to the computer system 401 to behave as a client or a server.

The CPU 405 can execute a sequence of machine-readable instructions, which can be embodied in a program or software. The instructions may be stored in a memory location, such as the memory 410. Examples of operations performed by the CPU 405 can include fetch, decode, execute, and writeback.

The storage unit 415 can store files, such as drivers, libraries, and saved programs. The storage unit 415 can store programs generated by users and recorded sessions, as well as output(s) associated with the programs. The storage unit 415 can store user data, e.g., user preferences and user programs. The computer system 401 in some cases can include one or more additional data storage units that are external to the computer system 401, such as located on a remote server that is in communication with the computer system 401 through an intranet or the Internet. Data may be transferred from one location to another using, for example, a communication network or physical data transfer (e.g., using a hard drive, thumb drive, or other data storage mechanism).

The computer system 401 can communicate with one or more remote computer systems through the network 430. For embodiment, the computer system 401 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 401 via the network 430.

Methods as described herein can be implemented by way of machine (e.g., computer processor) executable code stored on an electronic storage location of the computer system 401, such as, for example, on the memory 410 or electronic storage unit 415. The machine executable or machine-readable code can be provided in the form of software. During use, the code can be executed by the processor 405. In some cases, the code can be retrieved from the storage unit 415 and stored on the memory 410 for ready access by the processor 405. In some situations, the electronic storage unit 415 can be precluded, and machine-executable instructions are stored on memory 410.

In an aspect, the present disclosure provides a non-transitory computer-readable medium comprising computer-executable instructions which, when executed by at least one electronic processor, perform at least a portion of a method comprising: a) partitioning the sample into a plurality of subsamples, including a first subsample and a second subsample, wherein the first subsample comprises DNA with a cytosine modification in a greater proportion than the second subsample; b) subjecting the second subsample to a procedure that affects a first nucleobase in the DNA differently from a second nucleobase in the DNA of the second subsample, wherein the first nucleobase is a modified or unmodified nucleobase, the second nucleobase is a modified or unmodified nucleobase different from the first nucleobase, and the first nucleobase and the second nucleobase have the same base pairing specificity, thereby producing a treated subsample; c) capturing a target region set comprising epigenetic target regions from the treated subsample; and d) sequencing DNA in the target region set and DNA from the first subsample, wherein DNA from the second subsample is sequenced in a manner that distinguishes the first nucleobase from the second nucleobase in the DNA of the target region set. In an aspect, the present disclosure provides a non-transitory computer-readable medium comprising computer-executable instructions which, when executed by at least one electronic processor, perform at least a portion of a method comprising: a) capturing a target region set comprising epigenetic target regions from the sample; b) partitioning the target region set into a plurality of subsamples, including a first subsample and a second subsample, wherein the first subsample comprises DNA with a cytosine modification in a greater proportion than the second subsample; c) subjecting the second subsample to a procedure that affects a first nucleobase in the DNA differently from a second nucleobase in the DNA of the second subsample, wherein the first nucleobase is a modified or unmodified nucleobase, the second nucleobase is a modified or unmodified nucleobase different from the first nucleobase, and the first nucleobase and the second nucleobase have the same base pairing specificity, thereby producing a treated subsample; and d) sequencing DNA from the first subsample and DNA from the second subsample, wherein DNA from the second subsample is sequenced in a manner that distinguishes the first nucleobase from the second nucleobase in the DNA of the target region set. In an aspect, the present disclosure provides a non-transitory computer-readable medium comprising computer-executable instructions which, when executed by at least one electronic processor, perform at least a portion of a method comprising: a) partitioning the sample into a plurality of subsamples, including a first subsample and a second subsample, wherein the first subsample comprises DNA with a cytosine modification in a greater proportion than the second subsample; b) subjecting the second subsample to a procedure that affects a first nucleobase in the DNA differently from a second nucleobase in the DNA of the second subsample, wherein the first nucleobase is a modified or unmodified nucleobase, the second nucleobase is a modified or unmodified nucleobase different from the first nucleobase, and the first nucleobase and the second nucleobase have the same base pairing specificity, thereby producing a treated subsample; and c) sequencing DNA from the treated subsample and DNA from the first subsample in a manner that distinguishes the first nucleobase from the second nucleobase in the DNA of the target region set. In some embodiments, the method further comprises obtaining a plurality of sequence reads generated by a nucleic acid sequencer from the sequencing; mapping the plurality of sequence reads to one or more reference sequences to generate mapped sequence reads; and processing the mapped sequence reads to determine the likelihood that the subject has cancer.

The code can be pre-compiled and configured for use with a machine have a processor adapted to execute the code or can be compiled during runtime. The code can be supplied in a programming language that can be selected to enable the code to execute in a pre-compiled or as-compiled fashion.

Aspects of the systems and methods provided herein, such as the computer system 401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming.

All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as those used across physical interfaces between local devices, through wired and optical landline networks, and over various air-links. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

Hence, a machine-readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards, paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 401 can include or be in communication with an electronic display 435 that comprises a user interface (UI) 440 for providing, for example, one or more results of sample analysis. Examples of UIs include, without limitation, a graphical user interface (GUI) and web-based user interface.

Additional details relating to computer systems and networks, databases, and computer program products are also provided in, for example, Peterson, *Computer Networks: A Systems Approach*, Morgan Kaufmann, 5th Ed. (2011), Kurose, *Computer Networking: A Top-Down Approach*, Pearson, 7th Ed. (2016), Elmasri, *Fundamentals of Database Systems*, Addison Wesley, 6th Ed. (2010), Coronel, *Database Systems: Design, Implementation, & Management*, Cengage Learning, 11th Ed. (2014), Tucker, *Programming Languages*, McGraw-Hill Science/Engineering/Math, 2nd Ed. (2006), and Rhoton, *Cloud Computing Architected: Solution Design Handbook*, Recursive Press (2011), each of which is hereby incorporated by reference in its entirety.

G. Applications

1. Cancer and Other Diseases

The present methods can be used to diagnose presence of conditions, particularly cancer, in a subject, to characterize conditions (e.g., staging cancer or determining heterogeneity of a cancer), monitor response to treatment of a condition, effect prognosis risk of developing a condition or subsequent course of a condition. The present disclosure can also be useful in determining the efficacy of a particular treatment option. Successful treatment options may increase the amount of copy number variation or rare mutations detected in subject's blood if the treatment is successful as more cancers may die and shed DNA. In other examples, this may not occur. In another example, perhaps certain treatment options may be correlated with genetic profiles of cancers over time. This correlation may be useful in selecting a therapy. In some embodiments, hypermethylation variable epigenetic target regions are analyzed to determine whether they show hypermethylation characteristic of tumor cells or cells that do not ordinarily contribute significantly to cfDNA and/or hypomethylation variable epigenetic target regions are analyzed to determine whether they show hypomethylation characteristic of tumor cells or cells that do not ordinarily contribute significantly to cfDNA.

Additionally, if a cancer is observed to be in remission after treatment, the present methods can be used to monitor residual disease or recurrence of disease.

In some embodiments, the methods and systems disclosed herein may be used to identify customized or targeted therapies to treat a given disease or condition in patients based on the classification of a nucleic acid variant as being of somatic or germline origin. Typically, the disease under consideration is a type of cancer. Non-limiting examples of such cancers include biliary tract cancer, bladder cancer, transitional cell carcinoma, urothelial carcinoma, brain cancer, gliomas, astrocytomas, breast carcinoma, metaplastic carcinoma, cervical cancer, cervical squamous cell carcinoma, rectal cancer, colorectal carcinoma, colon cancer, hereditary nonpolyposis colorectal cancer, colorectal adenocarcinomas, gastrointestinal stromal tumors (GISTs), endometrial carcinoma, endometrial stromal sarcomas, esophageal cancer, esophageal squamous cell carcinoma, esophageal adenocarcinoma, ocular melanoma, uveal melanoma, gallbladder carcinomas, gallbladder adenocarcinoma, renal cell carcinoma, clear cell renal cell carcinoma, transitional cell carcinoma, urothelial carcinomas, Wilms tumor, leukemia, acute lymphocytic leukemia (ALL), acute myeloid leukemia (AML), chronic lymphocytic leukemia (CLL), chronic myeloid leukemia (CML), chronic myelomonocytic leukemia (CMML), liver cancer, liver carcinoma, hepatoma, hepatocellular carcinoma, cholangiocarcinoma, hepatoblastoma, Lung cancer, non-small cell lung cancer (NSCLC), mesothelioma, B-cell lymphomas, non-Hodgkin lymphoma, diffuse large B-cell lymphoma, Mantle cell lymphoma, T cell lymphomas, non-Hodgkin lymphoma, precursor T-lymphoblastic lymphoma/leukemia, peripheral T cell lymphomas, multiple myeloma, nasopharyngeal carcinoma (NPC), neuroblastoma, oropharyngeal cancer, oral cavity squamous cell carcinomas, osteosarcoma, ovarian carcinoma, pancreatic cancer, pancreatic ductal adenocarcinoma, pseudopapillary neoplasms, acinar cell carcinomas. Prostate cancer, prostate adenocarcinoma, skin cancer, melanoma, malignant melanoma, cutaneous melanoma, small intestine carcinomas, stomach cancer, gastric carcinoma, gastrointestinal stromal tumor (GIST), uterine cancer, or uterine sarcoma. Type and/or stage of cancer can be detected from genetic variations including mutations, rare mutations, indels, copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns, and abnormal changes in nucleic acid 5-methylcytosine.

Genetic data can also be used for characterizing a specific form of cancer. Cancers are often heterogeneous in both composition and staging. Genetic profile data may allow characterization of specific sub-types of cancer that may be important in the diagnosis or treatment of that specific sub-type. This information may also provide a subject or practitioner clues regarding the prognosis of a specific type of cancer and allow either a subject or practitioner to adapt treatment options in accord with the progress of the disease. Some cancers can progress to become more aggressive and genetically unstable. Other cancers may remain benign, inactive or dormant. The system and methods of this disclosure may be useful in determining disease progression.

Further, the methods of the disclosure may be used to characterize the heterogeneity of an abnormal condition in a subject. Such methods can include, e.g., generating a genetic profile of extracellular polynucleotides derived from the subject, wherein the genetic profile comprises a plurality of data resulting from copy number variation and rare mutation analyses. In some embodiments, an abnormal condition is cancer. In some embodiments, the abnormal condition may be one resulting in a heterogeneous genomic population. In the example of cancer, some tumors are known to comprise tumor cells in different stages of the cancer. In other examples, heterogeneity may comprise multiple foci of disease. Again, in the example of cancer, there may be multiple tumor foci, perhaps where one or more foci are the result of metastases that have spread from a primary site.

The present methods can be used to generate or profile, fingerprint or set of data that is a summation of genetic information derived from different cells in a heterogeneous disease. This set of data may comprise copy number variation, epigenetic variation, and mutation analyses alone or in combination.

The present methods can be used to diagnose, prognose, monitor or observe cancers, or other diseases. In some embodiments, the methods herein do not involve the diagnosing, prognosing or monitoring a fetus and as such are not directed to non-invasive prenatal testing. In other embodiments, these methodologies may be employed in a pregnant subject to diagnose, prognose, monitor or observe cancers or other diseases in an unborn subject whose DNA and other polynucleotides may co-circulate with maternal molecules.

Non-limiting examples of other genetic-based diseases, disorders, or conditions that are optionally evaluated using the methods and systems disclosed herein include achondroplasia, alpha-1 antitrypsin deficiency, antiphospholipid syndrome, autism, autosomal dominant polycystic kidney disease, Charcot-Marie-Tooth (CMT), cri du chat, Crohn's disease, cystic fibrosis, Dercum disease, down syndrome, Duane syndrome, Duchenne muscular dystrophy, Factor V Leiden thrombophilia, familial hypercholesterolemia, familial Mediterranean fever, fragile X syndrome, Gaucher disease, hemochromatosis, hemophilia, holoprosencephaly, Huntington's disease, Klinefelter syndrome, Marfan syndrome, myotonic dystrophy, neurofibromatosis, Noonan syndrome, osteogenesis imperfecta, Parkinson's disease, phenylketonuria, Poland anomaly, porphyria, progeria, retinitis pigmentosa, severe combined immunodeficiency (SCID), sickle cell disease, spinal muscular atrophy, Tay-Sachs, thalassemia, trimethylaminuria, Turner syndrome, velocardiofacial syndrome, WAGR syndrome, Wilson disease, or the like.

In some embodiments, a method described herein comprises detecting a presence or absence of DNA originating or derived from a tumor cell at a preselected timepoint following a previous cancer treatment of a subject previously diagnosed with cancer using a set of sequence information obtained as described herein. The method may further comprise determining a cancer recurrence score that is indicative of the presence or absence of the DNA originating or derived from the tumor cell for the test subject.

Where a cancer recurrence score is determined, it may further be used to determine a cancer recurrence status. The cancer recurrence status may be at risk for cancer recurrence, e.g., when the cancer recurrence score is above a predetermined threshold. The cancer recurrence status may be at low or lower risk for cancer recurrence, e.g., when the cancer recurrence score is above a predetermined threshold. In particular embodiments, a cancer recurrence score equal to the predetermined threshold may result in a cancer recurrence status of either at risk for cancer recurrence or at low or lower risk for cancer recurrence.

In some embodiments, a cancer recurrence score is compared with a predetermined cancer recurrence threshold, and the test subject is classified as a candidate for a subsequent cancer treatment when the cancer recurrence score is above the cancer recurrence threshold or not a candidate for therapy when the cancer recurrence score is below the cancer recurrence threshold. In particular embodiments, a cancer recurrence score equal to the cancer recurrence threshold may result in classification as either a candidate for a subsequent cancer treatment or not a candidate for therapy.

The methods discussed above may further comprise any compatible feature or features set forth elsewhere herein, including in the section regarding methods of determining a risk of cancer recurrence in a test subject and/or classifying a test subject as being a candidate for a subsequent cancer treatment.

2. Methods of Determining a Risk of Cancer Recurrence in a Test Subject and/or Classifying a Test Subject as being a Candidate for a Subsequent Cancer Treatment In some embodiments, a method provided herein is a method of determining a risk of cancer recurrence in a test subject. In some embodiments, a method provided herein is a method of classifying a test subject as being a candidate for a subsequent cancer treatment.

Any of such methods may comprise collecting DNA (e.g., originating or derived from a tumor cell) from the test subject diagnosed with the cancer at one or more preselected timepoints following one or more previous cancer treatments to the test subject. The subject may be any of the subjects described herein. The DNA may be cfDNA. The DNA may be obtained from a tissue sample.

Any of such methods may comprise capturing a plurality of sets of target regions from DNA from the subject, wherein the plurality of target region sets comprises a sequence-variable target region set and an epigenetic target region set, whereby a captured set of DNA molecules is produced. The capturing step may be performed according to any of the embodiments described elsewhere herein.

In any of such methods, the previous cancer treatment may comprise surgery, administration of a therapeutic composition, and/or chemotherapy.

Any of such methods may comprise sequencing the captured DNA molecules, whereby a set of sequence information is produced. The captured DNA molecules of the sequence-variable target region set may be sequenced to a greater depth of sequencing than the captured DNA molecules of the epigenetic target region set.

Any of such methods may comprise detecting a presence or absence of DNA originating or derived from a tumor cell at a preselected timepoint using the set of sequence information. The detection of the presence or absence of DNA originating or derived from a tumor cell may be performed according to any of the embodiments thereof described elsewhere herein.

Methods of determining a risk of cancer recurrence in a test subject may comprise determining a cancer recurrence score that is indicative of the presence or absence, or amount, of the DNA originating or derived from the tumor cell for the test subject. The cancer recurrence score may further be used to determine a cancer recurrence status. The cancer recurrence status may be at risk for cancer recurrence, e.g., when the cancer recurrence score is above a predetermined threshold. The cancer recurrence status may be at low or lower risk for cancer recurrence, e.g., when the cancer recurrence score is above a predetermined threshold. In particular embodiments, a cancer recurrence score equal to the predetermined threshold may result in a cancer recurrence status of either at risk for cancer recurrence or at low or lower risk for cancer recurrence.

Methods of classifying a test subject as being a candidate for a subsequent cancer treatment may comprise comparing the cancer recurrence score of the test subject with a predetermined cancer recurrence threshold, thereby classifying the test subject as a candidate for the subsequent cancer treatment when the cancer recurrence score is above the cancer recurrence threshold or not a candidate for therapy when the cancer recurrence score is below the cancer recurrence threshold. In particular embodiments, a cancer recurrence score equal to the cancer recurrence threshold may result in classification as either a candidate for a subsequent cancer treatment or not a candidate for therapy. In some embodiments, the subsequent cancer treatment comprises chemotherapy or administration of a therapeutic composition.

Any of such methods may comprise determining a disease-free survival (DFS) period for the test subject based on the cancer recurrence score; for example, the DFS period may be 1 year, 2 years, 3, years, 4 years, 5 years, or 10 years.

In some embodiments, the set of sequence information comprises sequence-variable target region sequences, and determining the cancer recurrence score may comprise determining at least a first subscore indicative of the amount of SNVs, insertions/deletions, CNVs and/or fusions present in sequence-variable target region sequences.

In some embodiments, a number of mutations in the sequence-variable target regions chosen from 1, 2, 3, 4, or 5 is sufficient for the first subscore to result in a cancer recurrence score classified as positive for cancer recurrence. In some embodiments, the number of mutations is chosen from 1, 2, or 3.

In some embodiments, the set of sequence information comprises epigenetic target region sequences, and determining the cancer recurrence score comprises determining a second subscore indicative of the amount of molecules (obtained from the epigenetic target region sequences) that represent an epigenetic state different from DNA found in a corresponding sample from a healthy subject (e.g., cfDNA found in a blood sample from a healthy subject, or DNA found in a tissue sample from a healthy subject where the tissue sample is of the same type of tissue as was obtained from the test subject). These abnormal molecules (i.e., molecules with an epigenetic state different from DNA found in a corresponding sample from a healthy subject) may be consistent with epigenetic changes associated with cancer, e.g., methylation of hypermethylation variable target regions and/or perturbed fragmentation of fragmentation variable target regions, where "perturbed" means different from DNA found in a corresponding sample from a healthy subject.

In some embodiments, a proportion of molecules corresponding to the hypermethylation variable target region set and/or fragmentation variable target region set that indicate hypermethylation in the hypermethylation variable target region set and/or abnormal fragmentation in the fragmentation variable target region set greater than or equal to a value in the range of 0.001%-10% is sufficient for the second subscore to be classified as positive for cancer recurrence. The range may be 0.001%-1%, 0.005%-1%, 0.01%-5%, 0.01%-2%, or 0.01%-1%.

In some embodiments, any of such methods may comprise determining a fraction of tumor DNA from the fraction of molecules in the set of sequence information that indicate one or more features indicative of origination from a tumor cell. This may be done for molecules corresponding to some or all of the epigenetic target regions, e.g., including one or both of hypermethylation variable target regions and fragmentation variable target regions (hypermethylation of a hypermethylation variable target region and/or abnormal fragmentation of a fragmentation variable target region may be considered indicative of origination from a tumor cell). This may be done for molecules corresponding to sequence variable target regions, e.g., molecules comprising alterations consistent with cancer, such as SNVs, indels, CNVs, and/or fusions. The fraction of tumor DNA may be determined based on a combination of molecules corresponding to epigenetic target regions and molecules corresponding to sequence variable target regions.

Determination of a cancer recurrence score may be based at least in part on the fraction of tumor DNA, wherein a fraction of tumor DNA greater than a threshold in the range of $10^{-11}$ to 1 or $10^{-19}$ to 1 is sufficient for the cancer recurrence score to be classified as positive for cancer recurrence. In some embodiments, a fraction of tumor DNA greater than or equal to a threshold in the range of $10^{-10}$ to $10^{-9}$, $10^{-9}$ to $10^{-8}$, $10^{-8}$ to $10^{-7}$, $10^{-7}$ to $10^{-6}$, $10^{-6}$ to $10^{-5}$, $10^{-5}$ to $10^{-4}$, $10^{-4}$ to $10^{-3}$, $10^{-3}$ to $10^{-2}$, or $10^{-2}$ to $10^{-1}$ is sufficient for the cancer recurrence score to be classified as positive for cancer recurrence. In some embodiments, the fraction of tumor DNA greater than a threshold of at least $10^{-7}$ is sufficient for the cancer recurrence score to be classified as positive for cancer recurrence. A determination that a fraction of tumor DNA is greater than a threshold, such as a threshold corresponding to any of the foregoing embodiments, may be made based on a cumulative probability. For example, the sample was considered positive if the cumulative probability that the tumor fraction was greater than a threshold in any of the foregoing ranges exceeds a probability threshold of at least 0.5, 0.75, 0.9, 0.95, 0.98, 0.99, 0.995, or 0.999. In some embodiments, the probability threshold is at least 0.95, such as 0.99.

In some embodiments, the set of sequence information comprises sequence-variable target region sequences and epigenetic target region sequences, and determining the cancer recurrence score comprises determining a first subscore indicative of the amount of SNVs, insertions/deletions, CNVs and/or fusions present in sequence-variable target region sequences and a second subscore indicative of the amount of abnormal molecules in epigenetic target region sequences, and combining the first and second subscores to provide the cancer recurrence score. Where the first and second subscores are combined, they may be combined by applying a threshold to each subscore independently (e.g., greater than a predetermined number of mutations (e.g., >1) in sequence-variable target regions, and greater than a predetermined fraction of abnormal molecules (i.e., molecules with an epigenetic state different from the DNA found in a corresponding sample from a healthy subject; e.g., tumor) in epigenetic target regions), or training a machine learning classifier to determine status based on a plurality of positive and negative training samples.

In some embodiments, a value for the combined score in the range of −4 to 2 or −3 to 1 is sufficient for the cancer recurrence score to be classified as positive for cancer recurrence.

In any embodiment where a cancer recurrence score is classified as positive for cancer recurrence, the cancer recurrence status of the subject may be at risk for cancer recurrence and/or the subject may be classified as a candidate for a subsequent cancer treatment.

In some embodiments, the cancer is any one of the types of cancer described elsewhere herein, e.g., colorectal cancer.

3. Therapies and Related Administration

In certain embodiments, the methods disclosed herein relate to identifying and administering customized therapies to patients given the status of a nucleic acid variant as being of somatic or germline origin. In some embodiments, essentially any cancer therapy (e.g., surgical therapy, radiation therapy, chemotherapy, and/or the like) may be included as part of these methods. Typically, customized therapies include at least one immunotherapy (or an immunotherapeutic agent). Immunotherapy refers generally to methods of enhancing an immune response against a given cancer type. In certain embodiments, immunotherapy refers to methods of enhancing a T cell response against a tumor or cancer.

In certain embodiments, the status of a nucleic acid variant from a sample from a subject as being of somatic or germline origin may be compared with a database of comparator results from a reference population to identify customized or targeted therapies for that subject. Typically, the reference population includes patients with the same cancer or disease type as the test subject and/or patients who are receiving, or who have received, the same therapy as the test subject. A customized or targeted therapy (or therapies) may be identified when the nucleic variant and the comparator results satisfy certain classification criteria (e.g., are a substantial or an approximate match).

In certain embodiments, the customized therapies described herein are typically administered parenterally (e.g., intravenously or subcutaneously). Pharmaceutical compositions containing an immunotherapeutic agent are typically administered intravenously. Certain therapeutic agents are administered orally. However, customized therapies (e.g., immunotherapeutic agents, etc.) may also be administered by methods such as, for example, buccal, sublingual, rectal, vaginal, intraurethral, topical, intraocular, intranasal, and/or intraauricular, which administration may include tablets, capsules, granules, aqueous suspensions, gels, sprays, suppositories, salves, ointments, or the like.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the disclosure described herein may be employed in practicing the invention. It is therefore contemplated that the disclosure shall also cover any such alternatives, modifications, variations or equivalents. It is intended that the following claims define the scope of the invention and that methods and structures within the scope of these claims and their equivalents be covered thereby.

While the foregoing disclosure has been described in some detail by way of illustration and example for purposes of clarity and understanding, it will be clear to one of ordinary skill in the art from a reading of this disclosure that various changes in form and detail can be made without departing from the true scope of the disclosure and may be practiced within the scope of the appended claims. For example, all the methods, systems, computer readable media, and/or component features, steps, elements, or other aspects thereof can be used in various combinations.

H. Kits

Also provided are kits comprising the compositions as described herein. The kits can be useful in performing the methods as described herein. In some embodiments, a kit comprises a first reagent for partitioning a sample into a plurality of subsamples as described herein, such as any of the partitioning reagents described elsewhere herein. In some embodiments, a kit comprises a second reagent for subjecting the first subsample to a procedure that affects a first nucleobase in the DNA differently from a second nucleobase in the DNA of the first subsample, wherein the first nucleobase is a modified or unmodified nucleobase, the second nucleobase is a modified or unmodified nucleobase different from the first nucleobase, and the first nucleobase and the second nucleobase have the same base pairing specificity (e.g., any of the reagents described elsewhere herein for converting a nucleobase such as cytosine or methylated cytosine to a different nucleobase). The kit may comprise the first and second reagents and additional elements as discussed below and/or elsewhere herein.

Kits may further comprise a plurality of oligonucleotide probes that selectively hybridize to least 5, 6, 7, 8, 9, 10, 20, 30, 40 or all genes selected from the group consisting of ALK, APC, BRAF, CDKN2A, EGFR, ERBB2, FBXW7, KRAS, MYC, NOTCH1, NRAS, PIK3CA, PTEN, RBI, TP53, MET, AR, ABL1, AKT1, ATM, CDH1, CSFIR, CTNNB1, ERBB4, EZH2, FGFR1, FGFR2, FGFR3, FLT3, GNA11, GNAQ, GNAS, HNF1A, HRAS, IDH1, IDH2, JAK2, JAK3, KDR, KIT, MLH1, MPL, NPM1, PDGFRA, PROC, PTPN11, RET, SMAD4, SMARCB1, SMO, SRC, STK11, VHL, TERT, CCND1, CDK4, CDKN2B, RAF1, BRCA1, CCND2, CDK6, NF1, TP53, ARID 1 A, BRCA2, CCNE1, ESR1, RIT1, GATA3, MAP2K1, RHEB, ROS1, ARAF, MAP2K2, NFE2L2, RHOA, and NTRK1. The number genes to which the oligonucleotide probes can selectively hybridize can vary. For example, the number of genes can comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, or 54. The kit can include a container that includes the plurality of oligonucleotide probes and instructions for performing any of the methods described herein.

The oligonucleotide probes can selectively hybridize to exon regions of the genes, e.g., of the at least 5 genes. In some cases, the oligonucleotide probes can selectively hybridize to at least 30 exons of the genes, e.g., of the at least 5 genes. In some cases, the multiple probes can selectively hybridize to each of the at least 30 exons. The probes that hybridize to each exon can have sequences that overlap with at least 1 other probe. In some embodiments, the oligoprobes can selectively hybridize to non-coding regions of genes disclosed herein, for example, intronic regions of the genes. The oligoprobes can also selectively hybridize to regions of genes comprising both exonic and intronic regions of the genes disclosed herein.

Any number of exons can be targeted by the oligonucleotide probes. For example, at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 400, 500, 600, 700, 800, 900, 1,000, or more, exons can be targeted.

The kit can comprise at least 4, 5, 6, 7, or 8 different library adaptors having distinct molecular barcodes and identical sample barcodes. The library adaptors may not be sequencing adaptors. For example, the library adaptors do not include flow cell sequences or sequences that permit the formation of hairpin loops for sequencing. The different variations and combinations of molecular barcodes and sample barcodes are described throughout, and are applicable to the kit. Further, in some cases, the adaptors are not sequencing adaptors. Additionally, the adaptors provided with the kit can also comprise sequencing adaptors. A sequencing adaptor can comprise a sequence hybridizing to one or more sequencing primers. A sequencing adaptor can further comprise a sequence hybridizing to a solid support, e.g., a flow cell sequence. For example, a sequencing adaptor can be a flow cell adaptor. The sequencing adaptors can be attached to one or both ends of a polynucleotide fragment. In some cases, the kit can comprise at least 8 different library adaptors having distinct molecular barcodes and identical sample barcodes. The library adaptors may not be sequencing adaptors. The kit can further include a sequencing adaptor having a first sequence that selectively hybridizes to the library adaptors and a second sequence that selectively hybridizes to a flow cell sequence. In another example, a sequencing adaptor can be hairpin shaped. For example, the hairpin shaped adaptor can comprise a complementary double stranded portion and a loop portion, where the double stranded portion can be attached {e.g., ligated) to a double-stranded polynucleotide. Hairpin shaped sequencing adaptors can be attached to both ends of a polynucleotide fragment to generate a circular molecule, which can be sequenced multiple times. A sequencing adaptor can be up to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more bases from end to end. The sequencing adaptor can comprise 20-30, 20-40, 30-50, 30-60, 40-60, 40-70, 50-60, 50-70, bases from end to end. In a particular example, the sequencing adaptor can comprise 20-30 bases from end to end. In another example, the sequencing adaptor can comprise 50-60 bases from end to end. A sequencing adaptor can comprise one or more barcodes. For example, a sequencing adaptor can comprise a sample barcode. The sample barcode can comprise a pre-determined sequence. The sample barcodes can be used to identify the source of the polynucleotides. The sample barcode can be at least 1, 2, 3, 4, 5, 6, 7, 8, 9, 10, 11, 12, 13, 14, 15, 16, 17, 18, 19, 20, 21, 22, 23, 24, 25, or more (or any length as described throughout) nucleic acid bases, e.g., at least 8 bases. The barcode can be contiguous or non-contiguous sequences, as described above.

The library adaptors can be blunt ended and Y-shaped and can be less than or equal to 40 nucleic acid bases in length. Other variations of the can be found throughout and are applicable to the kit.

All patents, patent applications, websites, other publications or documents, accession numbers and the like cited herein are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number, if applicable. Likewise, if different versions of a publication, website or the like are published at different times, the version most recently published at the effective filing date of the application is meant, unless otherwise indicated.

III. EXAMPLES

The following examples are provided to illustrate certain aspects of the disclosed methods. The examples do not limit the disclosure.

Example 1: Analysis of cfDNA to Detect the Presence/Absence of Tumor

A set of patient samples are analyzed by a blood-based NGS assay at Guardant Health (Redwood City, CA, USA) to detect the presence/absence of cancer. cfDNA is extracted from the plasma of these patients. cfDNA of the patient samples is then combined with methyl binding domain (MBD) buffers and magnetic beads conjugated with an MBD protein and incubated overnight. Methylated cfDNA (if present, in the cfDNA sample) is bound to the MBD protein during this incubation. Non-methylated or less methylated DNA is washed away from the beads with buffers containing increasing concentrations of salt. Finally, a high salt buffer is used to wash the heavily methylated DNA away from the MBD protein. These washes result in three partitions (hypomethylated, residual methylation and hypermethylated partitions) of increasingly methylated cfDNA.

The cfDNA molecules in the hypomethylated partition are subjected to a conversion procedure such as TAP that converts mC to a base read as T in sequencing (DHU in the case of TAP). Thus, nonspecifically partitioned DNA in the hypomethylated partition will show base conversions indicative of intermediate to hyper methylation.

Optionally, the cfDNA molecules in the hypermethylated partition are subjected to enzymatic modification (EM) with whereby unmodified cytosines, but not mC and hmC, undergo deamination, thereby marking nonspecifically partitioned hypomethylated molecules in the first subsample by conversion of unmodified cytosines to uracils.

Optionally, the cfDNA in the residual partition can be subjected to either conversion procedure to distinguish methylated from unmethylated C residues and identify nonspecifically partitioned molecules (hypomethylated or hypermethylated molecules).

The cfDNA molecules in the three partitions are cleaned, to remove salt, and concentrated in preparation for the enzymatic steps of library preparation. After concentrating the cfDNA in the partitions, the end overhangs of the partitioned cfDNA are extended, and adenosine residues are added to the 3' ends of the cfDNA fragment by the polymerase during the extension. The 5' end of each fragment is phosphorylated. These modifications make the partitioned cfDNA ligatable. DNA ligase and adapters are added to ligate each partitioned cfDNA molecule with an adapter on each end. These adapters contain non-unique molecular barcodes and each partition is ligated with adapters having non-unique molecular barcodes that is distinguishable from the barcodes in the adapters used in the other partitions. After ligation, the four partitions are pooled together and are amplified by PCR.

Following PCR, amplified DNA is washed and concentrated prior to enrichment. Once concentrated, the amplified DNA is combined with a salt buffer and biotinylated RNA probes that comprise probes for a sequence-variable target region set and probes for an epigenetic target region set and this mixture is incubated overnight. The probes for the sequence-variable region set has a footprint of about 50 kb and the probes for the epigenetic target region set has a footprint of about 500 kb. The probes for the sequence-variable target region set comprise oligonucleotides targeting at least a subset of genes identified in Tables 3-5 and the probes for the epigenetic target region set comprises oligonucleotides targeting a selection of hypermethylation variable target regions, hypomethylation variable target regions, CTCF binding target regions, transcription start site target regions, focal amplification target regions and methylation control regions.

The biotinylated RNA probes (hybridized to DNA) are captured by streptavidin magnetic beads and separated from the amplified DNA that are not captured by a series of salt based washes, thereby enriching the sample. After enrichment, an aliquot of the enriched sample is sequenced using Illumina NovaSeq sequencer. The sequence reads generated by the sequencer are then analyzed using bioinformatic tools/algorithms. The molecular barcodes are used to identify unique molecules as well as for deconvolution of the sample into molecules that were differentially MBD-partitioned. The method described in this example, apart from providing information on the overall level methylation (i.e., methylated cytosine residues) of a molecule based on its partition, can also provide a higher resolution information about the identity and/or location of the methylated cytosine (i.e., mC or hmC) and permit identification of nonspecifically partitioned molecules that show base conversion inconsistent with the partition in which they appeared. The sequence-variable target region sequences are analyzed by detecting genomic alterations such as SNVs, insertions, deletions and fusions that can be called with enough support that differentiates real tumor variants from technical errors (for e.g., PCR errors, sequencing errors). The epigenetic target region sequences are analyzed independently to detect methylation status of cfDNA molecules in regions that have been shown to be differentially methylated, e.g., in potentially cancerous tissue compared to healthy cfDNA. Molecules showing base conversion indicative of nonspecific partitioning can be excluded from this analysis to increase accuracy and/or sensitivity. Finally, the results of both analysis are combined to produce a final tumor present/absent call.

Example 2: Analysis of Methylation at Single Nucleotide Resolution in cfDNA Samples from Healthy Subjects and Subjects with Early-Stage Colorectal Cancer Samples of cfDNA from healthy subjects and subjects with early-stage colorectal cancer were analyzed as follows. cfDNA was partitioned using MBD to provide a hypermethylated partition, an intermediate partition, and a hypomethylated partition. The partitioned DNA of each partition was ligated to adapters and subjected to an EM-seq conversion procedure whereby unmodified cytosines, but not mC and hmC, undergo deamination, although in an alternative procedure the cfDNA molecules in the hypomethylated partition may be subjected to a conversion procedure such as TAP that converts mC to a base read as T in sequencing (DHU in the case of TAP), so that nonspecifically partitioned DNA in the hypomethylated partition would show base conversions indicative of intermediate to hyper methylation. Following deamination, the partitions were prepared for sequencing and subjected to whole-genome sequencing. Each partition was sequenced separately, although in an alternative procedure the partitions could be differentially tagged (e.g., after partitioning and before EM-seq conversion, or after partitioning and EM-seq conversion and before further preparation for sequencing), pooled, and processed sequenced in parallel.

Figure 5:
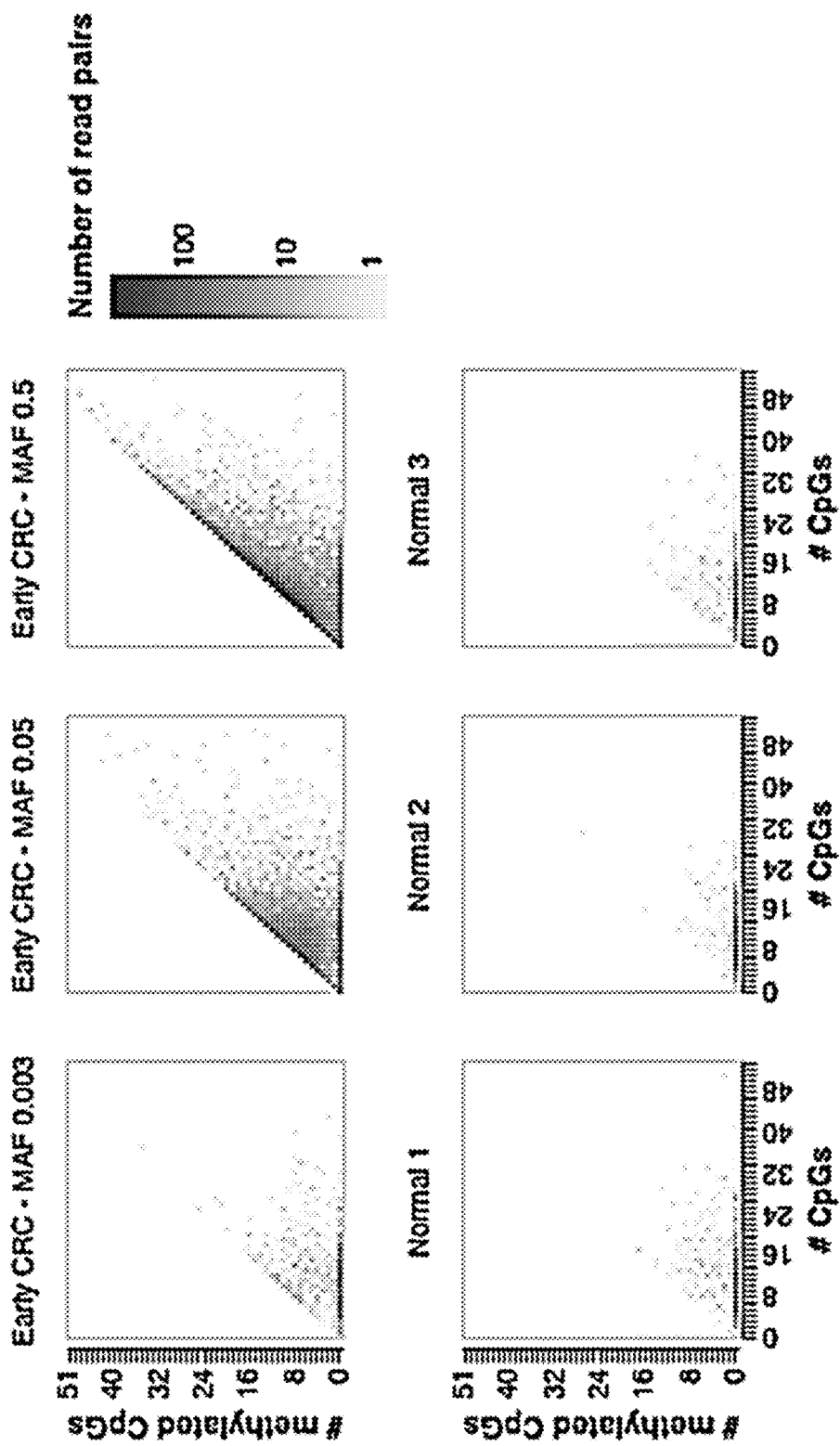
FIG. 5 shows CpG methylation quantification results obtained as described in Example 2 for three samples from subjects with early stage colorectal cancer ("Early CRC") and three healthy subjects ("Normal"). For the Early CRC plots, MAF indicates mutant allele fraction.

Sequence data from hypermethylation variable target regions was isolated bioinformatically, although in an alternative procedure target regions could be enriched in vitro before sequencing. Per-base methylation for the hypermethylation variable target regions was quantified as shown in FIG. 5, which shows the number of methylated CpG per molecule in the hypermethylation variable target regions from the hypermethylated partition. The x-axis indicates the total number of CpGs per molecule, such that points along the diagonal represent molecules with methylation at every CpG. Thus, it was possible to analyze methylation at single-base resolution and quantify per base methylation and partial molecule methylation of the MBD-partitioned material. The samples from subjects with colorectal cancer exhibited much higher overall methylation in these regions than samples from healthy subjects.

Example 3: Reduction of Technical Noise by Digestion of Nonspecifically Partitioned DNA A pool of cfDNA from two healthy normal samples was combined, from which 18.6 ng was used as input to a MBD-partitioning assay described herein. To a subset of the samples, cfDNA from a colorectal cancer sample (CRC) with 0.5% MAF (mutant allele fraction) was added, resulting in a diluted CRC sample with 0.16% MAF. Three sets of normal samples and diluted CRC samples were used in the assay. The three sets of samples were then partitioned using MBD protein into three partitions (hyper, residual and hypo partitions). Following cleanup, the cfDNA molecules in each partition was ligated with partition-specific adapters comprising molecular barcodes.

The molecular barcodes use in hyper and residual partition are selected such that they do not have MSRE recognition sites, so they are not digested in the downstream processing (irrespective of cfDNA methylation state). Post-ligation, ligation cleanups were performed. Following the ligation cleanup, the hyper and residual partitions were subjected to MSRE digestion reactions. A first set of the samples (normal and diluted CRC samples) were treated with BstUI and HpaII and another set of the samples were treated BstUI, HpaII and Hin6I enzymes. The third set of samples were run through a mock digest (no MSREs) in the MBD-partitioning assay as a control. After the MSRE digestion, the enzymes were heat inactivated (65C, 20 min) and cleaned up using SPRI beads. After the digest cleanups, the hyper, residual and (non-digested) hypo partitions (adapter-ligated cfDNA) were combined and proceed through an NGS assay workflow comprising PCR amplification; enrichment of molecules in genomic regions of interest; pooling of samples thereby allowing multiplexed sequencing and sequencing the pooled sample using NovaSeq.

Figure 6:
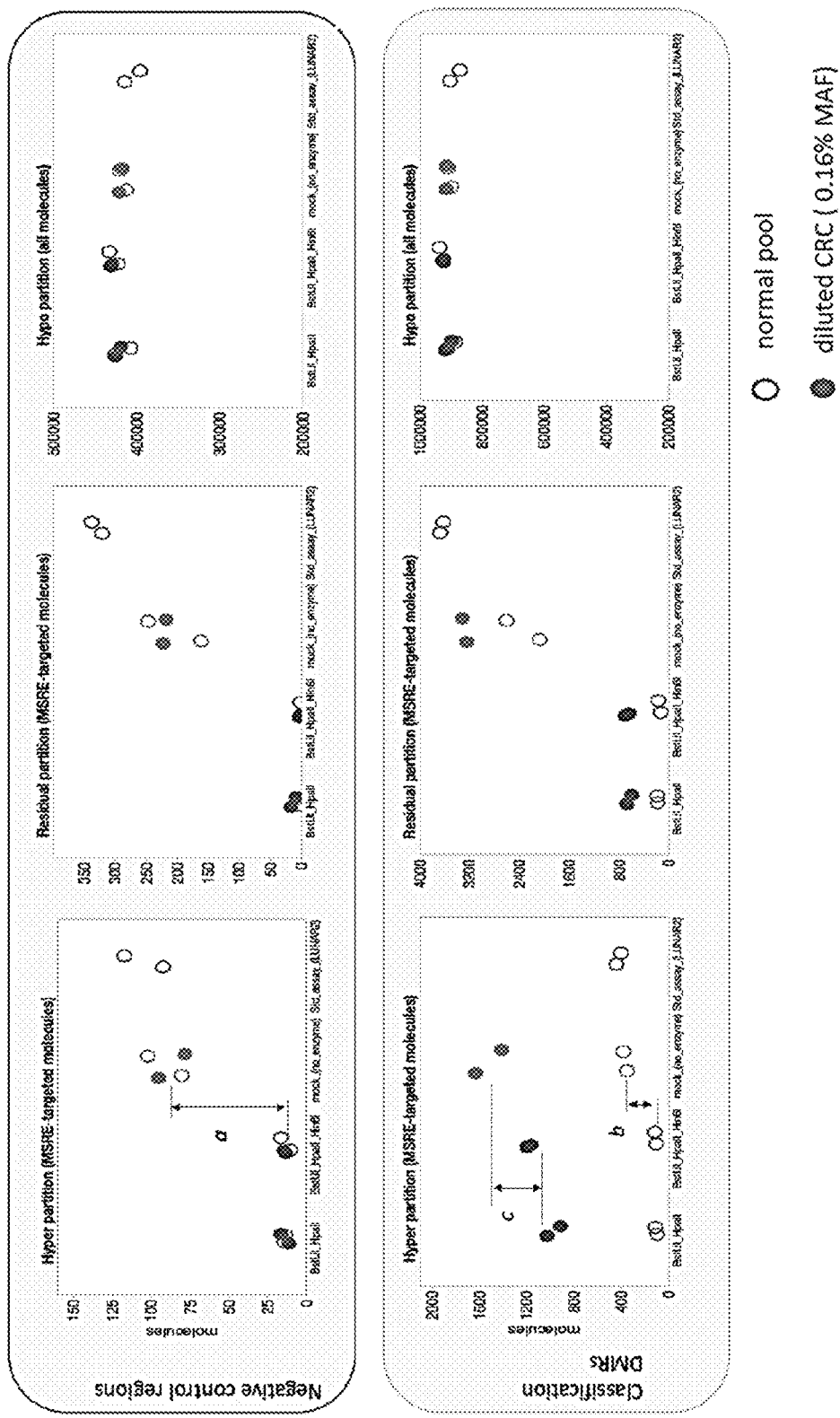
FIG. 6 shows the molecule count in the three partitions with and without MSRE treatments in normal and diluted CRC samples.

FIG. 6 clearly shows the increase in cancer methylation signal at DMRs relative to the technical noise from unmethylated molecules in normal samples when the MSRE digestion was applied. In the negative control regions (where the DNA molecules are non-methylated at almost all times irrespective of the disease state) shown in FIG. 6, "a" clearly indicates that it was clear that the MSRE digestion removes the unmethylated molecules that mis-partitioned into the hyper partition—90 molecules were partitioned into hyper partition in the mock digestion whereas in BstUI, HpaII and Hin6I digestion the molecule count was reduced to 10. In the classification DMRs shown in FIG. 6, cfDNA molecules were removed by much higher proportion in normal samples (b; 350→100) than diluted CRC samples (c; 1500→1100) upon digestion with MSREs.

As described elsewhere herein, the hypo partition (second subsample) may be subjected to a procedure that affects a first nucleobase in the DNA differently from a second nucleobase in the DNA of the second subsample, wherein the first nucleobase is a modified or unmodified nucleobase, the second nucleobase is a modified or unmodified nucleobase different from the first nucleobase, and the first nucleobase and the second nucleobase have the same base pairing specificity, e.g., such as TAP that converts mC to a base read as T in sequencing (DHU in the case of TAP) so that nonspecifically partitioned DNA in the hypomethylated partition will show base conversions indicative of intermediate to hyper methylation. The procedure may be used, e.g., after partitioning and/or before ligation of the partition-specific adapters, or at any other appropriate stage as described elsewhere herein.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the disclosure described herein may be employed in practicing the invention. It is therefore contemplated that the disclosure shall also cover any such alternatives, modifications, variations or equivalents. It is intended that the following claims define the scope of the invention and that methods and structures within the scope of these claims and their equivalents be covered thereby.

While the foregoing disclosure has been described in some detail by way of illustration and example for purposes of clarity and understanding, it will be clear to one of ordinary skill in the art from a reading of this disclosure that various changes in form and detail can be made without departing from the true scope of the disclosure and may be practiced within the scope of the appended claims. For example, all the methods, systems, computer readable media, and/or component features, steps, elements, or other aspects thereof can be used in various combinations.

All patents, patent applications, websites, other publications or documents, accession numbers and the like cited herein are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number, if applicable. Likewise, if different versions of a publication, website or the like are published at different times, the version most recently published at the effective filing date of the application is meant, unless otherwise indicated.

What is claimed is:

1. A method of analyzing DNA in a sample, the method comprising:
    a) partitioning the sample into a plurality of subsamples, including a first subsample and a second subsample, wherein the first subsample comprises DNA with a cytosine modification in a greater proportion than the second subsample;
    b) subjecting the second subsample to a base conversion procedure that affects a first nucleobase in the DNA differently from a second nucleobase in the DNA of the second subsample, wherein the first nucleobase is a modified or unmodified nucleobase, the second nucleobase is a modified or unmodified nucleobase different from the first nucleobase, and the first nucleobase and the second nucleobase have the same base pairing specificity, thereby producing a treated subsample;
    c) capturing a target region set comprising epigenetic target regions from the treated subsample; and
    d) sequencing DNA in the target region set and DNA from the first subsample, wherein DNA from the second subsample is sequenced in a manner that distinguishes the first nucleobase from the second nucleobase in the DNA of the target region set.

2. The method of claim 1, wherein the target region set comprises a hypomethylation variable target region set.

3. The method of claim 2, wherein the hypomethylation variable target region set comprises regions having a lower degree of methylation in at least one type of tissue than the degree of methylation in cell-free DNA from a healthy subject.

4. The method of claim 1, wherein the target region set comprises a fragmentation variable target region set.

5. The method of claim 4, wherein the fragmentation variable target region set comprises transcription start site regions and/or CTCF binding regions.

6. The method of claim 1, wherein the target region set further comprises sequence-variable target regions.

7. The method of claim 6, comprising sequencing DNA molecules corresponding to the sequence-variable target region set to a greater depth of sequencing than DNA molecules corresponding to the epigenetic target region set.

8. The method of claim 1, wherein the DNA of the first subsample is contacted with a methylation-sensitive nuclease, thereby degrading nonspecifically partitioned DNA in the first subsample.

9. The method of claim 1, wherein the DNA comprises cell-free DNA (cfDNA) obtained from a test subject.

10. The method of claim 1, further comprising subjecting the first subsample to a procedure that affects a first nucleobase in the DNA differently from a second nucleobase in the DNA of the second subsample, wherein the first nucleobase is a modified or unmodified nucleobase, the second nucleobase is a modified or unmodified nucleobase different from the first nucleobase, and the first nucleobase and the second nucleobase have the same base pairing specificity, thereby producing an additional treated subsample.

11. The method of claim 10, further comprising capturing an additional target region set from the additional treated subsample, wherein the additional target region set comprises a hypermethylation variable target region set, a fragmentation variable target region set, and/or sequence-variable target regions.

12. The method of claim 11, wherein the hypermethylation variable target region set comprises regions having a higher degree of methylation in at least one type of tissue than the degree of methylation in cell-free DNA from a healthy subject.

13. The method of claim 11, wherein the fragmentation variable target region set comprises transcription start site regions and/or CTCF binding regions.

14. The method of claim 1, wherein capturing comprises contacting DNA to be captured with a set of target-specific probes, whereby complexes of target-specific probes and DNA are formed.

15. The method of claim 1, further comprising ligating barcode-containing adapters to the DNA before capture, optionally wherein the ligating occurs before or simultaneously with amplification.

16. The method of claim 1, wherein partitioning the sample into a plurality of subsamples comprises partitioning on the basis of methylation level.

17. The method of claim 1, comprising differentially tagging the first subsample and second subsample or the first subsample and the treated subsample.

18. The method of claim 17, wherein DNA from the first subsample and the target region set or second subsample are pooled.

19. The method of claim 1, wherein the plurality of subsamples comprises a third subsample, which comprises DNA with a cytosine modification in a greater proportion than the second subsample but in a lesser proportion than the first subsample.

20. The method of claim 19, wherein the method further comprises differentially tagging DNA from the third subsample and DNA from the first subsample, and wherein DNA from the third sample and the target region set are pooled, optionally wherein DNA from the first, second, and third subsamples is sequenced in the same sequencing cell.

21. The method of claim 1, further comprising determining a likelihood that the subject has cancer.

22. The method of claim 1, wherein the first nucleobase is a modified or unmodified cytosine and the second nucleobase is a modified or unmodified cytosine.

23. The method of claim 22, wherein the first nucleobase comprises unmodified cytosine (C) and the second nucleobase comprises 5-methylcytosine (mC) or 5-hydroxymethylcytosine (hmC).

24. The method of claim 23, wherein the base conversion procedure to which the second subsample is subjected comprises Tet-assisted conversion with a substituted borane reducing agent, wherein the substituted borane reducing agent is 2-picoline borane, borane pyridine, tert-butylamine borane, or ammonia borane.

* * * * *